United States Patent [19]

*Payne et al.

[11] Patent Number: 6,077,937
[45] Date of Patent: Jun. 20, 2000

[54] *BACILLUS THURINGIENSIS* TOXINS ACTIVE AGAINST HYMENOPTERAN PESTS

[75] Inventors: Jewel M. Payne, Davis, Calif.; M. Keith Kennedy, Racine, Wis.; John Brookes Randall, Racine, Wis.; Henry Meier, Racine, Wis.; Heidi Jane Uick, Racine, Wis.; Luis Foncerrada; H. Ernest Schnepf, both of San Diego, Calif.; George E. Schwab, Encinitas, Calif.; Jenny Fu, San Diego, Calif.

[73] Assignee: Mycogen Corporation, San Diego, Calif.

[ * ] Notice: This patent is subject to a terminal disclaimer.

[21] Appl. No.: 09/173,891

[22] Filed: Oct. 16, 1998

Related U.S. Application Data

[62] Division of application No. 08/611,928, Mar. 6, 1996, which is a continuation of application No. 08/158,232, Nov. 24, 1993, Pat. No. 5,596,071, which is a continuation-in-part of application No. 07/887,980, May 22, 1992, abandoned, which is a continuation-in-part of application No. 07/703,977, May 22, 1991, Pat. No. 5,260,058, and a continuation-in-part of application No. 07/797,645, Nov. 25, 1991, Pat. No. 5,268,297.

[51] Int. Cl.[7] .............................. C07K 1/00; C07H 21/04; G01N 33/00; A61K 38/00
[52] U.S. Cl. .................. 530/350; 536/23.71; 536/24.33; 436/94; 514/12
[58] Field of Search .......................... 530/350; 536/23.71, 536/24.33; 436/94; 514/12

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,797,276 | 1/1989 | Herrnstadt et al. | 424/84 |
| 4,849,217 | 7/1989 | Soares et al. | 424/93 |
| 4,853,331 | 8/1989 | Herrnstadt et al. | 435/251.1 |
| 4,918,006 | 4/1990 | Ellar et al. | 435/69.1 |
| 4,948,734 | 8/1990 | Edwards et al. | 435/252.5 |
| 5,151,363 | 9/1992 | Payne | 435/252.5 |
| 5,208,077 | 5/1993 | Proctor et al. | 427/461 |

FOREIGN PATENT DOCUMENTS

| | | |
|---|---|---|
| 0200344 | 12/1986 | European Pat. Off. . |
| 0303426 | 2/1989 | European Pat. Off. . |
| 0462721 | 12/1991 | European Pat. Off. . |
| 0471564 | 2/1992 | European Pat. Off. . |

OTHER PUBLICATIONS

Vankova, J. et al. (1975) "The Control of *Monomorium pharaonis* (Hymenoptera: Formicidae) with *Bacillus thuringiensis*" Journal of Invertebrate Pathology 26:159–163.

Wisniewski, J. (1975) "Controlling Pharoah Ants in the Zoo with *Bacillus thuringiensis*" Angew. Parasitol. 16(1):43–49, **abstract No. 36681—Biological Abstracts, vol. 60.

Gaertner, F.H., L. Kim (1988) "Current Applied Recombinant DNA Projects" TIBTECH 6:S4–S7.

Gaertner, F. (1989) "Cellular Delivery System for Insecticidal Proteins: Living and Non–Living Microorganisms" in Controlled Delivery of Crop–Protection Agents, pp. 245–255.

Couch, T.L. (1980) "Mosquito Pathogenicity of *Bacillus thuringiensis* var. *israelensis*" Developments in Industrial Microbiology 22:61–76.

Beegle, C.C. (1978) "Use of Entomogenous Bacteria in Agroecosystems" Developments in Industrial Microbiology 20:97–104.

(List continued on next page.)

*Primary Examiner*—Karen Cochrane Carlson
*Assistant Examiner*—Devesh Srivastava
*Attorney, Agent, or Firm*—Saliwanchik, Lloyd & Saliwanchik

[57] ABSTRACT

Novel *Bacillus thuringiensis* toxins with hymenopteran activity are described.

15 Claims, 5 Drawing Sheets

1. *Bacillus thuringiensis* PS140E2
2. *Bacillus thuringiensis* PS86Q3

OTHER PUBLICATIONS

Krieg, V.A. et al. (1983) "*Bacillus thuringiensis* var *tenebrionis*: Ein Neuer, Gegenuber Larven von Coleopteran Wirksamer Pathotyp" Z. Ang. Ent. 96:500–508.

Hofte, H., H.R. Whiteley (1989) "Insecticidal Crystal Proteins of *Bacillus thuringiensis*" Microbiological Reviews 52(2):242–255.

Feitelson, J.S. et al. (1992) "*Bacillus thuringiensis*: Insects and Beyond" Bio/Technology 10:271–275.

Schnepf, H.E., H.R. Whiteley (1981) "Cloning and Expression of the *Bacillus thuringiensis* Crystal Protein Gene in *Escherichia Coli*" Proc. Natl. Acad. Sci. USA 78(5):2893–2897.

Holldobler, B., E.O. Wilson (1990) "The Harvesting of Ants" in the Ants, pp. 609–617.

Habermehl, G.G. (1981) "Formicinae (Ants)" in Venomous Animals and Their Toxins, pp. 81–83.

Akre, R.D. et al. (1989) "Carpenter Ants: Their Biology and Control" Ext. Bull. Washington State Univ. Coop. Ext. Serv., No. EB 0818, p. 1–6.

Beaston, S.H. (1972) "Pharaoh's Ants as Pathogen Vectors in Hospitals" The Lacent 1:425–427.

Ebeling, W. (1978) Urban Entomology, Univ. CA: Berkeley pp. 209–213.

FIG. 1

1. *Bacillus thuringiensis* PS140E2
2. *Bacillus thuringiensis* PS86Q3

FIG. 2

| kDa |
|---|
| 205 |
| 116 |
| 97.4 |
| 66 |
| 45 |
| 29 |

A   B

A. *Bacillus thuringiensis* PS211B2
B. Protein Standard

```
                          SEQUENCE LISTING (1) GENERAL INFORMATION:

(iii) NUMBER OF SEQUENCES: 51

(2) INFORMATION FOR SEQ ID NO:1:

(i) SEQUENCE CHARACTERISTICS:
        (A) LENGTH: 4155 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus thuringiensis
        (B) STRAIN: PS17
        (C) INDIVIDUAL ISOLATE: PS17a (vii) IMMEDIATE SOURCE:
        (B) CLONE: E. coli NM522(pMYC1627) NRRL B-18651

(xi) SEQUENCE DESCRIPTION: SEQ ID NO:1:
```

-continued

```
ATGGCAATTT TAAATGAATT ATATCCATCT GTACCTTATA ATGTATTGGC GTATACGCCA      60

CCCTCTTTTT TACCTGATGC GGGTACACAA GCTACACCTG CTGACTTAAC AGCTTATGAA     120

CAATTGTTGA AAAATTTAGA AAAAGGGATA AATGCTGGAA CTTATTCGAA AGCAATAGCT     180

GATGTACTTA AAGGTATTTT TATAGATGAT ACAATAAATT ATCAAACATA TGTAAATATT     240

GGTTTAAGTT TAATTACATT AGCTGTACCG GAAATTGGTA TTTTTACACC TTTCATCGGT     300

TTGTTTTTTG CTGCATTGAA TAAACATGAT GCTCCACCTC CTCCTAATGC AAAAGATATA     360

TTTGAGGCTA TGAAACCAGC GATTCAAGAG ATGATTGATA GAACTTTAAC TGCGGATGAG     420

CAAACATTTT TAAATGGGGA AATAAGTGGT TTACAAAATT TAGCAGCAAG ATACCAGTCT     480

ACAATGGATG ATATTCAAAG CCATGGAGGA TTTAATAAGG TAGATTCTGG ATTAATTAAA     540

AAGTTTACAG ATGAGGTACT ATCTTTAAAT AGTTTTTATA CAGATCGTTT ACCTGTATTT     600

ATTACAGATA ATACAGCGGA TCGAACTTTG TTAGGTCTTC CTTATTATGC TATACTTGCG     660

AGCATGCATC TTATGTTATT AAGAGATATC ATTACTAAGG GTCCGACATG GGATTCTAAA     720

ATTAATTTCA CACCAGATGC AATTGATTCC TTTAAAACCG ATATTAAAAA TAATATAAAG     780

CTTTACTCTA AAACTATTTA TGACGTATTT CAGAAGGGAC TTGCTTCATA CGGAACGCCT     840

TCTGATTTAG AGTCCTTTGC AAAAAAACAA AAATATATTG AAATTATGAC AACACATTGT     900

TTAGATTTTG CAAGATTGTT TCCTACTTTT GATCCAGATC TTTATCCAAC AGGATCAGGT     960

GATATAAGTT TACAAAAAAC ACGTAGAATT CTTTCTCCTT TTATCCCTAT ACGTACTGCA    1020

GATGGGTTAA CATTAAATAA TACTTCAATT GATACTTCAA ATTGGCCTAA TTATGAAAAT    1080

GGGAATGGCG CGTTTCCAAA CCCAAAAGAA AGAATATTAA AACAATTCAA ACTGTATCCT    1140

AGTTGGAGAG CGGGACAGTA CGGTGGGCTT TTACAACCTT ATTTATGGGC AATAGAAGTC    1200

CAAGATTCTG TAGAGACTCG TTTGTATGGG CAGCTTCCAG CTGTAGATCC ACAGGCAGGG    1260

CCTAATTATG TTTCCATAGA TTCTTCTAAT CCAATCATAC AAATAAATAT GGATACTTGG    1320

AAAACACCAC CACAAGGTGC GAGTGGGTGG AATACAAATT TAATGAGAGG AAGTGTAAGC    1380

GGGTTAAGTT TTTTACAACG AGATGGTACG AGACTTAGTG CTGGTATGGG TGGTGGTTTT    1440

GCTGATACAA TATATAGTCT CCCTGCAACT CATTATCTTT CTTATCTCTA TGGAACTCCT    1500

TATCAAACTT CTGATAACTA TTCTGGTCAC GTTGGTGCAT TGGTAGGTGT GAGTACGCCT    1560

CAAGAGGCTA CTCTTCCTAA TATTATAGGT CAACCAGATG AACAGGGAAA TGTATCTACA    1620

ATGGGATTTC CGTTTGAAAA AGCTTCTTAT GGAGGTACAG TTGTTAAAGA ATGGTTAAAT    1680

GGTGCGAATG CGATGAAGCT TTCTCCTGGG CAATCTATAG GTATTCCTAT TACAAATGTA    1740

ACAAGTGGAG AATATCAAAT TCGTTGTCGT TATGCAAGTA ATGATAATAC TAACGTTTTC    1800

TTTAATGTAG ATACTGGTGG AGCAAATCCA ATTTTCCAAC AGATAAACTT TGCATCTACT    1860

GTAGATAATA ATACGGGAGT ACAAGGAGCA AATGGTGTCT ATGTAGTCAA ATCTATTGCT    1920

ACAACTGATA ATTCTTTTAC AGAAATTCCT GCGAAGACGA TTAATGTTCA TTTAACCAAC    1980

CAAGGTTCTT CTGATGTCTT TTTAGACCGT ATTGAATTTA TACCTTTTTC TCTACCTCTT    2040

ATATATCATG GAAGTTATAA TACTTCATCA GGTGCAGATG ATGTTTTATG GTCTTCTTCA    2100

AATATGAATT ACTACGATAT AATAGTAAAT GGTCAGGCCA ATAGTAGTAG TATCGCTAGT    2160

TCTATGCATT TGCTTAATAA AGGAAAAGTG ATAAAAACAA TTGATATTCC AGGGCATTCG    2220

GAAACCTTCT TTGCTACGTT CCCAGTTCCA GAAGGATTTA TGAAGTTAG AATTCTTGCT    2280

GGCCTTCCAG AAGTTAGTGG AAATATTACC GTACAATCTA ATAATCCGCC TCAACCTAGT    2340
```

```
AATAATGGTG GTGGTGATGG TGGTGGTAAT GGTGGTGGTG ATGGTGGTCA ATACAATTTT    2400

TCTTTAAGCG GATCTGATCA TACGACTATT TATCATGGAA AACTTGAAAC TGGGATTCAT    2460

GTACAAGGTA ATTATACCTA TACAGGTACT CCCGTATTAA TACTGAATGC TTACAGAAAT    2520

AATACTGTAG TATCAAGCAT TCCAGTATAT TCTCCTTTTG ATATAACTAT ACAGACAGAA    2580

GCTGATAGCC TTGAGCTTGA ACTACAACCT AGATATGGTT TTGCCACAGT GAATGGTACT    2640

GCAACAGTAA AAAGTCCTAA TGTAAATTAC GATAGATCAT TTAAACTCCC AATAGACTTA    2700

CAAAATATCA CAACACAAGT AAATGCATTA TTCGCATCTG GAACACAAAA TATGCTTGCT    2760

CATAATGTAA GTGATCATGA TATTGAAGAA GTTGTATTAA AAGTGGATGC CTTATCAGAT    2820

GAAGTATTTG GAGATGAGAA GAAGGCTTTA CGTAAATTGG TGAATCAAGC AAAACGTTTG    2880

AGTAGAGCAA GAAATCTTCT GATAGGTGGG AGTTTTGAAA ATTGGGATGC ATGGTATAAA    2940

GGAAGAAATG TAGTAACTGT ATCTGATCAT GAACTATTTA AGAGTGATCA TGTATTATTA    3000

CCACCACCAG GATTGTCTCC ATCTTATATT TTCCAAAAAG TGGAGGAATC TAAATTAAAA    3060

CCAAATACAC GTTATATTGT TTCTGGATTC ATCGCACATG GAAAAGACCT AGAAATTGTT    3120

GTTTCACGTT ATGGGCAAGA AGTGCAAAAG GTCGTGCAAG TTCCTTATGG AGAAGCATTC    3180

CCGTTAACAT CAAATGGACC AGTTTGTTGT CCCCCACGTT CTACAAGTAA TGGAACCTTA    3240

GGAGATCCAC ATTTCTTTAG TTACAGTATC GATGTAGGTG CACTAGATTT ACAAGCAAAC    3300

CCTGGTATTG AATTTGGTCT TCGTATTGTA AATCCAACTG GAATGGCACG CGTAAGCAAT    3360

TTGGAAATTC GTGAAGATCG TCCATTAGCA GCAAATGAAA TACGACAAGT ACAACGTGTC    3420

GCAAGAAATT GGAGAACCGA GTATGAGAAA GAACGTGCGG AAGTAACAAG TTTAATTCAA    3480

CCTGTTATCA ATCGAATCAA CGGATTGTAT GAAAATGGAA ATTGGAACGG TTCTATTCGT    3540

TCAGATATTT CGTATCAGAA TATAGACGCG ATTGTATTAC CAACGTTACC AAAGTTACGC    3600

CATTGGTTTA TGTCAGATAG ATTCAGTGAA CAAGGAGATA TAATGGCTAA ATTCCAAGGT    3660

GCATTAAATC GTGCGTATGC ACAACTGGAA CAAAGTACGC TTCTGCATAA TGGTCATTTT    3720

ACAAAAGATG CAGCTAATTG GACAATAGAA GGCGATGCAC ATCAGATAAC ACTAGAAGAT    3780

GGTAGACGTG TATTGCGACT TCCAGATTGG TCTTCGAGTG TATCTCAAAT GATTGAAATC    3840

GAGAATTTTA ATCCAGATAA AGAATACAAC TTAGTATTCC ATGGGCAAGG AGAAGGAACG    3900

GTTACGTTGG AGCATGGAGA AGAAACAAAA TATATAGAAA CGCATACACA TCATTTTGCG    3960

AATTTTACAA CTTCTCAACG TCAAGGACTC ACGTTTGAAT CAAATAAAGT GACAGTGACC    4020

ATTTCTTCAG AAGATGGAGA ATTCTTAGTG GATAATATTG CGCTTGTGGA AGCTCCTCTT    4080

CCTACAGATG ACCAAAATTC TGAGGGAAAT ACGGCTTCCA GTACGAATAG CGATACAAGT    4140

ATGAACAACA ATCAA                                                    4155

(2) INFORMATION FOR SEQ ID NO:2:

(i) SEQUENCE CHARACTERISTICS:
        (A) LENGTH: 1385 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: BACILLUS THURINGIENSIS
```

(B) STRAIN: PS17
(C) INDIVIDUAL ISOLATE: PS17a (vii) IMMEDIATE SOURCE:
(B) CLONE: E. coli NM522(pMYC1627) NRRL B-18651

(xi) SEQUENCE DESCRIPTION: SEQ ID NO:2:

```
Met Ala Ile Leu Asn Glu Leu Tyr Pro Ser Val Pro Tyr Asn Val Leu
1               5                   10                  15

Ala Tyr Thr Pro Pro Ser Phe Leu Pro Asp Ala Gly Thr Gln Ala Thr
            20                  25                  30

Pro Ala Asp Leu Thr Ala Tyr Glu Gln Leu Leu Lys Asn Leu Glu Lys
        35                  40                  45

Gly Ile Asn Ala Gly Thr Tyr Ser Lys Ala Ile Ala Asp Val Leu Lys
50                  55                  60

Gly Ile Phe Ile Asp Asp Thr Ile Asn Tyr Gln Thr Tyr Val Asn Ile
65                  70                  75                  80

Gly Leu Ser Leu Ile Thr Leu Ala Val Pro Glu Ile Gly Ile Phe Thr
                85                  90                  95

Pro Phe Ile Gly Leu Phe Phe Ala Ala Leu Asn Lys His Asp Ala Pro
            100                 105                 110

Pro Pro Pro Asn Ala Lys Asp Ile Phe Glu Ala Met Lys Pro Ala Ile
        115                 120                 125

Gln Glu Met Ile Asp Arg Thr Leu Thr Ala Asp Glu Gln Thr Phe Leu
130                 135                 140

Asn Gly Glu Ile Ser Gly Leu Gln Asn Leu Ala Ala Arg Tyr Gln Ser
145                 150                 155                 160

Thr Met Asp Asp Ile Gln Ser His Gly Gly Phe Asn Lys Val Asp Ser
                165                 170                 175

Gly Leu Ile Lys Lys Phe Thr Asp Glu Val Leu Ser Leu Asn Ser Phe
            180                 185                 190

Tyr Thr Asp Arg Leu Pro Val Phe Ile Thr Asp Asn Thr Ala Asp Arg
        195                 200                 205

Thr Leu Leu Gly Leu Pro Tyr Tyr Ala Ile Leu Ala Ser Met His Leu
210                 215                 220

Met Leu Leu Arg Asp Ile Ile Thr Lys Gly Pro Thr Trp Asp Ser Lys
225                 230                 235                 240

Ile Asn Phe Thr Pro Asp Ala Ile Asp Ser Phe Lys Thr Asp Ile Lys
                245                 250                 255

Asn Asn Ile Lys Leu Tyr Ser Lys Thr Ile Tyr Asp Val Phe Gln Lys
            260                 265                 270

Gly Leu Ala Ser Tyr Gly Thr Pro Ser Asp Leu Glu Ser Phe Ala Lys
        275                 280                 285

Lys Gln Lys Tyr Ile Glu Ile Met Thr Thr His Cys Leu Asp Phe Ala
290                 295                 300

Arg Leu Phe Pro Thr Phe Asp Pro Asp Leu Tyr Pro Thr Gly Ser Gly
305                 310                 315                 320

Asp Ile Ser Leu Gln Lys Thr Arg Arg Ile Leu Ser Pro Phe Ile Pro
                325                 330                 335

Ile Arg Thr Ala Asp Gly Leu Thr Leu Asn Asn Thr Ser Ile Asp Thr
            340                 345                 350

Ser Asn Trp Pro Asn Tyr Glu Asn Gly Asn Gly Ala Phe Pro Asn Pro
        355                 360                 365

Lys Glu Arg Ile Leu Lys Gln Phe Lys Leu Tyr Pro Ser Trp Arg Ala
370                 375                 380
```

```
Gly Gln Tyr Gly Gly Leu Leu Gln Pro Tyr Leu Trp Ala Ile Glu Val
385                 390                 395                 400

Gln Asp Ser Val Glu Thr Arg Leu Tyr Gly Gln Leu Pro Ala Val Asp
            405                 410                 415

Pro Gln Ala Gly Pro Asn Tyr Val Ser Ile Asp Ser Ser Asn Pro Ile
            420                 425                 430

Ile Gln Ile Asn Met Asp Thr Trp Lys Thr Pro Pro Gln Gly Ala Ser
            435                 440                 445

Gly Trp Asn Thr Asn Leu Met Arg Gly Ser Val Ser Gly Leu Ser Phe
450                 455                 460

Leu Gln Arg Asp Gly Thr Arg Leu Ser Ala Gly Met Gly Gly Gly Phe
465                 470                 475                 480

Ala Asp Thr Ile Tyr Ser Leu Pro Ala Thr His Tyr Leu Ser Tyr Leu
            485                 490                 495

Tyr Gly Thr Pro Tyr Gln Thr Ser Asp Asn Tyr Ser Gly His Val Gly
            500                 505                 510

Ala Leu Val Gly Val Ser Thr Pro Gln Glu Ala Thr Leu Pro Asn Ile
            515                 520                 525

Ile Gly Gln Pro Asp Glu Gln Gly Asn Val Ser Thr Met Gly Phe Pro
530                 535                 540

Phe Glu Lys Ala Ser Tyr Gly Gly Thr Val Val Lys Glu Trp Leu Asn
545                 550                 555                 560

Gly Ala Asn Ala Met Lys Leu Ser Pro Gly Gln Ser Ile Gly Ile Pro
            565                 570                 575

Ile Thr Asn Val Thr Ser Gly Glu Tyr Gln Ile Arg Cys Arg Tyr Ala
            580                 585                 590

Ser Asn Asp Asn Thr Asn Val Phe Phe Asn Val Asp Thr Gly Gly Ala
            595                 600                 605

Asn Pro Ile Phe Gln Gln Ile Asn Phe Ala Ser Thr Val Asp Asn Asn
            610                 615                 620

Thr Gly Val Gln Gly Ala Asn Gly Val Tyr Val Val Lys Ser Ile Ala
625                 630                 635                 640

Thr Thr Asp Asn Ser Phe Thr Glu Ile Pro Ala Lys Thr Ile Asn Val
            645                 650                 655

His Leu Thr Asn Gln Gly Ser Ser Asp Val Phe Leu Asp Arg Ile Glu
            660                 665                 670

Phe Ile Pro Phe Ser Leu Pro Leu Ile Tyr His Gly Ser Tyr Asn Thr
            675                 680                 685

Ser Ser Gly Ala Asp Asp Val Leu Trp Ser Ser Asn Met Asn Tyr
690                 695                 700

Tyr Asp Ile Ile Val Asn Gly Gln Ala Asn Ser Ser Ile Ala Ser
705                 710                 715                 720

Ser Met His Leu Leu Asn Lys Gly Lys Val Ile Lys Thr Ile Asp Ile
            725                 730                 735

Pro Gly His Ser Glu Thr Phe Phe Ala Thr Phe Pro Val Pro Glu Gly
            740                 745                 750

Phe Asn Glu Val Arg Ile Leu Ala Gly Leu Pro Glu Val Ser Gly Asn
            755                 760                 765

Ile Thr Val Gln Ser Asn Asn Pro Pro Gln Pro Ser Asn Asn Gly Gly
            770                 775                 780

Gly Asp Gly Gly Gly Asn Gly Gly Asp Gly Gly Gln Tyr Asn Phe
785                 790                 795                 800
```

-continued

```
Ser Leu Ser Gly Ser Asp His Thr Thr Ile Tyr His Gly Lys Leu Glu
            805                 810                 815

Thr Gly Ile His Val Gln Gly Asn Tyr Thr Tyr Thr Gly Thr Pro Val
            820                 825                 830

Leu Ile Leu Asn Ala Tyr Arg Asn Asn Thr Val Val Ser Ser Ile Pro
            835                 840                 845

Val Tyr Ser Pro Phe Asp Ile Thr Ile Gln Thr Glu Ala Asp Ser Leu
    850                 855                 860

Glu Leu Glu Leu Gln Pro Arg Tyr Gly Phe Ala Thr Val Asn Gly Thr
865                 870                 875                 880

Ala Thr Val Lys Ser Pro Asn Val Asn Tyr Asp Arg Ser Phe Lys Leu
            885                 890                 895

Pro Ile Asp Leu Gln Asn Ile Thr Thr Gln Val Asn Ala Leu Phe Ala
            900                 905                 910

Ser Gly Thr Gln Asn Met Leu Ala His Asn Val Ser Asp His Asp Ile
            915                 920                 925

Glu Glu Val Val Leu Lys Val Asp Ala Leu Ser Asp Glu Val Phe Gly
            930                 935                 940

Asp Glu Lys Lys Ala Leu Arg Lys Leu Val Asn Gln Ala Lys Arg Leu
945                 950                 955                 960

Ser Arg Ala Arg Asn Leu Leu Ile Gly Gly Ser Phe Glu Asn Trp Asp
            965                 970                 975

Ala Trp Tyr Lys Gly Arg Asn Val Val Thr Val Ser Asp His Glu Leu
            980                 985                 990

Phe Lys Ser Asp His Val Leu Leu Pro Pro Gly Leu Ser Pro Ser
            995                 1000                1005

Tyr Ile Phe Gln Lys Val Glu Glu Ser Lys Leu Lys Pro Asn Thr Arg
            1010                1015                1020

Tyr Ile Val Ser Gly Phe Ile Ala His Gly Lys Asp Leu Glu Ile Val
1025                1030                1035                1040

Val Ser Arg Tyr Gly Gln Glu Val Gln Lys Val Val Gln Val Pro Tyr
            1045                1050                1055

Gly Glu Ala Phe Pro Leu Thr Ser Asn Gly Pro Val Cys Cys Pro Pro
            1060                1065                1070

Arg Ser Thr Ser Asn Gly Thr Leu Gly Asp Pro His Phe Phe Ser Tyr
            1075                1080                1085

Ser Ile Asp Val Gly Ala Leu Asp Leu Gln Ala Asn Pro Gly Ile Glu
            1090                1095                1100

Phe Gly Leu Arg Ile Val Asn Pro Thr Gly Met Ala Arg Val Ser Asn
1105                1110                1115                1120

Leu Glu Ile Arg Glu Asp Arg Pro Leu Ala Ala Asn Glu Ile Arg Gln
            1125                1130                1135

Val Gln Arg Val Ala Arg Asn Trp Arg Thr Glu Tyr Glu Lys Glu Arg
            1140                1145                1150

Ala Glu Val Thr Ser Leu Ile Gln Pro Val Ile Asn Arg Ile Asn Gly
            1155                1160                1165

Leu Tyr Glu Asn Gly Asn Trp Asn Gly Ser Ile Arg Ser Asp Ile Ser
            1170                1175                1180

Tyr Gln Asn Ile Asp Ala Ile Val Leu Pro Thr Leu Pro Lys Leu Arg
1185                1190                1195                1200

His Trp Phe Met Ser Asp Arg Phe Ser Glu Gln Gly Asp Ile Met Ala
            1205                1210                1215

Lys Phe Gln Gly Ala Leu Asn Arg Ala Tyr Ala Gln Leu Glu Gln Ser
```

-continued

```
            1220                1225                1230

Thr Leu Leu His Asn Gly His Phe Thr Lys Asp Ala Ala Asn Trp Thr
        1235                1240                1245

Ile Glu Gly Asp Ala His Gln Ile Thr Leu Glu Asp Gly Arg Arg Val
    1250                1255                1260

Leu Arg Leu Pro Asp Trp Ser Ser Ser Val Ser Gln Met Ile Glu Ile
1265                1270                1275                1280

Glu Asn Phe Asn Pro Asp Lys Glu Tyr Asn Leu Val Phe His Gly Gln
                1285                1290                1295

Gly Glu Gly Thr Val Thr Leu Glu His Gly Glu Glu Thr Lys Tyr Ile
            1300                1305                1310

Glu Thr His Thr His His Phe Ala Asn Phe Thr Thr Ser Gln Arg Gln
        1315                1320                1325

Gly Leu Thr Phe Glu Ser Asn Lys Val Thr Val Thr Ile Ser Ser Glu
    1330                1335                1340

Asp Gly Glu Phe Leu Val Asp Asn Ile Ala Leu Val Glu Ala Pro Leu
1345                1350                1355                1360

Pro Thr Asp Asp Gln Asn Ser Glu Gly Asn Thr Ala Ser Ser Thr Asn
                1365                1370                1375

Ser Asp Thr Ser Met Asn Asn Asn Gln
            1380                1385
```

(2) INFORMATION FOR SEQ ID NO:3:

(i) SEQUENCE CHARACTERISTICS:
(A) LENGTH: 3867 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Bacillus thuringiensis
(B) STRAIN: PS17
(C) INDIVIDUAL ISOLATE: PS17b (vii) IMMEDIATE SOURCE:
(B) CLONE: E. coli NM522(pMYC1628) NRRL B-18652

(xi) SEQUENCE DESCRIPTION: SEQ ID NO:3:

```
ATGGCAATTT TAAATGAATT ATATCCATCT GTACCTTATA ATGTATTGGC GTATACGCCA     60

CCCTCTTTTT TACCTGATGC GGGTACACAA GCTACACCTG CTGACTTAAC AGCTTATGAA    120

CAATTGTTGA AAAATTTAGA AAAAGGGATA AATGCTGGAA CTTATTCGAA AGCAATAGCT    180

GATGTACTTA AAGGTATTTT TATAGATGAT ACAATAAATT ATCAAACATA TGTAAATATT    240

GGTTTAAGTT TAATTACATT AGCTGTACCG GAAATTGGTA TTTTTACACC TTTCATCGGT    300

TTGTTTTTTG CTGCATTGAA TAAACATGAT GCTCCACCTC CTCCTAATGC AAAAGATATA    360

TTTGAGGCTA TGAAACCAGC GATTCAAGAG ATGATTGATA GAACTTTAAC TGCGGATGAG    420

CAAACATTTT TAAATGGGGA AATAAGTGGT TTACAAAATT TAGCAGCAAG ATACCAGTCT    480

ACAATGGATG ATATTCAAAG CCATGGAGGA TTTAATAAGG TAGATTCTGG ATTAATTAAA    540

AAGTTTACAG ATGAGGTACT ATCTTTAAAT AGTTTTTATA CAGATCGTTT ACCTGTATTT    600

ATTACAGATA ATACAGCGGA TCGAACTTTG TTAGGTCTTC CTTATTATGC TATACTTGCG    660
```

```
-continued

AGCATGCATC TTATGTTATT AAGAGATATC ATTACTAAGG GTCCGACATG GGATTCTAAA      720

ATTAATTTCA CACCAGATGC AATTGATTCC TTTAAAACCG ATATTAAAAA TAATATAAAG      780

CTTTACTCTA AAACTATTTA TGACGTATTT CAGAAGGGAC TTGCTTCATA CGGAACGCCT      840

TCTGATTTAG AGTCCTTTGC AAAAAAACAA AAATATATTG AAATTATGAC AACACATTGT      900

TTAGATTTTG CAAGATTGTT TCCTACTTTT GATCCAGATC TTTATCCAAC AGGATCAGGT      960

GATATAAGTT TACAAAAAAC ACGTAGAATT CTTTCTCCTT TTATCCCTAT ACGTACTGCA     1020

GATGGGTTAA CATTAAATAA TACTTCAATT GATACTTCAA ATTGGCCTAA TTATGAAAAT     1080

GGGAATGGCG CGTTTCCAAA CCCAAAAGAA AGAATATTAA AACAATTCAA ACTGTATCCT     1140

AGTTGGAGAG CGGCACAGTA CGGTGGGCTT TTACAACCTT ATTTATGGGC AATAGAAGTC     1200

CAAGATTCTG TAGAGACTCG TTTGTATGGG CAGCTTCCAG CTGTAGATCC ACAGGCAGGG     1260

CCTAATTATG TTTCCATAGA TTCTTCTAAT CCAATCATAC AAATAAATAT GGATACTTGG     1320

AAAACACCAC CACAAGGTGC GAGTGGGTGG AATACAAATT TAATGAGAGG AAGTGTAAGC     1380

GGGTTAAGTT TTTTACAACG AGATGGTACG AGACTTAGTG CTGGTATGGG TGGTGGTTTT     1440

GCTGATACAA TATATAGTCT CCCTGCAACT CATTATCTTT CTTATCTCTA TGGAACTCCT     1500

TATCAAACTT CTGATAACTA TTCTGGTCAC GTTGGTGCAT TGGTAGGTGT GAGTACGCCT     1560

CAAGAGGCTA CTCTTCCTAA TATTATAGGT CAACCAGATG AACAGGGAAA TGTATCTACA     1620

ATGGGATTTC CGTTTGAAAA AGCTTCTTAT GGAGGTACAG TTGTTAAAGA ATGGTTAAAT     1680

GGTGCGAATG CGATGAAGCT TTCTCCTGGG CAATCTATAG GTATTCCTAT TACAAATGTA     1740

ACAAGTGGAG AATATCAAAT TCGTTGTCGT TATGCAAGTA ATGATAATAC TAACGTTTTC     1800

TTTAATGTAG ATACTGGTGG AGCAAATCCA ATTTTCCAAC AGATAAACTT TGCATCTACT     1860

GTAGATAATA ATACGGGAGT ACAAGGAGCA AATGGTGTCT ATGTAGTCAA ATCTATTGCT     1920

ACAACTGATA ATTCTTTTAC AGTAAAAATT CCTGCGAAGA CGATTAATGT TCATTTAACC     1980

AACCAAGGTT CTTCTGATGT CTTTTTAGAT CGTATTGAGT TTGTTCCAAT TCTAGAATCA     2040

AATACTGTAA CTATATTCAA CAATTCATAT ACTACAGGTT CAGCAAATCT TATACCAGCA     2100

ATAGCTCCTC TTTGGAGTAC TAGTTCAGAT AAAGCCCTTA CAGGTTCTAT GTCAATAACA     2160

GGTCGAACTA CCCCTAACAG TGATGATGCT TTGCTTCGAT TTTTTAAAAC TAATTATGAT     2220

ACACAAACCA TTCCTATTCC GGGTTCCGGA AAAGATTTTA CAAATACTCT AGAAATACAA     2280

GACATAGTTT CTATTGATAT TTTTGTCGGA TCTGGTCTAC ATGGATCCGA TGGATCTATA     2340

AAATTAGATT TTACCAATAA TAATAGTGGT AGTGGTGGCT CTCCAAAGAG TTTCACCGAG     2400

CAAAATGATT TAGAGAATAT CACAACACAA GTGAATGCTC TATTCACATC TAATACACAA     2460

GATGCACTTG CAACAGATGT GAGTGATCAT GATATTGAAG AAGTGGTTCT AAAAGTAGAT     2520

GCATTATCTG ATGAAGTGTT TGGAAAAGAG AAAAAAACAT TGCGTAAATT TGTAAATCAA     2580

GCGAAGCGCT TAAGCAAGGC GCGTAATCTC CTGGTAGGAG GCAATTTTGA TAACTTGGAT     2640

GCTTGGTATA GAGGAAGAAA TGTAGTAAAC GTATCTAATC ACGAACTGTT GAAGAGTGAT     2700

CATGTATTAT TACCACCACC AGGATTGTCT CCATCTTATA TTTTCCAAAA AGTGGAGGAA     2760

TCTAAATTAA AACGAAATAC ACGTTATACG GTTTCTGGAT TTATTGCGCA TGCAACAGAT     2820

TTAGAAATTG TGGTTTCTCG TTATGGGCAA GAAATAAAGA AAGTGGTGCA AGTTCCTTAT     2880

GGAGAAGCAT TCCCATTAAC ATCAAGTGGA CCAGTTTGTT GTATCCCACA TTCTACAAGT     2940

AATGGAACTT TAGGCAATCC ACATTTCTTT AGTTACAGTA TTGATGTAGG TGCATTAGAT     3000

GTAGACACAA ACCCTGGTAT TGAATTCGGT CTTCGTATTG TAAATCCAAC TGGAATGGCA     3060
```

-continued

```
CGCGTAAGCA AATTTGGAAAT TCGTGAAGAT CGTCCATTAG CAGCAAATGA AATACGACAA    3120

GTACAACGTG TCGCAAGAAA TTGGAGAACC GAGTATGAGA AGAACGTGC GGAAGTAACA     3180

AGTTTAATTC AACCTGTTAT CAATCGAATC AATGGATTGT ATGACAATGG AAATTGGAAC    3240

GGTTCTATTC GTTCAGATAT TTCGTATCAG AATATAGACG CGATTGTATT ACCAACGTTA    3300

CCAAAGTTAC GCCATTGGTT TATGTCAGAT AGATTTAGTG AACAAGGAGA TATCATGGCT    3360

AAATTCCAAG GTGCATTAAA TCGTGCGTAT GCACAACTGG AACAAAATAC GCTTCTGCAT    3420

AATGGTCATT TTACAAAAGA TGCAGCCAAT TGGACGGTAG AAGGCGATGC ACATCAGGTA    3480

GTATTAGAAG ATGGTAAACG TGTATTACGA TTGCCAGATT GGTCTTCGAG TGTGTCTCAA    3540

ACGATTGAAA TCGAGAATTT TGATCCAGAT AAAGAATATA AATTAGTATT TCATGGGCAA    3600

GGAGAAGGAA CGGTTACGTT GGAGCATGGA GAAGAAACAA AATATATAGA AACGCATACA    3660

CATCATTTTG CGAATTTTAC AACTTCTCAA CGTCAAGGAC TCACGTTTGA ATCAAATAAA    3720

GTGACAGTGA CCATTTCTTC AGAAGATGGA GAATTCTTAG TGGATAATAT TGCGCTTGTG    3780

GAAGCTCCTC TTCCTACAGA TGACCAAAAT TCTGAGGGAA ATACGGCTTC CAGTACGAAT    3840

AGCGATACAA GTATGAACAA CAATCAA                                        3867
```

(2) INFORMATION FOR SEQ ID NO:4:

(i) SEQUENCE CHARACTERISTICS:
    (A) LENGTH: 1289 amino acids
    (B) TYPE: amino acid
    (C) STRANDEDNESS: single
    (D) TOPOLOGY: linear (ii) MOLECULE TYPE: protein (iii) HYPOTHETICAL: YES (iv) ANTI-SENSE: NO (vi) ORIGINAL SOURCE:
    (A) ORGANISM: BACILLUS THURINGIENSIS
    (B) STRAIN: PS17
(C) INDIVIDUAL ISOLATE: PS17b (vii) IMMEDIATE SOURCE:
(B) CLONE: E. coli NM522(pMYC1628) NRRL B-18652

(xi) SEQUENCE DESCRIPTION: SEQ ID NO:4:

```
Met Ala Ile Leu Asn Glu Leu Tyr Pro Ser Val Pro Tyr Asn Val Leu
1               5                   10                  15

Ala Tyr Thr Pro Pro Ser Phe Leu Pro Asp Ala Gly Thr Gln Ala Thr
            20                  25                  30

Pro Ala Asp Leu Thr Ala Tyr Glu Gln Leu Leu Lys Asn Leu Glu Lys
        35                  40                  45

Gly Ile Asn Ala Gly Thr Tyr Ser Lys Ala Ile Ala Asp Val Leu Lys
    50                  55                  60

Gly Ile Phe Ile Asp Asp Thr Ile Asn Tyr Gln Thr Tyr Val Asn Ile
65                  70                  75                  80

Gly Leu Ser Leu Ile Thr Leu Ala Val Pro Glu Ile Gly Ile Phe Thr
                85                  90                  95

Pro Phe Ile Gly Leu Phe Phe Ala Ala Leu Asn Lys His Asp Ala Pro
            100                 105                 110

Pro Pro Pro Asn Ala Lys Asp Ile Phe Glu Ala Met Lys Pro Ala Ile
        115                 120                 125

Gln Glu Met Ile Asp Arg Thr Leu Thr Ala Asp Glu Gln Thr Phe Leu
```

-continued

```
            130                 135                 140
Asn Gly Glu Ile Ser Gly Leu Gln Asn Leu Ala Ala Arg Tyr Gln Ser
145                 150                 155                 160
Thr Met Asp Asp Ile Gln Ser His Gly Gly Phe Asn Lys Val Asp Ser
                165                 170                 175
Gly Leu Ile Lys Lys Phe Thr Asp Glu Val Leu Ser Leu Asn Ser Phe
                180                 185                 190
Tyr Thr Asp Arg Leu Pro Val Phe Ile Thr Asp Asn Thr Ala Asp Arg
                195                 200                 205
Thr Leu Leu Gly Leu Pro Tyr Tyr Ala Ile Leu Ala Ser Met His Leu
            210                 215                 220
Met Leu Leu Arg Asp Ile Ile Thr Lys Gly Pro Thr Trp Asp Ser Lys
225                 230                 235                 240
Ile Asn Phe Thr Pro Asp Ala Ile Asp Ser Phe Lys Thr Asp Ile Lys
                245                 250                 255
Asn Asn Ile Lys Leu Tyr Ser Lys Thr Ile Tyr Asp Val Phe Gln Lys
                260                 265                 270
Gly Leu Ala Ser Tyr Gly Thr Pro Ser Asp Leu Glu Ser Phe Ala Lys
            275                 280                 285
Lys Gln Lys Tyr Ile Glu Ile Met Thr Thr His Cys Leu Asp Phe Ala
290                 295                 300
Arg Leu Phe Pro Thr Phe Asp Pro Asp Leu Tyr Pro Thr Gly Ser Gly
305                 310                 315                 320
Asp Ile Ser Leu Gln Lys Thr Arg Arg Ile Leu Ser Pro Phe Ile Pro
                325                 330                 335
Ile Arg Thr Ala Asp Gly Leu Thr Leu Asn Asn Thr Ser Ile Asp Thr
                340                 345                 350
Ser Asn Trp Pro Asn Tyr Glu Asn Gly Asn Gly Ala Phe Pro Asn Pro
                355                 360                 365
Lys Glu Arg Ile Leu Lys Gln Phe Lys Leu Tyr Pro Ser Trp Arg Ala
            370                 375                 380
Ala Gln Tyr Gly Gly Leu Leu Gln Pro Tyr Leu Trp Ala Ile Glu Val
385                 390                 395                 400
Gln Asp Ser Val Glu Thr Arg Leu Tyr Gly Gln Leu Pro Ala Val Asp
                405                 410                 415
Pro Gln Ala Gly Pro Asn Tyr Val Ser Ile Asp Ser Ser Asn Pro Ile
                420                 425                 430
Ile Gln Ile Asn Met Asp Thr Trp Lys Thr Pro Pro Gln Gly Ala Ser
            435                 440                 445
Gly Trp Asn Thr Asn Leu Met Arg Gly Ser Val Ser Gly Leu Ser Phe
            450                 455                 460
Leu Gln Arg Asp Gly Thr Arg Leu Ser Ala Gly Met Gly Gly Gly Phe
465                 470                 475                 480
Ala Asp Thr Ile Tyr Ser Leu Pro Ala Thr His Tyr Leu Ser Tyr Leu
                485                 490                 495
Tyr Gly Thr Pro Tyr Gln Thr Ser Asp Asn Tyr Ser Gly His Val Gly
                500                 505                 510
Ala Leu Val Gly Val Ser Thr Pro Gln Glu Ala Thr Leu Pro Asn Ile
            515                 520                 525
Ile Gly Gln Pro Asp Glu Gln Gly Asn Val Ser Thr Met Gly Phe Pro
            530                 535                 540
Phe Glu Lys Ala Ser Tyr Gly Gly Thr Val Val Lys Glu Trp Leu Asn
545                 550                 555                 560
```

-continued

```
Gly Ala Asn Ala Met Lys Leu Ser Pro Gly Gln Ser Ile Gly Ile Pro
                565                 570                 575
Ile Thr Asn Val Thr Ser Gly Glu Tyr Gln Ile Arg Cys Arg Tyr Ala
            580                 585                 590
Ser Asn Asp Asn Thr Asn Val Phe Phe Asn Val Asp Thr Gly Gly Ala
        595                 600                 605
Asn Pro Ile Phe Gln Gln Ile Asn Phe Ala Ser Thr Val Asp Asn Asn
    610                 615                 620
Thr Gly Val Gln Gly Ala Asn Gly Val Tyr Val Val Lys Ser Ile Ala
625                 630                 635                 640
Thr Thr Asp Asn Ser Phe Thr Val Lys Ile Pro Ala Lys Thr Ile Asn
                645                 650                 655
Val His Leu Thr Asn Gln Gly Ser Ser Asp Val Phe Leu Asp Arg Ile
            660                 665                 670
Glu Phe Val Pro Ile Leu Glu Ser Asn Thr Val Thr Ile Phe Asn Asn
        675                 680                 685
Ser Tyr Thr Thr Gly Ser Ala Asn Leu Ile Pro Ala Ile Ala Pro Leu
    690                 695                 700
Trp Ser Thr Ser Ser Asp Lys Ala Leu Thr Gly Ser Met Ser Ile Thr
705                 710                 715                 720
Gly Arg Thr Thr Pro Asn Ser Asp Asp Ala Leu Leu Arg Phe Phe Lys
                725                 730                 735
Thr Asn Tyr Asp Thr Gln Thr Ile Pro Ile Pro Gly Ser Gly Lys Asp
            740                 745                 750
Phe Thr Asn Thr Leu Glu Ile Gln Asp Ile Val Ser Ile Asp Ile Phe
        755                 760                 765
Val Gly Ser Gly Leu His Gly Ser Asp Gly Ser Ile Lys Leu Asp Phe
    770                 775                 780
Thr Asn Asn Asn Ser Gly Ser Gly Ser Pro Lys Ser Phe Thr Glu
785                 790                 795                 800
Gln Asn Asp Leu Glu Asn Ile Thr Thr Gln Val Asn Ala Leu Phe Thr
                805                 810                 815
Ser Asn Thr Gln Asp Ala Leu Ala Thr Asp Val Ser Asp His Asp Ile
            820                 825                 830
Glu Glu Val Val Leu Lys Val Asp Ala Leu Ser Asp Glu Val Phe Gly
        835                 840                 845
Lys Glu Lys Lys Thr Leu Arg Lys Phe Val Asn Gln Ala Lys Arg Leu
    850                 855                 860
Ser Lys Ala Arg Asn Leu Leu Val Gly Gly Asn Phe Asp Asn Leu Asp
865                 870                 875                 880
Ala Trp Tyr Arg Gly Arg Asn Val Val Asn Val Ser Asn His Glu Leu
                885                 890                 895
Leu Lys Ser Asp His Val Leu Leu Pro Pro Gly Leu Ser Pro Ser
            900                 905                 910
Tyr Ile Phe Gln Lys Val Glu Glu Ser Lys Leu Lys Arg Asn Thr Arg
        915                 920                 925
Tyr Thr Val Ser Gly Phe Ile Ala His Ala Thr Asp Leu Glu Ile Val
    930                 935                 940
Val Ser Arg Tyr Gly Gln Glu Ile Lys Lys Val Val Gln Val Pro Tyr
945                 950                 955                 960
Gly Glu Ala Phe Pro Leu Thr Ser Ser Gly Pro Val Cys Cys Ile Pro
                965                 970                 975
```

His Ser Thr Ser Asn Gly Thr Leu Gly Asn Pro His Phe Phe Ser Tyr
            980             985             990

Ser Ile Asp Val Gly Ala Leu Asp Val Asp Thr Asn Pro Gly Ile Glu
        995             1000            1005

Phe Gly Leu Arg Ile Val Asn Pro Thr Gly Met Ala Arg Val Ser Asn
    1010            1015            1020

Leu Glu Ile Arg Glu Asp Arg Pro Leu Ala Ala Asn Glu Ile Arg Gln
1025            1030            1035            1040

Val Gln Arg Val Ala Arg Asn Trp Arg Thr Glu Tyr Glu Lys Glu Arg
            1045            1050            1055

Ala Glu Val Thr Ser Leu Ile Gln Pro Val Ile Asn Arg Ile Asn Gly
        1060            1065            1070

Leu Tyr Asp Asn Gly Asn Trp Asn Gly Ser Ile Arg Ser Asp Ile Ser
    1075            1080            1085

Tyr Gln Asn Ile Asp Ala Ile Val Leu Pro Thr Leu Pro Lys Leu Arg
1090            1095            1100

His Trp Phe Met Ser Asp Arg Phe Ser Glu Gln Gly Asp Ile Met Ala
1105            1110            1115            1120

Lys Phe Gln Gly Ala Leu Asn Arg Ala Tyr Ala Gln Leu Glu Gln Asn
            1125            1130            1135

Thr Leu Leu His Asn Gly His Phe Thr Lys Asp Ala Ala Asn Trp Thr
        1140            1145            1150

Val Glu Gly Asp Ala His Gln Val Val Leu Glu Asp Gly Lys Arg Val
    1155            1160            1165

Leu Arg Leu Pro Asp Trp Ser Ser Ser Val Ser Gln Thr Ile Glu Ile
    1170            1175            1180

Glu Asn Phe Asp Pro Asp Lys Glu Tyr Gln Leu Val Phe His Gly Gln
1185            1190            1195            1200

Gly Glu Gly Thr Val Thr Leu Glu His Gly Glu Glu Thr Lys Tyr Ile
            1205            1210            1215

Glu Thr His Thr His His Phe Ala Asn Phe Thr Thr Ser Gln Arg Gln
        1220            1225            1230

Gly Leu Thr Phe Glu Ser Asn Lys Val Thr Val Thr Ile Ser Ser Glu
    1235            1240            1245

Asp Gly Glu Phe Leu Val Asp Asn Ile Ala Leu Val Glu Ala Pro Leu
    1250            1255            1260

Pro Thr Asp Asp Gln Asn Ser Glu Gly Asn Thr Ala Ser Ser Thr Asn
1265            1270            1275            1280

Ser Asp Thr Ser Met Asn Asn Asn Gln
            1285

(2) INFORMATION FOR SEQ ID NO:5:

(i) SEQUENCE CHARACTERISTICS:
        (A) LENGTH: 3771 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus thuringiensis
        (C) INDIVIDUAL ISOLATE: 33F2

(vii) IMMEDIATE SOURCE:
    (B) CLONE: E. coli NM522(pMYC2316) B-18785

(ix) FEATURE:
    (A) NAME/KEY: misc_feature
    (B) LOCATION: 4..24
    (D) OTHER INFORMATION: /function= "oligonucleotide
        hybridization probe"
        /product= "GCA/T ACA/T TTA AAT GAA GTA/T TAT"
        /standard_name= "probe a"
        /note= "Probe A"

(ix) FEATURE:
    (A) NAME/KEY: misc_feature
    (B) LOCATION: 13..33
    (D) OTHER INFORMATION: /function= "oligonucleotide
        hybridization probe"
        /product= "AAT GAA GTA/T TAT CCA/T GTA/T AAT"
        /standard_name= "Probe B"
        /label= probe-b
        /note= "probe b"

(xi) SEQUENCE DESCRIPTION: SEQ ID NO:5:

```
ATGGCTACAC TTAATGAAGT ATATCCTGTG AATTATAATG TATTATCTTC TGATGCTTTT     60

CAACAATTAG ATACAACAGG TTTTAAAAGT AAATATGATG AAATGATAAA AGCATTCGAA    120

AAAAAATGGA AAAAGGGGC AAAAGGAAAA GACCTTTTAG ATGTTGCATG GACTTATATA    180

ACTACAGGAG AAATTGACCC TTTAAATGTA ATTAAAGGTG TTTTATCTGT ATTAACTTTA    240

ATTCCTGAAG TTGGTACTGT GGCCTCTGCA GCAAGTACTA TTGTAAGTTT TATTTGGCCT    300

AAAATATTTG GAGATAAACC AAATGCAAAA AATATATTTG AAGAGCTCAA GCCTCAAATT    360

GAAGCATTAA TTCAACAAGA TATAACAAAC TATCAAGATG CAATTAATCA AAAAAAATTT    420

GACAGTCTTC AGAAAACAAT TAATCTATAT ACAGTAGCTA TAGATAACAA TGATTACGTA    480

ACAGCAAAAA CGCAACTCGA AAATCTAAAT TCTATACTTA CCTCAGATAT CTCCATATTT    540

ATTCCAGAAG GATATGAAAC TGGAGGTTTA CCTTATTATG CTATGGTTGC TAATGCTCAT    600

ATATTATTGT TAAGAGACGC TATAGTTAAT GCAGAGAAAT TAGGCTTTAG TGATAAAGAA    660

GTAGACACAC ATAAAAAATA TATCAAAATG ACAATACACA ATCATACTGA AGCAGTAATA    720

AAAGCATTCT TAAATGGACT TGACAAATTT AAGAGTTTAG ATGTAAATAG CTATAATAAA    780

AAAGCAAATT ATATTAAAGG TATGACAGAA ATGGTTCTTG ATCTAGTTGC TCTATGGCCA    840

ACTTTCGATC CAGATCATTA TCAAAAAGAA GTAGAAATTG AATTTACAAG AACTATTTCT    900

TCTCCAATTT ACCAACCTGT ACCTAAAAAC ATGCAAAATA CCTCTAGCTC TATTGTACCT    960

AGCGATCTAT TTCACTATCA AGGAGATCTT GTAAAATTAG AATTTTCTAC AAGAACGGAC   1020

AACGATGGTC TTGCAAAAAT TTTTACTGGT ATTCGAAACA CATTCTACAA ATCGCCTAAT   1080

ACTCATGAAA CATACCATGT AGATTTTAGT TATAATACCC AATCTAGTGG TAATATTTCA   1140

AGAGGCTCTT CAAATCCGAT TCCAATTGAT CTTAATAATC CCATTATTTC AACTTGTATT   1200

AGAAATTCAT TTTATAAGGC AATAGCGGGA TCTTCTGTTT TAGTTAATTT TAAAGATGGC   1260

ACTCAAGGGT ATGCATTTGC CCAAGCACCA ACAGGAGGTG CCTGGGACCA TTCTTTTATT   1320

GAATCTGATG GTGCCCCAGA AGGGCATAAA TTAAACTATA TTTATACTTC TCCAGGTGAT   1380

ACATTAAGAG ATTTCATCAA TGTATATACT CTTATAAGTA CTCCAACTAT AAATGAACTA   1440

TCAACAGAAA AAATCAAAGG CTTTCCTGCG GAAAAGGAT ATATCAAAAA TCAAGGGATC   1500

ATGAAATATT ACGGTAAACC AGAATATATT AATGGAGCTC AACCAGTTAA TCTGGAAAAC   1560

CAGCAAACAT TAATATTCGA ATTTCATGCT TCAAAAACAG CTCAATATAC CATTCGTATA   1620

CGTTATGCCA GTACCCAAGG AACAAAAGGT TATTTTCGTT TAGATAATCA GGAACTGCAA   1680
```

```
ACGCTTAATA TACCTACTTC ACACAACGGT TATGTAACCG GTAATATTGG TGAAAATTAT    1740

GATTTATATA CAATAGGTTC ATATACAATT ACAGAAGGTA ACCATACTCT TCAAATCCAA    1800

CATAATGATA AAAATGGAAT GGTTTTAGAT CGTATTGAAT TTGTTCCTAA AGATTCACTT    1860

CAAGATTCAC CTCAAGATTC ACCTCCAGAA GTTCACGAAT CAACAATTAT TTTTGATAAA    1920

TCATCTCCAA CTATATGGTC TTCTAACAAA CACTCATATA GCCATATACA TTTAGAAGGA    1980

TCATATACAA GTCAGGGAAG TTATCCACAC AATTTATTAA TTAATTTATT TCATCCTACA    2040

GACCCTAACA GAAATCATAC TATTCATGTT AACAATGGTG ATATGAATGT TGATTATGGA    2100

AAAGATTCTG TAGCCGATGG GTTAAATTTT AATAAAATAA CTGCTACGAT ACCAAGTGAT    2160

GCTTGGTATA GCGGTACTAT TACTTCTATG CACTTATTTA ATGATAATAA TTTTAAAACA    2220

ATAACTCCTA AATTTGAACT TTCTAATGAA TTAGAAAACA TCACAACTCA AGTAAATGCT    2280

TTATTCGCAT CTAGTGCACA AGATACTCTC GCAAGTAATG TAAGTGATTA CTGGATTGAA    2340

CAGGTCGTTA TGAAAGTCGA TGCCTTATCA GATGAAGTAT TTGGAAAAGA GAAAAAAGCA    2400

TTACGTAAAT TGGTAAATCA AGCAAAACGT CTCAGTAAAA TACGAAATCT TCTCATAGGT    2460

GGTAATTTTG ACAATTTAGT CGCTTGGTAT ATGGGAAAAG ATGTAGTAAA AGAATCGGAT    2520

CATGAATTAT TTAAAAGTGA TCATGTCTTA CTACCTCCCC CAACATTCCA TCCTTCTTAT    2580

ATTTTCCAAA AGGTGGAAGA ATCAAAACTA AAACCAAATA CACGTTATAC TATTTCTGGT    2640

TTTATCGCAC ATGGAGAAGA TGTAGAGCTT GTTGTCTCTC GTTATGGGCA AGAAATACAA    2700

AAAGTGATGC AAGTGCCATA TGAAGAAGCA CTTCCTCTTA CATCTGAATC TAATTCTAGT    2760

TGTTGTGTTC CAAATTTAAA TATAAATGAA ACACTAGCTG ATCCACATTT CTTTAGTTAT    2820

AGCATCGATG TTGGTTCTCT GGAAATGGAA GCGAATCCTG GTATTGAATT TGGTCTCCGT    2880

ATTGTCAAAC CAACAGGTAT GGCACGTGTA AGTAATTTAG AAATTCGAGA AGACCGTCCA    2940

TTAACAGCAA AAGAAATTCG TCAAGTACAA CGTGCAGCAA GAGATTGGAA ACAAAACTAT    3000

GAACAAGAAC GAACAGAGAT CACAGCTATA ATTCAACCTG TTCTTAATCA AATTAATGCG    3060

TTATACGAAA ATGAAGATTG GAATGGTTCT ATTCGTTCAA ATGTTTCCTA TCATGATCTA    3120

GAGCAAATTA TGCTTCCTAC TTTATTAAAA ACTGAGGAAA TAAATTGTAA TTATGATCAT    3180

CCAGCTTTTT TATTAAAAGT ATATCATTGG TTTATGACAG ATCGTATAGG AGAACATGGT    3240

ACTATTTTAG CACGTTTCCA AGAAGCATTA GATCGTGCAT ATACACAATT AGAAAGTCGT    3300

AATCTCCTGC ATAACGGTCA TTTTACAACT GATACAGCGA ATTGGACAAT AGAAGGAGAT    3360

GCCCATCATA CAATCTTAGA AGATGGTAGA CGTGTGTTAC GTTACCAGA TTGGTCTTCT    3420

AATGCAACTC AAACAATTGA AATTGAAGAT TTTGACTTAG ATCAAGAATA CCAATTGCTC    3480

ATTCATGCAA AAGGAAAAGG TTCCATTACT TTACAACATG GAGAAGAAAA CGAATATGTG    3540

GAAACACATA CTCATCATAC AAATGATTTT ATAACATCCC AAAATATTCC TTTCACTTTT    3600

AAAGGAAATC AAATTGAAGT CCATATTACT TCAGAAGATG GAGAGTTTTT AATCGATCAC    3660

ATTACAGTAA TAGAAGTTTC TAAAACAGAC ACAAATACAA ATATTATTGA AAATTCACCA    3720

ATCAATACAA GTATGAATAG TAATGTAAGA GTAGATATAC CAAGAAGTCT C           3771
```

(2) INFORMATION FOR SEQ ID NO:6:

(i) SEQUENCE CHARACTERISTICS:
        (A) LENGTH: 1257 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
    (A) ORGANISM: Bacillus thuringiensis
    (C) INDIVIDUAL ISOLATE: PS33F2

(vii) IMMEDIATE SOURCE:
    (B) CLONE: E. coli NM522(pMYC2316) B-18785

(ix) FEATURE:
    (A) NAME/KEY: Protein
    (B) LOCATION: 1..1257

(xi) SEQUENCE DESCRIPTION: SEQ ID NO:6:

```
Met Ala Thr Leu Asn Glu Val Tyr Pro Val Asn Tyr Asn Val Leu Ser
1               5                   10                  15

Ser Asp Ala Phe Gln Gln Leu Asp Thr Thr Gly Phe Lys Ser Lys Tyr
            20                  25                  30

Asp Glu Met Ile Lys Ala Phe Glu Lys Lys Trp Lys Lys Gly Ala Lys
        35                  40                  45

Gly Lys Asp Leu Leu Asp Val Ala Trp Thr Tyr Ile Thr Thr Gly Glu
50                  55                  60

Ile Asp Pro Leu Asn Val Ile Lys Gly Val Leu Ser Val Leu Thr Leu
65                  70                  75                  80

Ile Pro Glu Val Gly Thr Val Ala Ser Ala Ala Ser Thr Ile Val Ser
                85                  90                  95

Phe Ile Trp Pro Lys Ile Phe Gly Asp Lys Pro Asn Ala Lys Asn Ile
            100                 105                 110

Phe Glu Glu Leu Lys Pro Gln Ile Glu Ala Leu Ile Gln Gln Asp Ile
        115                 120                 125

Thr Asn Tyr Gln Asp Ala Ile Asn Gln Lys Lys Phe Asp Ser Leu Gln
130                 135                 140

Lys Thr Ile Asn Leu Tyr Thr Val Ala Ile Asp Asn Asn Asp Tyr Val
145                 150                 155                 160

Thr Ala Lys Thr Gln Leu Glu Asn Leu Asn Ser Ile Leu Thr Ser Asp
                165                 170                 175

Ile Ser Ile Phe Ile Pro Glu Gly Tyr Glu Thr Gly Gly Leu Pro Tyr
            180                 185                 190

Tyr Ala Met Val Ala Asn Ala His Ile Leu Leu Leu Arg Asp Ala Ile
        195                 200                 205

Val Asn Ala Glu Lys Leu Gly Phe Ser Asp Lys Glu Val Asp Thr His
210                 215                 220

Lys Lys Tyr Ile Lys Met Thr Ile His Asn His Thr Glu Ala Val Ile
225                 230                 235                 240

Lys Ala Phe Leu Asn Gly Leu Asp Lys Phe Lys Ser Leu Asp Val Asn
                245                 250                 255

Ser Tyr Asn Lys Lys Ala Asn Tyr Ile Lys Gly Met Thr Glu Met Val
            260                 265                 270

Leu Asp Leu Val Ala Leu Trp Pro Thr Phe Asp Pro Asp His Tyr Gln
        275                 280                 285

Lys Glu Val Glu Ile Glu Phe Thr Arg Thr Ile Ser Ser Pro Ile Tyr
        290                 295                 300

Gln Pro Val Pro Lys Asn Met Gln Asn Thr Ser Ser Ile Val Pro
305                 310                 315                 320
```

```
Ser Asp Leu Phe His Tyr Gln Gly Asp Leu Val Lys Leu Glu Phe Ser
                325                 330                 335

Thr Arg Thr Asp Asn Asp Gly Leu Ala Lys Ile Phe Thr Gly Ile Arg
            340                 345                 350

Asn Thr Phe Tyr Lys Ser Pro Asn Thr His Glu Thr Tyr His Val Asp
                355                 360                 365

Phe Ser Tyr Asn Thr Gln Ser Ser Gly Asn Ile Ser Arg Gly Ser Ser
            370                 375                 380

Asn Pro Ile Pro Ile Asp Leu Asn Asn Pro Ile Ile Ser Thr Cys Ile
385                 390                 395                 400

Arg Asn Ser Phe Tyr Lys Ala Ile Ala Gly Ser Ser Val Leu Val Asn
                405                 410                 415

Phe Lys Asp Gly Thr Gln Gly Tyr Ala Phe Ala Gln Ala Pro Thr Gly
            420                 425                 430

Gly Ala Trp Asp His Ser Phe Ile Glu Ser Asp Gly Ala Pro Glu Gly
                435                 440                 445

His Lys Leu Asn Tyr Ile Tyr Thr Ser Pro Gly Asp Thr Leu Arg Asp
            450                 455                 460

Phe Ile Asn Val Tyr Thr Leu Ile Ser Thr Pro Thr Ile Asn Glu Leu
465                 470                 475                 480

Ser Thr Glu Lys Ile Lys Gly Phe Pro Ala Glu Lys Gly Tyr Ile Lys
                485                 490                 495

Asn Gln Gly Ile Met Lys Tyr Tyr Gly Lys Pro Glu Tyr Ile Asn Gly
            500                 505                 510

Ala Gln Pro Val Asn Leu Glu Asn Gln Gln Thr Leu Ile Phe Glu Phe
            515                 520                 525

His Ala Ser Lys Thr Ala Gln Tyr Thr Ile Arg Ile Arg Tyr Ala Ser
            530                 535                 540

Thr Gln Gly Thr Lys Gly Tyr Phe Arg Leu Asp Asn Gln Glu Leu Gln
545                 550                 555                 560

Thr Leu Asn Ile Pro Thr Ser His Asn Gly Tyr Val Thr Gly Asn Ile
                565                 570                 575

Gly Glu Asn Tyr Asp Leu Tyr Thr Ile Gly Ser Tyr Thr Ile Thr Glu
            580                 585                 590

Gly Asn His Thr Leu Gln Ile Gln His Asn Asp Lys Asn Gly Met Val
            595                 600                 605

Leu Asp Arg Ile Glu Phe Val Pro Lys Asp Ser Leu Gln Asp Ser Pro
            610                 615                 620

Gln Asp Ser Pro Pro Glu Val His Glu Ser Thr Ile Ile Phe Asp Lys
625                 630                 635                 640

Ser Ser Pro Thr Ile Trp Ser Ser Asn Lys His Ser Tyr Ser His Ile
                645                 650                 655

His Leu Glu Gly Ser Tyr Thr Ser Gln Gly Ser Tyr Pro His Asn Leu
            660                 665                 670

Leu Ile Asn Leu Phe His Pro Thr Asp Pro Asn Arg Asn His Thr Ile
            675                 680                 685

His Val Asn Asn Gly Asp Met Asn Val Asp Tyr Gly Lys Asp Ser Val
690                 695                 700

Ala Asp Gly Leu Asn Phe Asn Lys Ile Thr Ala Thr Ile Pro Ser Asp
705                 710                 715                 720

Ala Trp Tyr Ser Gly Thr Ile Thr Ser Met His Leu Phe Asn Asp Asn
                725                 730                 735
```

-continued

```
Asn Phe Lys Thr Ile Thr Pro Lys Phe Glu Leu Ser Asn Glu Leu Glu
        740                 745                 750

Asn Ile Thr Thr Gln Val Asn Ala Leu Phe Ala Ser Ser Ala Gln Asp
        755                 760                 765

Thr Leu Ala Ser Asn Val Ser Asp Tyr Trp Ile Glu Gln Val Val Met
770                 775                 780

Lys Val Asp Ala Leu Ser Asp Glu Val Phe Gly Lys Glu Lys Lys Ala
785                 790                 795                 800

Leu Arg Lys Leu Val Asn Gln Ala Lys Arg Leu Ser Lys Ile Arg Asn
                    805                 810                 815

Leu Leu Ile Gly Gly Asn Phe Asp Asn Leu Val Ala Trp Tyr Met Gly
                    820                 825                 830

Lys Asp Val Val Lys Glu Ser Asp His Glu Leu Phe Lys Ser Asp His
                    835                 840                 845

Val Leu Leu Pro Pro Pro Thr Phe His Pro Ser Tyr Ile Phe Gln Lys
850                 855                 860

Val Glu Glu Ser Lys Leu Lys Pro Asn Thr Arg Tyr Thr Ile Ser Gly
865                 870                 875                 880

Phe Ile Ala His Gly Glu Asp Val Glu Leu Val Val Ser Arg Tyr Gly
                    885                 890                 895

Gln Glu Ile Gln Lys Val Met Gln Val Pro Tyr Glu Glu Ala Leu Pro
                    900                 905                 910

Leu Thr Ser Glu Ser Asn Ser Ser Cys Cys Val Pro Asn Leu Asn Ile
                    915                 920                 925

Asn Glu Thr Leu Ala Asp Pro His Phe Phe Ser Tyr Ser Ile Asp Val
                    930                 935                 940

Gly Ser Leu Glu Met Glu Ala Asn Pro Gly Ile Glu Phe Gly Leu Arg
945                 950                 955                 960

Ile Val Lys Pro Thr Gly Met Ala Arg Val Ser Asn Leu Glu Ile Arg
                    965                 970                 975

Glu Asp Arg Pro Leu Thr Ala Lys Glu Ile Arg Gln Val Gln Arg Ala
                    980                 985                 990

Ala Arg Asp Trp Lys Gln Asn Tyr Glu Gln Glu Arg Thr Glu Ile Thr
                    995                 1000                1005

Ala Ile Ile Gln Pro Val Leu Asn Gln Ile Asn Ala Leu Tyr Glu Asn
        1010                1015                1020

Glu Asp Trp Asn Gly Ser Ile Arg Ser Asn Val Ser Tyr His Asp Leu
1025                1030                1035                1040

Glu Gln Ile Met Leu Pro Thr Leu Leu Lys Thr Glu Glu Ile Asn Cys
                    1045                1050                1055

Asn Tyr Asp His Pro Ala Phe Leu Leu Lys Val Tyr His Trp Phe Met
                    1060                1065                1070

Thr Asp Arg Ile Gly Glu His Gly Thr Ile Leu Ala Arg Phe Gln Glu
                    1075                1080                1085

Ala Leu Asp Arg Ala Tyr Thr Gln Leu Glu Ser Arg Asn Leu Leu His
        1090                1095                1100

Asn Gly His Phe Thr Thr Asp Thr Ala Asn Trp Thr Ile Glu Gly Asp
1105                1110                1115                1120

Ala His His Thr Ile Leu Glu Asp Gly Arg Arg Val Leu Arg Leu Pro
                    1125                1130                1135

Asp Trp Ser Ser Asn Ala Thr Gln Thr Ile Glu Ile Glu Asp Phe Asp
                    1140                1145                1150

Leu Asp Gln Glu Tyr Gln Leu Leu Ile His Ala Lys Gly Lys Gly Ser
```

-continued

```
        1155                1160                1165

Ile Thr Leu Gln His Gly Glu Glu Asn Glu Tyr Val Glu Thr His Thr
    1170                1175                1180

His His Thr Asn Asp Phe Ile Thr Ser Gln Asn Ile Pro Phe Thr Phe
1185                1190                1195                1200

Lys Gly Asn Gln Ile Glu Val His Ile Thr Ser Glu Asp Gly Glu Phe
                1205                1210                1215

Leu Ile Asp His Ile Thr Val Ile Glu Val Ser Lys Thr Asp Thr Asn
            1220                1225                1230

Thr Asn Ile Ile Glu Asn Ser Pro Ile Asn Thr Ser Met Asn Ser Asn
        1235                1240                1245

Val Arg Val Asp Ile Pro Arg Ser Leu
    1250                1255
```

(2) INFORMATION FOR SEQ ID NO:7:

(i) SEQUENCE CHARACTERISTICS:
(A) LENGTH: 3738 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Bacillus thuringiensis
(C) INDIVIDUAL ISOLATE: PS86Q3

(vii) IMMEDIATE SOURCE:
(A) LIBRARY: Lambdagem (TM) - 11 LIBRARY
(B) CLONE: 86Q3a (xi) SEQUENCE DESCRIPTION: SEQ ID NO:7:

```
ATGGCAACAA TTAATGAGTT GTATCCAGTT CCTTATAATG TGCTAGCTCA TCCAATTAAA     60

GAAGTCGATG ATCCTTATTC TTGGTCAAAT TTATTAAAGG GTATACAAGA AGGTTGGGAA    120

GAATGGGGAA AAACAGGACA AAAAAAACTT TTTGAAGACC ATCTTACGAT TGCATGGAAT    180

CTTTATAAAA CAGGAAAATT AGATTATTTC GCTTTGACAA AAGCATCAAT ATCATTGATT    240

GGATTTATTC CAGGGGCAGA AGCAGCAGTT CCCTTTATTA ATATGTTTGT AGACTTTGTT    300

TGGCCTAAAT TATTTGGTGC GAATACAGAA GGAAAAGATC AACAGTTGTT TAATGCTATC    360

ATGGATGCAG TTAATAAAAT GGTAGATAAT AAGTTCTTAA GTTATAATCT TAGTACACTT    420

AATAAAACAA TTGAAGGACT TCAAGGTAAT TTAGGCCTAT TTCAAAATGC TATACAAGTA    480

GCCATTTGTC AAGGCAGTAC ACCAGAAAGA GTAAATTTTG ATCAAAATTG TACACCATGT    540

AATCCAAATC AACCTTGTAA AGATGATTTG GATAGAGTTG CTTCACGTTT TGATACGGCT    600

AATTCTCAAT TCACACAGCA TTTACCAGAA TTTAAAAATC CTTGGTCGGA TGAAAACTCT    660

ACTCAGGAAT TTAAAAGAAC ATCTGTTGAA TTAACTTTAC CAATGTATAC AACAGTAGCT    720

ACGTTACATC TTTTATTATA TGAAGGATAT ATAGAATTTA TGACAAAATG GAATTTTCAC    780

AATGAACAAT ATTTAAATAA TTTAAAGGTA GAATTACAAC AATTGATACA CTCATATTCA    840

GAAACTGTTC GTACAAGTTT CCTTCAATTT TTACCTACCT TGAATAATCG TTCAAAATCA    900

TCCGTAAATG CTTATAACCG TTATGTCCGC AATATGACTG TTAACTGTTT AGATATTGCT    960

GCTACATGGC CTACATTTGA TACACATAAT TATCATCAAG GTGGTAAATT AGATTTAACT   1020
```

-continued

```
CGTATTATTC TTTCAGATAC AGCAGGACCA ATAGAAGAAT ATACTACTGG CGACAAAACT      1080

TCAGGACCTG AACATAGTAA CATTACACCA AATAATATTC TAGATACACC ATCTCCAACA      1140

TATCAGCACT CATTTGTATC TGTTGATTCT ATTGTATATT CTAGAAAAGA ATTACAACAA      1200

TTAGACATAG CTACTTATAG TACAAATAAT AGTAATAATT GTCACCCTTA TGGATTACGA      1260

CTTTCATATA CAGATGGAAG CAGATATGAT TATGGAGATA ATCAACCTGA TTTTACTACT      1320

TCCAATAACA ATTATTGTCA TAATAGCTAT ACTGCCCCTA TTACACTTGT GAATGCACGA      1380

CATTTATATA ATGCAAAAGG CTCTTTACAA AATGTAGAAT CTTTAGTGGT TAGTACTGTA      1440

AATGGTGGAA GTGGTTCATG CATTTGTGAT GCATGGATTA ATTATTTACG TCCTCCTCAA      1500

ACAAGTAAAA ATGAATCACG TCCTGATCAA AAAATTAATG TTTTGTATCC AATAACAGAA      1560

ACTGTAAATA AGGGGACTGG AGGAAATTTA GGAGTTATTT CTGCCTATGT TCCAATGGAA      1620

CTTGTACCAG AAAACGTTAT TGGAGATGTT AATGCTGATA CTAAATTGCC ACTTACACAA      1680

TTAAAGGGCT TTCCATTTGA AAAATATGGT TCTGAGTATA ATAATCGGGG TATCTCTCTT      1740

GTTCGCGAAT GGATAAATGG TAACAATGCA GTTAAACTTT CTAATAGTCA ATCTGTTGGC      1800

ATACAAATTA CGAATCAAAC CAAACAAAAA TATGAAATAC GTTGCCGTTA TGCGAGTAAA      1860

GGAGATAATA ATGTTTATTT TAATGTGGAT TTAAGTGAAA ATCCATTTAG AAATTCCATT      1920

TCTTTTGGAT CTACTGAAAG TTCTGTTGTA GGAGTACAAG GTGAAAATGG AAAGTATATA      1980

TTGAAATCAA TCACAACGGT AGAAATACCT GCTGGAAGTT CTATGTTCA TATAACAAAC       2040

CAAGGTTCTT CAGATCTCTT TTTAGATCGT ATTGAGTTTG TTCCAAAAAT CCAATTCCAA      2100

TTCTGTGATA ATAATAATCT TCACTGTGAT TGTAATAACC CTGTTGACAC CGATTGTACA      2160

TTTTGTTGCG TTTGCACTAG TCTTACTGAT TGTGATTGTA ATAACCCTCG TGGCCTAGAT      2220

TGTACGCTAT GTTGTCAGGT AGAAAATCAG CTACCTTCTT TTGTGACACT TACAGATTTA      2280

CAAAATATTA CGACACAAGT AAATGCATTA GTTGCATCGA GCGAACATGA TACACTTGCA      2340

ACAGACGTGA GTGATTATGA GATTGAAGAA GTTGTACTGA AGTAGATGC ATTATCTGGT       2400

GAAGTGTTTG GAAAAGAGAA AAAAGCATTG CGTAAATTGG TAAATCACAC AAAACGTTTA      2460

AGCAAAGCGC GTAACCTCTT GATAGGAGGA AATTTTGATA ACTTGGATGC TTGGTACAGA      2520

GGCCGAAATG TAGTAAACGT ATCTGATCAT GAACTATTTA AGAGTGATCA TGTATTATTG      2580

CCACCACCAA CACTGTACTC ATCTTATATG TTCCAAAAAG TAGAGGAATC GAAATTAAAA      2640

GCGAATACAC GTTATACTGT GTCTGGTTTT ATTGCACATG CAGAAGATTT AGAAATTGTT      2700

GTGTCTCGTT ATGGGCAAGA AGTGAAGAAA GTGGTTCAAG TTCCATATGG AGAAGCATTC      2760

CCATTGACAT CGAGGGGAGC GATTTGTTGC CCTCCACGTT CTACAAGTAA TGGAAAACCT      2820

GCTGATCCAC ATTTCTTTAG TTACAGTATT GATGTGGGAA CATTAGATGT AGAAGCAAAC      2880

CCTGGTATCG AATTGGGTCT TCGTATTGTA GAACGAACTG GAATGGCACG TGTAAGTAAT      2940

TTAGAAATTC GTGAAGATCG TCCATTAAAG AAAAATGAAC TCCGCAATGT ACAACGTGCA      3000

GCAAGAAATT GGAGAACAGC ATATGACCAA GAACGTGCAG AAGTAACGGC CTTGATTCAA      3060

CCTGTATTAA ATCAAATCAA TGCGTTGTAT GAAAATGAAG ATTGGAATGG AGCAATTCGT      3120

TCTGGAGTTT CTTATCATGA CTTAGAAGCA ATTGTTTTAC CAACATTACC AAAATTAAAT      3180

CATTGGTTTA TGTCTGATAT GTTAGGGGAA CAAGGTTCCA TTTTAGCTCA ATTTCAAGAA      3240

GCATTAGATC GTGCGTATAC GCAACTCGAA GAAAGTACAA TTCTGCATAA TGGTCATTTC      3300

ACAACAGATG CAGCAAATTG GACGATAGAA GGCGATGCAC ATCATGCGAT ATTAGAAGAT      3360

GGTAGACGCG TATTACGTCT TCCAGATTGG TCTTCTAGCG TTTCACAAAC CATTGAAATA      3420
```

```
GAAAATTTTG ATCCAGATAA AGAATATCAG TTAGTTTTCC ATGCACAAGG AGAAGGAACG      3480

GTCTCCCTTC AACATGGTGA AGAAGGAGAA TATGTGGAAA CACACCCGCA TAAGTCTGCG      3540

AATTTTACAA CTTCACACCG TCAAGGAGTC ACATTTGAAA CAAATAAAGT AACAGTTGAA      3600

ATTACCTCAG AAGATGGAGA ATTCCTAGTC GATCATATTG CTCTTGTGGA AGCTCCTCTT      3660

CCTACAGATG ACCAAAGTTC AGATGGAAAT ACGACTTCCA ATACGAATAG CAATACAAGT      3720

ATGAATAATA ATCAATAA                                                    3738
```

(2) INFORMATION FOR SEQ ID NO:8:

(i) SEQUENCE CHARACTERISTICS:
        (A) LENGTH: 1245 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: BACILLUS THURINGIENSIS
        (C) INDIVIDUAL ISOLATE: PS86Q3

(vii) IMMEDIATE SOURCE:
        (A) LIBRARY: LAMBDAGEM (tm) - 11 library
(B) CLONE: 86Q3A (xi) SEQUENCE DESCRIPTION: SEQ ID NO:8:

```
Met Ala Thr Ile Asn Glu Leu Tyr Pro Val Pro Tyr Asn Val Leu Ala
1               5                   10                  15

His Pro Ile Lys Glu Val Asp Asp Pro Tyr Ser Trp Ser Asn Leu Leu
            20                  25                  30

Lys Gly Ile Gln Glu Gly Trp Glu Glu Trp Gly Lys Thr Gly Gln Lys
        35                  40                  45

Lys Leu Phe Glu Asp His Leu Thr Ile Ala Trp Asn Leu Tyr Lys Thr
    50                  55                  60

Gly Lys Leu Asp Tyr Phe Ala Leu Thr Lys Ala Ser Ile Ser Leu Ile
65                  70                  75                  80

Gly Phe Ile Pro Gly Ala Glu Ala Ala Val Pro Phe Ile Asn Met Phe
                85                  90                  95

Val Asp Phe Val Trp Pro Lys Leu Phe Gly Ala Asn Thr Glu Gly Lys
            100                 105                 110

Asp Gln Gln Leu Phe Asn Ala Ile Met Asp Ala Val Asn Lys Met Val
        115                 120                 125

Asp Asn Lys Phe Leu Ser Tyr Asn Leu Ser Thr Leu Asn Lys Thr Ile
    130                 135                 140

Glu Gly Leu Gln Gly Asn Leu Gly Leu Phe Gln Asn Ala Ile Gln Val
145                 150                 155                 160

Ala Ile Cys Gln Gly Ser Thr Pro Glu Arg Val Asn Phe Asp Gln Asn
                165                 170                 175

Cys Thr Pro Cys Asn Pro Asn Gln Pro Cys Lys Asp Asp Leu Asp Arg
            180                 185                 190

Val Ala Ser Arg Phe Asp Thr Ala Asn Ser Gln Phe Thr Gln His Leu
        195                 200                 205

Pro Glu Phe Lys Asn Pro Trp Ser Asp Glu Asn Ser Thr Gln Glu Phe
    210                 215                 220
```

-continued

```
Lys Arg Thr Ser Val Glu Leu Thr Leu Pro Met Tyr Thr Thr Val Ala
225                 230                 235                 240

Thr Leu His Leu Leu Leu Tyr Glu Gly Tyr Ile Glu Phe Met Thr Lys
            245                 250                 255

Trp Asn Phe His Asn Glu Gln Tyr Leu Asn Asn Leu Lys Val Glu Leu
                260                 265                 270

Gln Gln Leu Ile His Ser Tyr Ser Glu Thr Val Arg Thr Ser Phe Leu
        275                 280                 285

Gln Phe Leu Pro Thr Leu Asn Asn Arg Ser Lys Ser Ser Val Asn Ala
    290                 295                 300

Tyr Asn Arg Tyr Val Arg Asn Met Thr Val Asn Cys Leu Asp Ile Ala
305                 310                 315                 320

Ala Thr Trp Pro Thr Phe Asp Thr His Asn Tyr His Gln Gly Gly Lys
                325                 330                 335

Leu Asp Leu Thr Arg Ile Ile Leu Ser Asp Thr Ala Gly Pro Ile Glu
            340                 345                 350

Glu Tyr Thr Thr Gly Asp Lys Thr Ser Gly Pro Glu His Ser Asn Ile
                355                 360                 365

Thr Pro Asn Asn Ile Leu Asp Thr Pro Ser Pro Thr Tyr Gln His Ser
370                 375                 380

Phe Val Ser Val Asp Ser Ile Val Tyr Ser Arg Lys Glu Leu Gln Gln
385                 390                 395                 400

Leu Asp Ile Ala Thr Tyr Ser Thr Asn Asn Ser Asn Asn Cys His Pro
                405                 410                 415

Tyr Gly Leu Arg Leu Ser Tyr Thr Asp Gly Ser Arg Tyr Asp Tyr Gly
                420                 425                 430

Asp Asn Gln Pro Asp Phe Thr Thr Ser Asn Asn Asn Tyr Cys His Asn
            435                 440                 445

Ser Tyr Thr Ala Pro Ile Thr Leu Val Asn Ala Arg His Leu Tyr Asn
    450                 455                 460

Ala Lys Gly Ser Leu Gln Asn Val Glu Ser Leu Val Val Ser Thr Val
465                 470                 475                 480

Asn Gly Gly Ser Gly Ser Cys Ile Cys Asp Ala Trp Ile Asn Tyr Leu
                485                 490                 495

Arg Pro Pro Gln Thr Ser Lys Asn Glu Ser Arg Pro Asp Gln Lys Ile
                500                 505                 510

Asn Val Leu Tyr Pro Ile Thr Glu Thr Val Asn Lys Gly Thr Gly Gly
            515                 520                 525

Asn Leu Gly Val Ile Ser Ala Tyr Val Pro Met Glu Leu Val Pro Glu
        530                 535                 540

Asn Val Ile Gly Asp Val Asn Ala Asp Thr Lys Leu Pro Leu Thr Gln
545                 550                 555                 560

Leu Lys Gly Phe Pro Phe Glu Lys Tyr Gly Ser Glu Tyr Asn Asn Arg
                565                 570                 575

Gly Ile Ser Leu Val Arg Glu Trp Ile Asn Gly Asn Asn Ala Val Lys
            580                 585                 590

Leu Ser Asn Ser Gln Ser Val Gly Ile Gln Ile Thr Asn Gln Thr Lys
        595                 600                 605

Gln Lys Tyr Glu Ile Arg Cys Arg Tyr Ala Ser Lys Gly Asp Asn Asn
    610                 615                 620

Val Tyr Phe Asn Val Asp Leu Ser Glu Asn Pro Phe Arg Asn Ser Ile
625                 630                 635                 640
```

-continued

```
Ser Phe Gly Ser Thr Glu Ser Ser Val Val Gly Val Gln Gly Glu Asn
                645                 650                 655
Gly Lys Tyr Ile Leu Lys Ser Ile Thr Thr Val Glu Ile Pro Ala Gly
            660                 665                 670
Ser Phe Tyr Val His Ile Thr Asn Gln Gly Ser Ser Asp Leu Phe Leu
        675                 680                 685
Asp Arg Ile Glu Phe Val Pro Lys Ile Gln Phe Gln Phe Cys Asp Asn
    690                 695                 700
Asn Asn Leu His Cys Asp Cys Asn Asn Pro Val Asp Thr Asp Cys Thr
705                 710                 715                 720
Phe Cys Cys Val Cys Thr Ser Leu Thr Asp Cys Asp Cys Asn Asn Pro
            725                 730                 735
Arg Gly Leu Asp Cys Thr Leu Cys Cys Gln Val Glu Asn Gln Leu Pro
        740                 745                 750
Ser Phe Val Thr Leu Thr Asp Leu Gln Asn Ile Thr Thr Gln Val Asn
    755                 760                 765
Ala Leu Val Ala Ser Ser Glu His Asp Thr Leu Ala Thr Asp Val Ser
770                 775                 780
Asp Tyr Glu Ile Glu Glu Val Val Leu Lys Val Asp Ala Leu Ser Gly
785                 790                 795                 800
Glu Val Phe Gly Lys Glu Lys Lys Ala Leu Arg Lys Leu Val Asn His
            805                 810                 815
Thr Lys Arg Leu Ser Lys Ala Arg Asn Leu Leu Ile Gly Gly Asn Phe
        820                 825                 830
Asp Asn Leu Asp Ala Trp Tyr Arg Gly Arg Asn Val Val Asn Val Ser
    835                 840                 845
Asp His Glu Leu Phe Lys Ser Asp His Val Leu Leu Pro Pro Pro Thr
850                 855                 860
Leu Tyr Ser Ser Tyr Met Phe Gln Lys Val Glu Glu Ser Lys Leu Lys
865                 870                 875                 880
Ala Asn Thr Arg Tyr Thr Val Ser Gly Phe Ile Ala His Ala Glu Asp
            885                 890                 895
Leu Glu Ile Val Val Ser Arg Tyr Gly Gln Glu Val Lys Lys Val Val
        900                 905                 910
Gln Val Pro Tyr Gly Glu Ala Phe Pro Leu Thr Ser Arg Gly Ala Ile
    915                 920                 925
Cys Cys Pro Pro Arg Ser Thr Ser Asn Gly Lys Pro Ala Asp Pro His
930                 935                 940
Phe Phe Ser Tyr Ser Ile Asp Val Gly Thr Leu Asp Val Glu Ala Asn
945                 950                 955                 960
Pro Gly Ile Glu Leu Gly Leu Arg Ile Val Glu Arg Thr Gly Met Ala
            965                 970                 975
Arg Val Ser Asn Leu Glu Ile Arg Glu Asp Arg Pro Leu Lys Lys Asn
        980                 985                 990
Glu Leu Arg Asn Val Gln Arg Ala Ala Arg Asn Trp Arg Thr Ala Tyr
    995                 1000                1005
Asp Gln Glu Arg Ala Glu Val Thr Ala Leu Ile Gln Pro Val Leu Asn
    1010                1015                1020
Gln Ile Asn Ala Leu Tyr Glu Asn Glu Asp Trp Asn Gly Ala Ile Arg
1025                1030                1035                1040
Ser Gly Val Ser Tyr His Asp Leu Glu Ala Ile Val Leu Pro Thr Leu
            1045                1050                1055
Pro Lys Leu Asn His Trp Phe Met Ser Asp Met Leu Gly Glu Gln Gly
```

```
                  1060             1065             1070
Ser Ile Leu Ala Gln Phe Gln Glu Ala Leu Asp Arg Ala Tyr Thr Gln
        1075             1080             1085

Leu Glu Glu Ser Thr Ile Leu His Asn Gly His Phe Thr Thr Asp Ala
    1090             1095             1100

Ala Asn Trp Thr Ile Glu Gly Asp Ala His His Ala Ile Leu Glu Asp
1105             1110             1115             1120

Gly Arg Arg Val Leu Arg Leu Pro Asp Trp Ser Ser Val Ser Gln
            1125             1130             1135

Thr Ile Glu Ile Glu Asn Phe Asp Pro Asp Lys Glu Tyr Gln Leu Val
        1140             1145             1150

Phe His Ala Gln Gly Glu Gly Thr Val Ser Leu Gln His Gly Glu Glu
        1155             1160             1165

Gly Glu Tyr Val Glu Thr His Pro His Lys Ser Ala Asn Phe Thr Thr
    1170             1175             1180

Ser His Arg Gln Gly Val Thr Phe Glu Thr Asn Lys Val Thr Val Glu
1185             1190             1195             1200

Ile Thr Ser Glu Asp Gly Glu Phe Leu Val Asp His Ile Ala Leu Val
            1205             1210             1215

Glu Ala Pro Leu Pro Thr Asp Asp Gln Ser Ser Asp Gly Asn Thr Thr
        1220             1225             1230

Ser Asn Thr Asn Ser Asn Thr Ser Met Asn Asn Asn Gln
        1235             1240             1245
```

(2) INFORMATION FOR SEQ ID NO:9:

(i) SEQUENCE CHARACTERISTICS:
        (A) LENGTH: 2412 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Bacillus thuringiensis
        (C) INDIVIDUAL ISOLATE: PS63B (vii) IMMEDIATE SOURCE:
(B) CLONE: E. coli NM522(pMYC1642) NRRL B-18961

(xi) SEQUENCE DESCRIPTION: SEQ ID NO:9:

```
ATGACTTGTC AATTACAAGC GCAACCACTT ATTCCCTATA ACGTACTAGC AGGAGTTCCA     60

ACTAGTAATA CAGGTAGTCC AATCGGCAAT GCAGGTAATC AATTTGATCA GTTTGAGCAA    120

ACCGTTAAAG AGCTCAAGGA AGCATGGGAA GCGTTCCAAA AAAACGGAAG TTTCTCATTA    180

GCAGCTCTTG AAAAGGGATT TGATGCAGCA ATCGGAGGAG GATCCTTTGA TTATTTAGGT    240

TTAGTTCAAG CCGGCCTAGG ATTAGTTGGT ACGCTAGGCG CCGCAATCCC TGGTGTTTCA    300

GTGGCAGTGC CTCTTATTAG CATGCTTGTT GGTGTTTTTT GGCCAAAGGG CACAAACAAC    360

CAAGAAAACC TTATTACAGT TATTGATAAG GAAGTTCAGA GAATACTAGA TGAAAAGCTA    420

TCTGATCAGT TAATAAAGAA ATTGAACGCA GATTTAAATG CTTTTACGGA CCTAGTAACT    480

CGTTTGGAAG AAGTAATAAT AGATGCAACT TTCGAGAATC ACAAGCCTGT ACTACAAGTA    540

AGTAAATCAA ATTATATGAA AGTGGATTCA GCATATTTCT CAACAGGAGG TATTCTTACT    600

CTTGGCATGA GTGATTTTCT TACTGATACC TATTCAAAGC TTACCTTCCC ATTATATGTA    660
```

-continued

```
CTAGGCGCAA CTATGAAACT TTCAGCATAT CATAGTTATA TACAATTCGG AAATACATGG      720

CTTAATAAAG TTTATGATTT ATCATCAGAT GAGGGAAAAA CAATGTCGCA GGCTTTAGCA      780

CGAGCTAAAC AGCATATGCG CCAAGACATA GCATTTTATA CAAGCCAAGC TTTAAACATG      840

TTTACTGGGA ATCTCCCTTC ATTATCATCT AATAAATATG CAATTAATGA CTATAATGTA      900

TACACTCGAG CAATGGTATT GAATGGCTTA GATATAGTAG CAACATGGCC TACCCTATAT      960

CCAGATGACT ATTCGTCTCA GATAAAACTG GAGAAACAC GCGTGATCTT TCAGATATG      1020

GTCGGGCAAA GTGAGAGTAG AGATGGCAGC GTAACGATTA AAAATATTTT TGACAATACA     1080

GATTCACATC AACATGGATC CATAGGTCTC AATTCAATCT CTTATTTCCC AGATGAGTTA     1140

CAGAAAGCAC AACTTCGCAT GTATGATTAT AATCACAAAC CTTATTGTAC GGACTGTTTC     1200

TGCTGGCCGT ATGGAGTGAT TTTAAACTAT AACAAGAATA CCTTTAGATA TGGCGATAAT     1260

GATCCAGGTC TTTCAGGAGA CGTTCAACTC CCAGCACCTA TGAGTGTAGT TAATGCCCAA     1320

ACTCAAACAG CCCAATATAC AGATGGAGAA ACATATGGA CAGATACTGG CCGCAGTTGG     1380

CTTTGTACTC TACGTGGCTA CTGTACTACA AACTGTTTTC CAGGAAGAGG TTGTTATAAT     1440

AATAGTACTG GATATGGAGA AAGTTGCAAT CAATCACTTC CAGGTCAAAA AATACATGCA     1500

CTATATCCTT TTACACAAAC AAATGTGCTG GGACAATCAG GCAAACTAGG ATTGCTAGCA     1560

AGTCATATTC CATATGACCT AAGTCCGAAC AATACGATTG GTGACAAAGA TACAGATTCT     1620

ACGAATATTG TCGCAAAAGG AATTCCAGTG GAAAAAGGGT ATGCATCCAG TGGACAAAAA     1680

GTTGAAATTA TACGAGAGTG GATAAATGGT GCGAATGTAG TTCAATTATC TCCAGGCCAA     1740

TCTTGGGGAA TGGATTTTAC CAATAGCACA GGTGGTCAAT ATATGGTCCG CTGTCGATAT     1800

GCAAGTACAA ACGATACTCC AATCTTTTTT AATTTAGTGT ATGACGGGGG ATCGAATCCT     1860

ATTTATAACC AGATGACATT CCCTGCTACA AAAGAGACTC CAGCTCACGA TTCAGTAGAT     1920

AACAAGATAC TAGGCATAAA AGGAATAAAT GGAAATTATT CACTCATGAA TGTAAAAGAT     1980

TCTGTCGAAC TTCCATCTGG GAAATTTCAT GTTTTTTTCA CAAATAATGG ATCATCTGCT     2040

ATTTATTTAG ATCGACTTGA GTTTGTTCCT TTAGATCAAC CAGCAGCGCC AACACAGTCA     2100

ACACAACCAA TTAATTATCC TATCACAAGT AGGTTACCTC ATCGTTCCGG AGAACCACCT     2160

GCAATAATAT GGGAGAAATC AGGGAATGTT CGCGGGAATC AACTAACTAT ATCGGCACAA     2220

GGTGTTCCAG AAAATTCCCA AATATATCTT TCGGTGGGTG GCGATCGCCA AATTTTAGAC     2280

CGTAGCAACG GATTTAAATT AGTTAATTAC TCACCTACTT ATTCTTTCAC TAACATTCAG     2340

GCTAGCTCGT CAAATTTAGT AGATATTACA AGTGGTACCA TCACTGGCCA AGTACAAGTA     2400

TCTAATCTAT AA                                                          2412
```

(2) INFORMATION FOR SEQ ID NO:10:

(i) SEQUENCE CHARACTERISTICS:
        (A) LENGTH: 803 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: Bacillus thuringiensis
        (C) INDIVIDUAL ISOLATE: PS63B (vii) IMMEDIATE SOURCE:
    (B) CLONE: E. coli NM522(pMYC1642) NRRL B-18961

(xi) SEQUENCE DESCRIPTION: SEQ ID NO:10:

```
Met Thr Cys Gln Leu Gln Ala Gln Pro Leu Ile Pro Tyr Asn Val Leu
1               5                   10                  15

Ala Gly Val Pro Thr Ser Asn Thr Gly Ser Pro Ile Gly Asn Ala Gly
            20                  25                  30

Asn Gln Phe Asp Gln Phe Glu Gln Thr Val Lys Glu Leu Lys Glu Ala
        35                  40                  45

Trp Glu Ala Phe Gln Lys Asn Gly Ser Phe Ser Leu Ala Ala Leu Glu
    50                  55                  60

Lys Gly Phe Asp Ala Ala Ile Gly Gly Ser Phe Asp Tyr Leu Gly
65              70                  75                  80

Leu Val Gln Ala Gly Leu Gly Leu Val Gly Thr Leu Gly Ala Ala Ile
                85                  90                  95

Pro Gly Val Ser Val Ala Val Pro Leu Ile Ser Met Leu Val Gly Val
                100                 105                 110

Phe Trp Pro Lys Gly Thr Asn Asn Gln Glu Asn Leu Ile Thr Val Ile
        115                 120                 125

Asp Lys Glu Val Gln Arg Ile Leu Asp Glu Lys Leu Ser Asp Gln Leu
130                 135                 140

Ile Lys Lys Leu Asn Ala Asp Leu Asn Ala Phe Thr Asp Leu Val Thr
145                 150                 155                 160

Arg Leu Glu Glu Val Ile Ile Asp Ala Thr Phe Glu Asn His Lys Pro
                165                 170                 175

Val Leu Gln Val Ser Lys Ser Asn Tyr Met Lys Val Asp Ser Ala Tyr
                180                 185                 190

Phe Ser Thr Gly Gly Ile Leu Thr Leu Gly Met Ser Asp Phe Leu Thr
            195                 200                 205

Asp Thr Tyr Ser Lys Leu Thr Phe Pro Leu Tyr Val Leu Gly Ala Thr
        210                 215                 220

Met Lys Leu Ser Ala Tyr His Ser Tyr Ile Gln Phe Gly Asn Thr Trp
225                 230                 235                 240

Leu Asn Lys Val Tyr Asp Leu Ser Ser Asp Glu Gly Lys Thr Met Ser
                245                 250                 255

Gln Ala Leu Ala Arg Ala Lys Gln His Met Arg Gln Asp Ile Ala Phe
            260                 265                 270

Tyr Thr Ser Gln Ala Leu Asn Met Phe Thr Gly Asn Leu Pro Ser Leu
        275                 280                 285

Ser Ser Asn Lys Tyr Ala Ile Asn Asp Tyr Asn Val Tyr Thr Arg Ala
290                 295                 300

Met Val Leu Asn Gly Leu Asp Ile Val Ala Thr Trp Pro Thr Leu Tyr
305                 310                 315                 320

Pro Asp Asp Tyr Ser Ser Gln Ile Lys Leu Glu Lys Thr Arg Val Ile
                325                 330                 335

Phe Ser Asp Met Val Gly Gln Ser Ser Arg Asp Gly Ser Val Thr
            340                 345                 350

Ile Lys Asn Ile Phe Asp Asn Thr Asp Ser His Gln His Gly Ser Ile
        355                 360                 365

Gly Leu Asn Ser Ile Ser Tyr Phe Pro Asp Glu Leu Gln Lys Ala Gln
    370                 375                 380

Leu Arg Met Tyr Asp Tyr Asn His Lys Pro Tyr Cys Thr Asp Cys Phe
385                 390                 395                 400
```

-continued

```
Cys Trp Pro Tyr Gly Val Ile Leu Asn Tyr Asn Lys Asn Thr Phe Arg
                405                 410                 415

Tyr Gly Asp Asn Asp Pro Gly Leu Ser Gly Asp Val Gln Leu Pro Ala
        420                 425                 430

Pro Met Ser Val Val Asn Ala Gln Thr Gln Thr Ala Gln Tyr Thr Asp
        435                 440                 445

Gly Glu Asn Ile Trp Thr Asp Thr Gly Arg Ser Trp Leu Cys Thr Leu
    450                 455                 460

Arg Gly Tyr Cys Thr Thr Asn Cys Phe Pro Gly Arg Gly Cys Tyr Asn
465                 470                 475                 480

Asn Ser Thr Gly Tyr Gly Glu Ser Cys Asn Gln Ser Leu Pro Gly Gln
                485                 490                 495

Lys Ile His Ala Leu Tyr Pro Phe Thr Gln Thr Asn Val Leu Gly Gln
                500                 505                 510

Ser Gly Lys Leu Gly Leu Leu Ala Ser His Ile Pro Tyr Asp Leu Ser
            515                 520                 525

Pro Asn Asn Thr Ile Gly Asp Lys Asp Thr Asp Ser Thr Asn Ile Val
        530                 535                 540

Ala Lys Gly Ile Pro Val Glu Lys Gly Tyr Ala Ser Ser Gly Gln Lys
545                 550                 555                 560

Val Glu Ile Ile Arg Glu Trp Ile Asn Gly Ala Asn Val Val Gln Leu
                565                 570                 575

Ser Pro Gly Gln Ser Trp Gly Met Asp Phe Thr Asn Ser Thr Gly Gly
            580                 585                 590

Gln Tyr Met Val Arg Cys Arg Tyr Ala Ser Thr Asn Asp Thr Pro Ile
        595                 600                 605

Phe Phe Asn Leu Val Tyr Asp Gly Gly Ser Asn Pro Ile Tyr Asn Gln
        610                 615                 620

Met Thr Phe Pro Ala Thr Lys Glu Thr Pro Ala His Asp Ser Val Asp
625                 630                 635                 640

Asn Lys Ile Leu Gly Ile Lys Gly Ile Asn Gly Asn Tyr Ser Leu Met
                645                 650                 655

Asn Val Lys Asp Ser Val Glu Leu Pro Ser Gly Lys Phe His Val Phe
            660                 665                 670

Phe Thr Asn Asn Gly Ser Ser Ala Ile Tyr Leu Asp Arg Leu Glu Phe
        675                 680                 685

Val Pro Leu Asp Gln Pro Ala Ala Pro Thr Gln Ser Thr Gln Pro Ile
        690                 695                 700

Asn Tyr Pro Ile Thr Ser Arg Leu Pro His Arg Ser Gly Glu Pro Pro
705                 710                 715                 720

Ala Ile Ile Trp Glu Lys Ser Gly Asn Val Arg Gly Asn Gln Leu Thr
                725                 730                 735

Ile Ser Ala Gln Gly Val Pro Glu Asn Ser Gln Ile Tyr Leu Ser Val
            740                 745                 750

Gly Gly Asp Arg Gln Ile Leu Asp Arg Ser Asn Gly Phe Lys Leu Val
        755                 760                 765

Asn Tyr Ser Pro Thr Tyr Ser Phe Thr Asn Ile Gln Ala Ser Ser Ser
        770                 775                 780

Asn Leu Val Asp Ile Thr Ser Gly Thr Ile Thr Gly Gln Val Gln Val
785                 790                 795                 800

Ser Asn Leu
```

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Arg Glu Trp Ile Asn Gly Ala Asn
1               5

(2) INFORMATION FOR SEQ ID NO:12:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:12:

AGARTRKWTW AATGGWGCKM A                                              21

(2) INFORMATION FOR SEQ ID NO:13:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:13:

GARTGGWTAA ATGGTRMSAA                                                20

(2) INFORMATION FOR SEQ ID NO:14:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Pro Thr Phe Asp Pro Asp Leu Tyr
1               5

(2) INFORMATION FOR SEQ ID NO:15:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:15:

CCNACYTTTK ATCCAGATSW YTAT                                           24

(2) INFORMATION FOR SEQ ID NO:16:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:16:

CCWACWTTYG ATMCASATMW TTAT                                                  24

(2) INFORMATION FOR SEQ ID NO:17:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Ala Ile Leu Asn Glu Leu Tyr Pro Ser Val Pro Tyr Asn Val
1               5                   10

(2) INFORMATION FOR SEQ ID NO:18:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Ala Ile Leu Asn Glu Leu Tyr Pro Ser Val Pro Tyr Asn Val
1               5                   10

(2) INFORMATION FOR SEQ ID NO:19:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Met Ala Thr Ile Asn Glu Leu Tyr Pro Asn Val Pro Tyr Asn Val Leu
1               5                   10                  15

(2) INFORMATION FOR SEQ ID NO:20:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Gln Leu Gln Ala Gln Pro Leu Ile Pro Tyr Asn Val Leu Ala
1               5                   10

(2) INFORMATION FOR SEQ ID NO:21:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:21:

Ala Thr Leu Asn Glu Val Tyr Pro Val Asn
1               5                   10

(2) INFORMATION FOR SEQ ID NO:22:

(i) SEQUENCE CHARACTERISTICS:
           (A) LENGTH: 15 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:22:

Val Gln Arg Ile Leu Asp Glu Lys Leu Ser Phe Gln Leu Ile Lys
1               5                   10                  15

(2) INFORMATION FOR SEQ ID NO:23:

(i) SEQUENCE CHARACTERISTICS:
           (A) LENGTH: 23 bases
           (B) TYPE: nucleic acid
           (C) STRANDEDNESS: single
           (D) TOPOLOGY: linear (ii) MOLECULE TYPE: DNA (synthetic)

(xi) SEQUENCE DESCRIPTION: SEQ ID NO:23:

GCAATTTTAA ATGAATTATA TCC                                                 23

(2) INFORMATION FOR SEQ ID NO:24:

(i) SEQUENCE CHARACTERISTICS:
           (A) LENGTH: 17 bases
           (B) TYPE: nucleic acid
           (C) STRANDEDNESS: single
           (D) TOPOLOGY: linear (ii) MOLECULE TYPE: DNA (synthetic)

(xi) SEQUENCE DESCRIPTION: SEQ ID NO:24:

CAAYTACAAG CWCAACC                                                        17

(2) INFORMATION FOR SEQ ID NO:25:

(i) SEQUENCE CHARACTERISTICS:
           (A) LENGTH: 21 bases
           (B) TYPE: nucleic acid
           (C) STRANDEDNESS: single
           (D) TOPOLOGY: linear (ii) MOLECULE TYPE: DNA (synthetic)

(xi) SEQUENCE DESCRIPTION: SEQ ID NO:25:

TTCATCTAAA ATTCTTTGWA C                                                   21

(2) INFORMATION FOR SEQ ID NO:26:

(i) SEQUENCE CHARACTERISTICS:
           (A) LENGTH: 21 bases

```
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:26:

GCWACWTTAA ATGAAGTWTA T                                             21

(2) INFORMATION FOR SEQ ID NO:27:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:27:

AATGAAGTWT ATCCWGTWAA T                                             21

(2) INFORMATION FOR SEQ ID NO:28:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:28:

GCAAGCGGCC GCTTATGGAA TAAATTCAAT TYKRTCWA                            38

(2) INFORMATION FOR SEQ ID NO:29:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:29:

AGACTGGATC CATGGCWACW ATWAATGAAT TATAYCC                             37

(2) INFORMATION FOR SEQ ID NO:30:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

Glu Ser Lys Leu Lys Pro Asn Thr Arg Tyr
1               5                   10

(2) INFORMATION FOR SEQ ID NO:31:

(i) SEQUENCE CHARACTERISTICS:
        (A) LENGTH: 29 bases
        (B) TYPE: nucleic acid
        (C) STRANDEDNESS: single
        (D) TOPOLOGY: linear
```

(ii) MOLECULE TYPE: DNA (synthetic)

(xi) SEQUENCE DESCRIPTION: SEQ ID NO:31:

TAACGTGTAT WCGSTTTTAA TTTWGAYTC 29

(2) INFORMATION FOR SEQ ID NO:32:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Tyr Ile Asp Lys Ile Glu Phe Ile Pro
1            5

(2) INFORMATION FOR SEQ ID NO:33:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:33:

TGGAATAAAT TCAATTYKRT CWA 23

(2) INFORMATION FOR SEQ ID NO:34:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:34:

AGGAACAAAY TCAAKWCGRT CTA 23

(2) INFORMATION FOR SEQ ID NO:35:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:35:

TTTAGATCGT MTTGARTTTR TWCC 24

(2) INFORMATION FOR SEQ ID NO:36:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Ile Thr Ser Glu Asp
1               5

(2) INFORMATION FOR SEQ ID NO:37:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:37:

TCTCCATCTT CTGARGWAAT                                                    20

(2) INFORMATION FOR SEQ ID NO:38:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

Leu Asp Arg Ile Glu Phe Val Pro
1               5

(2) INFORMATION FOR SEQ ID NO:39:

(i) SEQUENCE CHARACTERISTICS:
        (A) LENGTH: 731 amino acids
        (B) TYPE: amino acid
        (C) STRANDEDNESS: single
        (D) TOPOLOGY: linear (ii) MOLECULE TYPE: peptide (iii) HYPOTHETICAL: YES (xi) SEQUENCE DESCRIPTION: SEQ ID NO:39:

Met Xaa Xaa Xaa Xaa Xaa Xaa Tyr Pro Xaa Xaa Xaa Tyr Xaa Xaa Xaa
1               5                   10                  15

Xaa Xaa Xaa Xaa Xaa Xaa Xaa Xaa Xaa Xaa Xaa Xaa Xaa Xaa Xaa
        20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Pro Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Lys Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa Xaa Xaa

```
           145                 150                 155                 160
Xaa Xaa Xaa Xaa Xaa Xaa Xaa Xaa Xaa Xaa Xaa Xaa Xaa Xaa Xaa Xaa
            165                 170                 175
Xaa Xaa Xaa Xaa Xaa Xaa Xaa Xaa Xaa Xaa Xaa Xaa Xaa Xaa Xaa Xaa
            180                 185                 190
Xaa Xaa Xaa Xaa Xaa Xaa Xaa Xaa Xaa Xaa Xaa Xaa Xaa Xaa Xaa Xaa
            195                 200                 205
Xaa Xaa Xaa Xaa Xaa Xaa Xaa Xaa Xaa Xaa Xaa Xaa Xaa Xaa Xaa Xaa
            210                 215                 220
Xaa Xaa Xaa Xaa Xaa Glu Xaa Xaa Xaa Xaa Xaa Xaa Xaa Xaa Xaa Xaa
225                 230                 235                 240
Pro Xaa Tyr Xaa Xaa Xaa Xaa Xaa Xaa His Xaa Xaa Xaa Xaa Xaa Xaa
            245                 250                 255
Xaa Xaa Xaa Xaa Xaa Xaa Xaa Xaa Xaa Xaa Xaa Xaa Xaa Xaa Xaa Xaa
            260                 265                 270
Xaa Xaa Xaa Xaa Xaa Xaa Xaa Xaa Xaa Xaa Xaa Xaa Xaa Xaa Xaa Xaa
            275                 280                 285
Xaa Xaa Xaa Xaa Xaa Xaa Xaa Xaa Xaa Xaa Xaa Xaa Xaa Xaa Xaa Xaa
            290                 295                 300
Xaa Xaa Xaa Xaa Xaa Xaa Xaa Xaa Xaa Xaa Xaa Xaa Xaa Xaa Xaa Tyr
305                 310                 315                 320
Xaa Xaa Xaa Xaa Xaa Xaa Xaa Xaa Xaa Xaa Xaa Xaa Xaa Xaa Xaa Pro
            325                 330                 335
Xaa Xaa Xaa Xaa Xaa Xaa Tyr Xaa Xaa Xaa Xaa Xaa Xaa Xaa Xaa Xaa
            340                 345                 350
Xaa Xaa Xaa Xaa Xaa Xaa Xaa Xaa Xaa Xaa Xaa Xaa Xaa Xaa Xaa Xaa
            355                 360                 365
Xaa Xaa Xaa Xaa Xaa Xaa Xaa Xaa Xaa Xaa Xaa Xaa Xaa Xaa Xaa Xaa
            370                 375                 380
Xaa Xaa Xaa Xaa Xaa Xaa Xaa Xaa Xaa Xaa Xaa Xaa Xaa Xaa Xaa Xaa
385                 390                 395                 400
Xaa Xaa Xaa Xaa Xaa Xaa Xaa Xaa Xaa Xaa Xaa Xaa Xaa Xaa Xaa Xaa
            405                 410                 415
Xaa Xaa Xaa Xaa Xaa Xaa Xaa Xaa Xaa Xaa Xaa Xaa Xaa Xaa Xaa Xaa
            420                 425                 430
Xaa Xaa Xaa Xaa Xaa Xaa Xaa Xaa Xaa Xaa Xaa Xaa Xaa Xaa Xaa Xaa
            435                 440                 445
Xaa Xaa Xaa Xaa Xaa Xaa Xaa Xaa Xaa Xaa Xaa Xaa Xaa Xaa Xaa Xaa
            450                 455                 460
Xaa Xaa Xaa Xaa Xaa Xaa Xaa Xaa Pro Xaa Xaa Xaa Xaa Xaa Xaa Xaa
465                 470                 475                 480
Xaa Xaa Xaa Xaa Xaa Xaa Xaa Xaa Xaa Xaa Xaa Xaa Xaa Xaa Xaa Xaa
            485                 490                 495
Xaa Xaa Xaa Xaa Xaa Xaa Xaa Xaa Xaa Xaa Xaa Xaa Xaa Xaa Xaa Xaa
            500                 505                 510
Xaa Xaa Xaa Xaa Xaa Xaa Xaa Xaa Xaa Xaa Xaa Xaa Xaa Xaa Xaa Xaa
            515                 520                 525
Xaa Xaa Xaa Xaa Xaa Xaa Xaa Xaa Xaa Xaa Xaa Xaa Tyr Xaa Xaa Xaa
            530                 535                 540
Xaa Xaa Xaa Xaa Xaa Xaa Xaa Xaa Xaa Xaa Xa

```
Xaa Xaa Xaa Xaa Xaa Xaa Xaa Xaa Xaa Xaa Xaa Xaa Xaa Xaa
        580             585             590

Xaa Xaa Xaa Xaa Xaa Xaa Xaa Xaa Xaa Xaa Xaa Xaa Xaa Xaa
    595             600             605

Xaa Xaa Xaa Xaa Xaa Xaa Xaa Xaa Xaa Xaa Xaa Xaa Xaa Xaa
    610             615             620

Xaa Xaa Xaa Xaa Xaa Xaa Xaa Xaa Xaa Xaa Xaa Tyr Xaa Xaa
625             630             635             640

Xaa Xaa Xaa Xaa Pro Xaa Xaa Xaa Xaa Xaa Xaa Xaa Xaa Xaa
            645             650             655

Xaa Xaa Xaa Xaa Xaa Xaa Xaa Xaa Xaa Xaa Xaa Xaa Xaa Xaa
    660             665             670

Xaa Xaa Xaa Xaa Xaa Xaa Xaa Xaa Xaa Xaa Xaa Xaa Tyr Xaa
    675             680             685

Xaa Xaa Xaa Xaa Xaa Xaa Xaa Xaa Xaa Xaa Xaa Xaa Xaa Xaa
    690             695             700

Xaa Xaa Xaa Xaa Xaa Xaa Xaa Xaa Xaa Xaa Xaa Xaa Xaa Xaa
705             710             715             720

Xaa Xaa Xaa Xaa Xaa Xaa Xaa Xaa Pro Xaa Xaa
            725             730
```

(2) INFORMATION FOR SEQ ID NO:40:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:40:

AGACTGGATC CATGGCWACW ATWAATGAAT TATAYCC                    37

(2) INFORMATION FOR SEQ ID NO:41:

(i) SEQUENCE CHARACTERISTICS:
        (A) LENGTH: 48 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:41:

GACTGCGGCC GCGTCGACTT AACGTGTATW CGSTTTTAAT TTWGAYTC          48

(2) INFORMATION FOR SEQ ID NO:42:

(i) SEQUENCE CHARACTERISTICS:
        (A) LENGTH: 3660 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus thuringiensis
        (C) INDIVIDUAL ISOLATE: PS86Q3

(vii) IMMEDIATE SOURCE:
   (A) LIBRARY: Lambdagem (TM) - 11 library of Luis
       Foncerrada
   (B) CLONE: 86Q3c (xi) SEQUENCE DESCRIPTION: SEQ ID NO:42:

| | | | | | |
|---|---|---|---|---|---|
| ATGGCAATTT | TAAATGAATT | ATATCCATCT | GTACCTTATA | ATGTATTGGC | GTATACGCCA | 60 |
| CCCTCTTTTT | TACCTGATGC | GGGTACACAA | GCTACACCTG | CTGACTTAAC | AGCTTATGAA | 120 |
| CAATTGTTGA | AAAATTTAGA | AAAAGGGATA | AATGCTGGAA | CTTATTCGAA | AGCAATAGCT | 180 |
| GATGTACTTA | AAGGTATTTT | TATAGATGAT | ACAATAAATT | ATCAAACATA | TGTAAATATT | 240 |
| GGTTTAAGTT | TAATTACATT | AGCTGTACCG | GAAATTGGTA | TTTTTACACC | TTTCATCGGT | 300 |
| TTGTTTTTTG | CTGCATTGAA | TAAACATGAT | GCTCCACCTC | CTCCTAATGC | AAAAGATATA | 360 |
| TTTGAGGCTA | TGAAACCAGC | GATTCAAGAG | ATGATTGATA | GAACTTTAAC | TGCGGATGAG | 420 |
| CAAACATTTT | TAAATGGGGA | AATAAGTGGT | TTACAAAATT | TAGCAGCAAG | ATACCAGTCT | 480 |
| ACAATGGATG | ATATTCAAAG | CCATGGAGGA | TTTAATAAGG | TAGATTCTGG | ATTAATTAAA | 540 |
| AAGTTTACAG | ATGAGGTACT | ATCTTTAAAT | AGTTTTTATA | CAGATCGTTT | ACCTGTATTT | 600 |
| ATTACAGATA | ATACAGCGGA | TCGAACTTTG | TTAGGTCTTC | CTTATTATGC | TATACTTGCG | 660 |
| AGCATGCATC | TTATGTTATT | AAGAGATATA | ATTACTAAGG | GTCCGACATG | GGATTCTAAA | 720 |
| ATTAATTTCA | CACCAGATGC | AATTGATTCC | TTTAAAACCG | ATATTAAAAA | TAATATAAAG | 780 |
| CTTTACTCTA | AAACTATTTA | TGACGTATTT | CAGAAGGGAC | TTGCTTCATA | CGGAACGCCT | 840 |
| TCTGATTTAG | AGTCCTTTGC | AAAAAAAAAA | AAATATATTG | AAATTATGAC | AACACATTGT | 900 |
| TTAGATTTTG | CAAGATTGTT | TCCTACTTTT | GATCCAGATC | TTTATCCAAC | AGGATCAGGT | 960 |
| GATATAAGTT | TACAAAAAAC | ACGTAGAATT | CTTTCTCCTT | TTATCCCTAT | ACGTACTGCA | 1020 |
| GATGGGTTAA | CATTAAATAA | TACTTCAATT | GATACTTCAA | ATTGGCCTAA | TTATGAAAAT | 1080 |
| GGGAATGGCG | CGTTTCCAAA | CCCAAAAGAA | AGAATATTAA | AACAATTCAA | ACTGTATCCT | 1140 |
| AGTTGGAGAG | CGGGACAGTA | CGGTGGGCTT | TTACAACCTT | ATTTATGGGC | AATAGAAGTC | 1200 |
| CAAGATTCTG | TAGAGACTCG | TTTGTATGGG | CAGCTTCCAG | CTGTAGATCC | ACAGGCAGGG | 1260 |
| CCTAATTATG | TTTCCATAGA | TTCTTCTAAT | CCAATCATAC | AAATAAATAT | GGATACTTGG | 1320 |
| AAAACACCAC | CACAAGGTGC | GAGTGGGTGG | AATACAAATT | TAATGAGAGG | AAGTGTAAGC | 1380 |
| GGGTTAAGTT | TTTTACAACG | AGATGGTACG | AGACTTAGTG | CTGGTATGGG | TGGTGGTTTT | 1440 |
| GCTGATACAA | TATATAGTCT | CCCTGCAACT | CATTATCTTT | CTTATCTCTA | TGGAACTCCT | 1500 |
| TATCAAACTT | CTGATAACTA | TTCTGGTCAC | GTTGGTGCAT | TGGTAGGTGT | GAGTACGCCT | 1560 |
| CAAGAGGCTA | CTCTTCCTAA | TATTATAGGT | CAACCAGATG | AACAGGGAAA | TGTATCTACA | 1620 |
| ATGGGATTTC | CGTTTGAAAA | AGCTTCTTAT | GGAGGTACAG | TTGTTAAAGA | ATGGTTAAAT | 1680 |
| GGTGCGAATG | CGATGAAGCT | TTCTCCTGGG | CAATCTATAG | GTATTCCTAT | TACAAATGTA | 1740 |
| ACAAAACACA | ACTATCAAGT | GCGTTGTCGT | TATGCAAGTA | ATAGTGATAA | TCCTGTTTTC | 1800 |
| TTTAATGTAG | ATACTGGTGG | AGCGAATCCA | ATTTTCCAAC | AGATAAACTT | TGCATCTACT | 1860 |
| GTAGATAGTA | ATATGGGAGT | AAAAGAAGAA | AATGGCGTCT | ATGTTGTTAA | ATCTATAAAA | 1920 |
| ACGGTAGAAA | TTCCTGCCGG | AAGTTTCTAT | GTGCATGTAA | CAAACCAAGG | TTCTTCAGAT | 1980 |
| CTCTTTTTAG | ATCGTATTGA | GTTTGTTCCA | AAAATCCAAT | TCCAATTCTG | TGATAATAAT | 2040 |
| AATCTTCACT | GTGATTGTAA | TAACCCTGTT | GACACCGATT | GTACATTTTG | TTGCGTTTGC | 2100 |
| ACTAGTCTTA | CTGATTGTGA | TTGTAATAAC | CCTCGTGGCA | TAGATTGTAC | GCTATGTTGT | 2160 |

-continued

```
CAGGTAGAAA ATCAGCTACC TTCTTTTGTG ACACTTACAG ATTTACGAAA TATCACATCC   2220

CAAGTGAATG GTCTATTTGC ACCTGGAACA CAAAATAGGC TGGCTCAAAA TATAAGTGAT   2280

CATGATATTG AAGAAGTTGT ATTGAAAGTG GATGCCTTAT CAGATGAGAT ATTTGGAACA   2340

AATAAGAAGG CTTTACGTAA ATTGGTGAAT CAAGCAAAAC GTTTGAGTAG AGCAAGAAAT   2400

CTTCTGATAG GTGGTAGTTT TGAAAATTGG GATGCATGGT ATAAAGGAAG AAATGTAGTA   2460

ACTGTATCTG ATCATGAACT ATTTAAGAGT GATCATGTAT TATTACCACC ACCAGGATTG   2520

TCTCCATCTT ATATTTTCCA AAAAGTGGAG GAATCTAAAT TAAAAGCAAA TACACGTTAT   2580

ACGGTTTCTG GATTTATTGC GCATGCAACA GATTTAGAAA TTGTGGTTTC TCGTTATGGG   2640

CAAGAAATAA AGAAAGTGGT GCAAGTTCCT TATGGAGAAG CATTCCCATT AACATCAAGT   2700

GGACCAGTTT GTTGTATCCC ACATTCTACA AGTAATGGAA CTTTAGGCAA TCCACATTTC   2760

TTTAGTTACA GTATTGATGT AGGTGCATTA GATGTAGACA CAAACCCTGG TATTGAATTC   2820

GGTCTTCGTA TTGTAAATCC AACTGGAATG GCACGCGTAA GCAATTTGGA AATTCGTGAA   2880

GATCGTCCAT TAGCAGCAAA TGAAATACGA CAAGTACAAC GTGTCGCAAG AAATTGGAGA   2940

ACCGAGTATG AGAAAGAACG TGCGGAAGTA ACAAGTTTAA TTCAACCTGT TATCAATCGA   3000

ATCAACGGAT TGTATGAAAA TGAAAATTGG AACGGTTCTA TTCGTTCAGA TATTTCGTAT   3060

CAGAATATAG ACGCGATTGT ATTACCAACG TTACCAACGT TACGCCATTG GTTTATGTCA   3120

GATAGATTCA GTGAACAAGG AGATATCATG GCTAAATTCC AAGGTGCATT AAATCGTGCG   3180

TATGCACAAC TGGAACAAAG TACGCTTCTG CATAATGGTC ATTTTACAAA AGATGCAGCT   3240

AATTGGACAA TAGAAGGCGA TGCACATCAG ATAACACTAG AAGATGGTAG ACGTGTATTG   3300

CGACTTCCAG ATTGGTCTTC GAGTGTATCT CAAATGATTG AAATCGAGAA TTTTAATCCA   3360

GATAAAGAAT ACAACTTAGT ATTCCATGGG CAAGGAGAAG GAACGGTTAC GTTGGAGCAT   3420

GGAGAAGAAA CAAAATATAT AGAAACGCAT ACACATCATT TTGCGAATTT TACAACTTCT   3480

CAACGTCAAG GACTCACGTT TGAATCAAAT AAAGTGACAG TGACCATTTC TTCAGAAGAT   3540

GGAGAATTCT TAGTGGATAA TATTGCGCTT GTGGAAGCTC CTCTTCCTAC AGATGACCAA   3600

AATTCTGAGG GAAATACGGC TTTCAGTACG AATAGCGATA CAAGTATGAA CAACAATCAA   3660
```

(2) INFORMATION FOR SEQ ID NO:43:

(i) SEQUENCE CHARACTERISTICS:
(A) LENGTH: 1220 amino acids
(B) TYPE: amino acid
(C) STRANDEDNESS: single
(D) TOPOLOGY: linear (ii) MOLECULE TYPE: protein (iii) HYPOTHETICAL: YES (iv) ANTI-SENSE: NO (vi) ORIGINAL SOURCE:
(A) ORGANISM: Bacillus thuringiensis
(C) INDIVIDUAL ISOLATE: 86Q3

(vii) IMMEDIATE SOURCE:
(A) LIBRARY: Lambdagem (TM) - 11 library of Luis Foncerrada
(B) CLONE: 86Q3c (xi) SEQUENCE DESCRIPTION: SEQ ID NO:43:

```
Met Ala Ile Leu Asn Glu Leu Tyr Pro Ser Val Pro Tyr Asn Val Leu
1               5                   10                  15
```

-continued

```
Ala Tyr Thr Pro Pro Ser Phe Leu Pro Asp Ala Gly Thr Gln Ala Thr
             20                  25                  30

Pro Ala Asp Leu Thr Ala Tyr Glu Gln Leu Leu Lys Asn Leu Glu Lys
         35                  40                  45

Gly Ile Asn Ala Gly Thr Tyr Ser Lys Ala Ile Ala Asp Val Leu Lys
     50                  55                  60

Gly Ile Phe Ile Asp Asp Thr Ile Asn Tyr Gln Thr Tyr Val Asn Ile
 65                  70                  75                  80

Gly Leu Ser Leu Ile Thr Leu Ala Val Pro Glu Ile Gly Ile Phe Thr
                 85                  90                  95

Pro Phe Ile Gly Leu Phe Phe Ala Ala Leu Asn Lys His Asp Ala Pro
            100                 105                 110

Pro Pro Pro Asn Ala Lys Asp Ile Phe Glu Ala Met Lys Pro Ala Ile
        115                 120                 125

Gln Glu Met Ile Asp Arg Thr Leu Thr Ala Asp Glu Gln Thr Phe Leu
    130                 135                 140

Asn Gly Glu Ile Ser Gly Leu Gln Asn Leu Ala Ala Arg Tyr Gln Ser
145                 150                 155                 160

Thr Met Asp Asp Ile Gln Ser His Gly Gly Phe Asn Lys Val Asp Ser
                165                 170                 175

Gly Leu Ile Lys Lys Phe Thr Asp Glu Val Leu Ser Leu Asn Ser Phe
            180                 185                 190

Tyr Thr Asp Arg Leu Pro Val Phe Ile Thr Asp Asn Thr Ala Asp Arg
        195                 200                 205

Thr Leu Leu Gly Leu Pro Tyr Tyr Ala Ile Leu Ala Ser Met His Leu
    210                 215                 220

Met Leu Leu Arg Asp Ile Ile Thr Lys Gly Pro Thr Trp Asp Ser Lys
225                 230                 235                 240

Ile Asn Phe Thr Pro Asp Ala Ile Asp Ser Phe Lys Thr Asp Ile Lys
                245                 250                 255

Asn Asn Ile Lys Leu Tyr Ser Lys Thr Ile Tyr Asp Val Phe Gln Lys
            260                 265                 270

Gly Leu Ala Ser Tyr Gly Thr Pro Ser Asp Leu Glu Ser Phe Ala Lys
        275                 280                 285

Lys Lys Lys Tyr Ile Glu Ile Met Thr Thr His Cys Leu Asp Phe Ala
    290                 295                 300

Arg Leu Phe Pro Thr Phe Asp Pro Asp Leu Tyr Pro Thr Gly Ser Gly
305                 310                 315                 320

Asp Ile Ser Leu Gln Lys Thr Arg Arg Ile Leu Ser Pro Phe Ile Pro
                325                 330                 335

Ile Arg Thr Ala Asp Gly Leu Thr Leu Asn Asn Thr Ser Ile Asp Thr
            340                 345                 350

Ser Asn Trp Pro Asn Tyr Glu Asn Gly Asn Gly Ala Phe Pro Asn Pro
        355                 360                 365

Lys Glu Arg Ile Leu Lys Gln Phe Lys Leu Tyr Pro Ser Trp Arg Ala
    370                 375                 380

Gly Gln Tyr Gly Gly Leu Leu Gln Pro Tyr Leu Trp Ala Ile Glu Val
385                 390                 395                 400

Gln Asp Ser Val Glu Thr Arg Leu Tyr Gly Gln Leu Pro Ala Val Asp
                405                 410                 415

Pro Gln Ala Gly Pro Asn Tyr Val Ser Ile Asp Ser Ser Asn Pro Ile
            420                 425                 430
```

```
Ile Gln Ile Asn Met Asp Thr Trp Lys Thr Pro Pro Gln Gly Ala Ser
        435                 440                 445

Gly Trp Asn Thr Asn Leu Met Arg Gly Ser Val Ser Gly Leu Ser Phe
    450                 455                 460

Leu Gln Arg Asp Gly Thr Arg Leu Ser Ala Gly Met Gly Gly Gly Phe
465                 470                 475                 480

Ala Asp Thr Ile Tyr Ser Leu Pro Ala Thr His Tyr Leu Ser Tyr Leu
            485                 490                 495

Tyr Gly Thr Pro Tyr Gln Thr Ser Asp Asn Tyr Ser Gly His Val Gly
                500                 505                 510

Ala Leu Val Gly Val Ser Thr Pro Gln Glu Ala Thr Leu Pro Asn Ile
            515                 520                 525

Ile Gly Gln Pro Asp Glu Gln Gly Asn Val Ser Thr Met Gly Phe Pro
        530                 535                 540

Phe Glu Lys Ala Ser Tyr Gly Gly Thr Val Val Lys Glu Trp Leu Asn
545                 550                 555                 560

Gly Ala Asn Ala Met Lys Leu Ser Pro Gly Gln Ser Ile Gly Ile Pro
                565                 570                 575

Ile Thr Asn Val Thr Lys His Asn Tyr Gln Val Arg Cys Arg Tyr Ala
            580                 585                 590

Ser Asn Ser Asp Asn Pro Val Phe Phe Asn Val Asp Thr Gly Gly Ala
        595                 600                 605

Asn Pro Ile Phe Gln Gln Ile Asn Phe Ala Ser Thr Val Asp Ser Asn
610                 615                 620

Met Gly Val Lys Glu Glu Asn Gly Val Tyr Val Val Lys Ser Ile Lys
625                 630                 635                 640

Thr Val Glu Ile Pro Ala Gly Ser Phe Tyr Val His Val Thr Asn Gln
                645                 650                 655

Gly Ser Ser Asp Leu Phe Leu Asp Arg Ile Glu Phe Val Pro Lys Ile
                660                 665                 670

Gln Phe Gln Phe Cys Asp Asn Asn Leu His Cys Asp Cys Asn Asn
            675                 680                 685

Pro Val Asp Thr Asp Cys Thr Phe Cys Cys Val Cys Thr Ser Leu Thr
            690                 695                 700

Asp Cys Asp Cys Asn Asn Pro Arg Gly Ile Asp Cys Thr Leu Cys Cys
705                 710                 715                 720

Gln Val Glu Asn Gln Leu Pro Ser Phe Val Thr Leu Thr Asp Leu Arg
                725                 730                 735

Asn Ile Thr Ser Gln Val Asn Gly Leu Phe Ala Pro Gly Thr Gln Asn
                740                 745                 750

Arg Leu Ala Gln Asn Ile Ser Asp His Asp Ile Glu Glu Val Val Leu
            755                 760                 765

Lys Val Asp Ala Leu Ser Asp Glu Ile Phe Gly Thr Asn Lys Lys Ala
            770                 775                 780

Leu Arg Lys Leu Val Asn Gln Ala Lys Arg Leu Ser Arg Ala Arg Asn
785                 790                 795                 800

Leu Leu Ile Gly Gly Ser Phe Glu Asn Trp Asp Ala Trp Tyr Lys Gly
                805                 810                 815

Arg Asn Val Val Thr Val Ser Asp His Glu Leu Phe Lys Ser Asp His
            820                 825                 830

Val Leu Leu Pro Pro Gly Leu Ser Pro Ser Tyr Ile Phe Gln Lys
            835                 840                 845

Val Glu Glu Ser Lys Leu Lys Ala Asn Thr Arg Tyr Thr Val Ser Gly
```

-continued

```
            850                 855                 860
Phe Ile Ala His Ala Thr Asp Leu Glu Ile Val Ser Arg Tyr Gly
865                 870                 875                 880

Gln Glu Ile Lys Lys Val Val Gln Val Pro Tyr Gly Glu Ala Phe Pro
                885                 890                 895

Leu Thr Ser Ser Gly Pro Val Cys Cys Ile Pro His Ser Thr Ser Asn
                900                 905                 910

Gly Thr Leu Gly Asn Pro His Phe Phe Ser Tyr Ser Ile Asp Val Gly
                915                 920                 925

Ala Leu Asp Val Asp Thr Asn Pro Gly Ile Glu Phe Gly Leu Arg Ile
930                 935                 940

Val Asn Pro Thr Gly Met Ala Arg Val Ser Asn Leu Glu Ile Arg Glu
945                 950                 955                 960

Asp Arg Pro Leu Ala Ala Asn Glu Ile Arg Gln Val Gln Arg Val Ala
                965                 970                 975

Arg Asn Trp Arg Thr Glu Tyr Glu Lys Glu Arg Ala Glu Val Thr Ser
                980                 985                 990

Leu Ile Gln Pro Val Ile Asn Arg Ile Asn Gly Leu Tyr Glu Asn Glu
                995                 1000                1005

Asn Trp Asn Gly Ser Ile Arg Ser Asp Ile Ser Tyr Gln Asn Ile Asp
                1010                1015                1020

Ala Ile Val Leu Pro Thr Leu Pro Thr Leu Arg His Trp Phe Met Ser
1025                1030                1035                1040

Asp Arg Phe Ser Glu Gln Gly Asp Ile Met Ala Lys Phe Gln Gly Ala
                1045                1050                1055

Leu Asn Arg Ala Tyr Ala Gln Leu Glu Gln Ser Thr Leu Leu His Asn
                1060                1065                1070

Gly His Phe Thr Lys Asp Ala Ala Asn Trp Thr Ile Glu Gly Asp Ala
                1075                1080                1085

His Gln Ile Thr Leu Glu Asp Gly Arg Arg Val Leu Arg Leu Pro Asp
                1090                1095                1100

Trp Ser Ser Ser Val Ser Gln Met Ile Glu Ile Glu Asn Phe Asn Pro
1105                1110                1115                1120

Asp Lys Glu Tyr Asn Leu Val Phe His Gly Gln Gly Glu Gly Thr Val
                1125                1130                1135

Thr Leu Glu His Gly Glu Glu Thr Lys Tyr Ile Glu Thr His Thr His
                1140                1145                1150

His Phe Ala Asn Phe Thr Thr Ser Gln Arg Gln Gly Leu Thr Phe Glu
                1155                1160                1165

Ser Asn Lys Val Thr Val Thr Ile Ser Ser Glu Asp Gly Glu Phe Leu
                1170                1175                1180

Val Asp Asn Ile Ala Leu Val Glu Ala Pro Leu Pro Thr Asp Asp Gln
1185                1190                1195                1200

Asn Ser Glu Gly Asn Thr Ala Phe Ser Thr Asn Ser Asp Thr Ser Met
                1205                1210                1215

Asn Asn Asn Gln
                1220
```

(2) INFORMATION FOR SEQ ID NO:44:

(i) SEQUENCE CHARACTERISTICS:
        (A) LENGTH: 16 amino acids
        (B) TYPE: amino acid
        (C) STRANDEDNESS: single
        (D) TOPOLOGY: linear

```
    (ii) MOLECULE TYPE: peptide (xi) SEQUENCE DESCRIPTION: SEQ ID NO:44:

Ala Asn Thr Thr Gln Ser Phe His Phe Ser Asn Ile Leu Asp Tyr Lys
1               5                   10                  15

(2) INFORMATION FOR SEQ ID NO:45:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:45:

TTTCATTTTT CWAATATTTT AGATTATAAA                                    30

(2) INFORMATION FOR SEQ ID NO:46:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

Gly Ile Gly Phe Glu Leu Asp Thr Tyr Ala Asn Ala Pro Glu Asp Glu
1               5                   10                  15

Val (2) INFORMATION FOR SEQ ID NO:47:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

Ala Ala Ser Asp Tyr Ile Asp Pro Ile Phe
1               5                   10

(2) INFORMATION FOR SEQ ID NO:48:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:48:

GCAGGATCCG ATTATATTWG ATATWAVTCC                                    30

(2) INFORMATION FOR SEQ ID NO:49:

(i) SEQUENCE CHARACTERISTICS:
        (A) LENGTH: 40 bases
        (B) TYPE: nucleic acid
        (C) STRANDEDNESS: single
```

(D) TOPOLOGY: linear (ii) MOLECULE TYPE: DNA (synthetic)

(xi) SEQUENCE DESCRIPTION: SEQ ID NO:49:

GCGGCCGCAC TTCATCTTCW GGWGCATTWG CATAWGTATC        40

(2) INFORMATION FOR SEQ ID NO:50:

(i) SEQUENCE CHARACTERISTICS:
        (A) LENGTH: 2172 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

| | | | | | |
|---|---|---|---|---|---|
| ATGAAAGAAC | AAAATCTAAA | TAAATATGAT | GAAATAACTG | TACAAGCAGC | AAGCGATTAT | 60 |
| ATCGACATTC | GTCCGATTTT | TCAAACAAAT | GGATCTGCTA | CATTTAATTC | TAATACCAAT | 120 |
| ATTACAACTT | TAACACAAGC | TATAAATAGT | CAAGCAGGAG | CAATTGCAGG | AAAGACTGCT | 180 |
| CTAGATATGA | GACATGACTT | TACTTTTAGA | GCAGATATTT | TTCTTGGAAC | TAAAAGTAAC | 240 |
| GGAGCAGACG | GTATTGCAAT | CGCATTTCAT | AGAGGATCAA | TTGGGTTTGT | TGGAACAAAA | 300 |
| GGCGGAGGAC | TTGGAATATT | AGGTGCACCT | AAAGGGATAG | GGTTTGAATT | AGACACATAT | 360 |
| GCGAATGCAC | CTGAGGACGA | AGTAGGCGAT | TCGTTTGGGC | ATGGGGCAAT | GAAAGGATCA | 420 |
| TTCCCTAGTT | TCCCAAATGG | ATATCCCCAT | GCTGGCTTTG | TAAGTACTGA | TAAAAATAGT | 480 |
| AGATGGTTAT | CAGCTCTAGC | TCAGATGCAG | CGAATCGCTG | CTCCAAACGG | GCGTTGGAGA | 540 |
| CGTCTGGAGA | TTCGTTGGGA | TGCTCGTAAT | AAAGAGTTAA | CTGCAAATCT | TCAGGATTTA | 600 |
| ACTTTTAATG | ACATAACTGT | TGGAGAGAAG | CCACGTACTC | AAGAACTGC | AACTTGGAGG | 660 |
| TTAGTAAATC | CTGCATTTGA | ACTTGATCAG | AAGTATACTT | TTGTTATTGG | TTCGGCGACG | 720 |
| GGTGCATCTA | ATAACCTACA | TCAGATTGGG | ATTATAGAAT | TTGATGCATA | CTTTACTAAA | 780 |
| CCGACAATAG | AAGCGAATAA | TGTAAATGTC | CCAGTGGGAG | CAACATTTAA | TCCAAAAACA | 840 |
| TATCCAGGAA | TAAATTTAAG | AGCAACAGAT | GAGATAGATG | GGGATTTGAC | ATCGAAGATT | 900 |
| ATTGTGAAAG | CAAACAATGT | TAATACGTCG | AAAACGGGTG | TGTATTATGT | GACGTATTAT | 960 |
| GTAGAGAATA | GTTATGGGGA | AAGTGATGAA | AAAACAATCG | AAGTAACTGT | GTTTTCAAAC | 1020 |
| CCTACAATTA | TTGCAAGTGA | TGTTGAAATT | GAAAAAGGGG | AATCTTTTAA | CCCACTAACT | 1080 |
| GATTCAAGAG | TAGGTCTTTC | TGCACAGGAT | TCATTAGGCA | ATGATATTAC | CCAAAATGTA | 1140 |
| AAGGTAAAAT | CGAGTAATGT | GGATACTTCA | AGCCAGGGG | AATATGAAGT | TGTATTTGAA | 1200 |
| GTGACAGATA | GCTTTGGTGG | AAAAGCAGAA | AAAGATTTCA | AGGTTACAGT | TTTAGGACAG | 1260 |
| CCAAGTATAG | AAGCGAATAA | TGTTGAATTA | GAAATAGATG | ATTCATTGGA | TCCATTAACA | 1320 |
| GATGCAAAAG | TAGGTCTCCG | TGCAAAGGAT | TCATTAGGTA | ATGATATTAC | GAAAGACATA | 1380 |
| AAAGTAAAGT | TCAATAACGT | AGATACTTCA | AATTCAGGAA | AGTATGAAGT | TATATTTGAA | 1440 |
| GTGACGGACC | GTTTTGGAAA | AAAAGCAGAA | AAAGTATTG | AAGTCCTTGT | TCTAGGAGAA | 1500 |
| CCAAGCATTG | AAGCAAATGA | TGTTGAGGTT | AATAAAGGTG | AAACGTTTGA | ACCATTAACA | 1560 |
| GATTCAAGAG | TTGGCCTCCG | TGCAAAAGAC | TCATTAGGTA | ATGATATTAC | GAAAGATGTG | 1620 |
| AAAATAAAT | CAAGTAATGT | GGATACTTCA | AAACCAGGTG | AATATGAAGT | TGTATTTGAA | 1680 |
| GTGACAGATC | GTTTTGGTAA | ATATGTAGAA | AAAACAATTG | GAGTTATAGT | GCCAGTAATT | 1740 |

```
GATGATGAAT GGGAAGATGG AAATGTGAAT GGTTGGAAAT TCTATGCTGG GCAAGATATT    1800

AAACTGTTGA AGGATCCTGA TAAAGCCTAT AAAGGCGATT ATGTATTCTA TGATTCTAGA    1860

CACGTTGCTA TTTCTAAAAC AATTCCACTA ACGGATTTGC AAATAAATAC AAACTATGAA    1920

ATTACAGTGT ATGCTAAAGC AGAAAGCGGC GATCATCACT TAAAAGTGAC GTATAAGAAA    1980

GACCCGGCAG GTCCAGAAGA GCCGCCAGTT TTCAATAGAC TGATTAGCAC AGGCACATTG    2040

GTAGAAAAAG ATTATAGAGA ATTAAAAGGG ACGTTCCGCG TAACAGAATT AAACAAAGCA    2100

CCATTGATAA TCGTAGAGAA TTTTGGAGCT GGATATATAG GTGGAATTAG AATTGTGAAA    2160

ATATCGTAAT AA                                                        2172
```

(2) INFORMATION FOR SEQ ID NO:51:

(i) SEQUENCE CHARACTERISTICS:
 (A) LENGTH: 722 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:51:

```
Met Lys Glu Gln Asn Leu Asn Lys Tyr Asp Glu Ile Thr Val Gln Ala
1               5                   10                  15

Ala Ser Asp Tyr Ile Asp Ile Arg Pro Ile Phe Gln Thr Asn Gly Ser
            20                  25                  30

Ala Thr Phe Asn Ser Asn Thr Asn Ile Thr Thr Leu Thr Gln Ala Ile
        35                  40                  45

Asn Ser Gln Ala Gly Ala Ile Ala Gly Lys Thr Ala Leu Asp Met Arg
    50                  55                  60

His Asp Phe Thr Phe Arg Ala Asp Ile Phe Leu Gly Thr Lys Ser Asn
65                  70                  75                  80

Gly Ala Asp Gly Ile Ala Ile Ala Phe His Arg Gly Ser Ile Gly Phe
                85                  90                  95

Val Gly Thr Lys Gly Gly Gly Leu Gly Ile Leu Gly Ala Pro Lys Gly
            100                 105                 110

Ile Gly Phe Glu Leu Asp Thr Tyr Ala Asn Ala Pro Glu Asp Glu Val
        115                 120                 125

Gly Asp Ser Phe Gly His Gly Ala Met Lys Gly Ser Phe Pro Ser Phe
    130                 135                 140

Pro Asn Gly Tyr Pro His Ala Gly Phe Val Ser Thr Asp Lys Asn Ser
145                 150                 155                 160

Arg Trp Leu Ser Ala Leu Ala Gln Met Gln Arg Ile Ala Ala Pro Asn
                165                 170                 175

Gly Arg Trp Arg Arg Leu Glu Ile Arg Trp Asp Ala Arg Asn Lys Glu
            180                 185                 190

Leu Thr Ala Asn Leu Gln Asp Leu Thr Phe Asn Asp Ile Thr Val Gly
        195                 200                 205

Glu Lys Pro Arg Thr Pro Arg Thr Ala Thr Trp Arg Leu Val Asn Pro
    210                 215                 220

Ala Phe Glu Leu Asp Gln Lys Tyr Thr Phe Val Ile Gly Ser Ala Thr
225                 230                 235                 240

Gly Ala Ser Asn Asn Leu His Gln Ile Gly Ile Ile Glu Phe Asp Ala
                245                 250                 255

Tyr Phe Thr Lys Pro Thr Ile Glu Ala Asn Asn Val Asn Val Pro Val
            260                 265                 270
```

-continued

```
Gly Ala Thr Phe Asn Pro Lys Thr Tyr Pro Gly Ile Asn Leu Arg Ala
        275                 280                 285

Thr Asp Glu Ile Asp Gly Asp Leu Thr Ser Lys Ile Ile Val Lys Ala
290                 295                 300

Asn Asn Val Asn Thr Ser Lys Thr Gly Val Tyr Tyr Val Thr Tyr Tyr
305                 310                 315                 320

Val Glu Asn Ser Tyr Gly Glu Ser Asp Glu Lys Thr Ile Glu Val Thr
                325                 330                 335

Val Phe Ser Asn Pro Thr Ile Ile Ala Ser Asp Val Glu Ile Glu Lys
            340                 345                 350

Gly Glu Ser Phe Asn Pro Leu Thr Asp Ser Arg Val Gly Leu Ser Ala
        355                 360                 365

Gln Asp Ser Leu Gly Asn Asp Ile Thr Gln Asn Val Lys Val Lys Ser
    370                 375                 380

Ser Asn Val Asp Thr Ser Lys Pro Gly Tyr Glu Val Val Phe Glu
385                 390                 395                 400

Val Thr Asp Ser Phe Gly Gly Lys Ala Glu Lys Asp Phe Lys Val Thr
                405                 410                 415

Val Leu Gly Gln Pro Ser Ile Glu Ala Asn Asn Val Glu Leu Glu Ile
            420                 425                 430

Asp Asp Ser Leu Asp Pro Leu Thr Asp Ala Lys Val Gly Leu Arg Ala
        435                 440                 445

Lys Asp Ser Leu Gly Asn Asp Ile Thr Lys Asp Ile Lys Val Lys Phe
    450                 455                 460

Asn Asn Val Asp Thr Ser Asn Ser Gly Lys Tyr Glu Val Ile Phe Glu
465                 470                 475                 480

Val Thr Asp Arg Phe Gly Lys Lys Ala Glu Lys Ser Ile Glu Val Leu
                485                 490                 495

Val Leu Gly Glu Pro Ser Ile Glu Ala Asn Asp Val Glu Val Asn Lys
            500                 505                 510

Gly Glu Thr Phe Glu Pro Leu Thr Asp Ser Arg Val Gly Leu Arg Ala
        515                 520                 525

Lys Asp Ser Leu Gly Asn Asp Ile Thr Lys Asp Val Lys Ile Lys Ser
    530                 535                 540

Ser Asn Val Asp Thr Ser Lys Pro Gly Glu Tyr Glu Val Val Phe Glu
545                 550                 555                 560

Val Thr Asp Arg Phe Gly Lys Tyr Val Glu Lys Thr Ile Gly Val Ile
                565                 570                 575

Val Pro Val Ile Asp Asp Glu Trp Glu Asp Gly Asn Val Asn Gly Trp
            580                 585                 590

Lys Phe Tyr Ala Gly Gln Asp Ile Lys Leu Leu Lys Asp Pro Asp Lys
    595                 600                 605

Ala Tyr Lys Gly Asp Tyr Val Phe Tyr Asp Ser Arg His Val Ala Ile
610                 615                 620

Ser Lys Thr Ile Pro Leu Thr Asp Leu Gln Ile Asn Thr Asn Tyr Glu
625                 630                 635                 640

Ile Thr Val Tyr Ala Lys Ala Glu Ser Gly Asp His His Leu Lys Val
                645                 650                 655

Thr Tyr Lys Lys Asp Pro Ala Gly Pro Glu Pro Pro Val Phe Asn
            660                 665                 670

Arg Leu Ile Ser Thr Gly Thr Leu Val Glu Lys Asp Tyr Arg Glu Leu
    675                 680                 685
```

```
                                            -continued

Lys Gly Thr Phe Arg Val Thr Glu Leu Asn Lys Ala Pro Leu Ile Ile
    690                 695                 700

Val Glu Asn Phe Gly Ala Gly Tyr Ile Gly Gly Ile Arg Ile Val Lys
705                 710                 715                 720

Ile Ser
```

BACILLUS THURINGIENSIS TOXINS ACTIVE AGAINST HYMENOPTERAN PESTS

CROSS-REFERENCE TO A RELATED APPLICATION

This is a division of co-pending application Ser. No. 08/611,928, filed Mar. 6, 1996; which is a continuation of application Ser. No. 08/158,232, filed Nov. 24, 1993 (now U.S. Pat. No. 5,596,071); which is a continuation-in-part of application Ser. No. 07/887,980, filed on May 22, 1992 (now abandoned); which is a continuation-in-part of application Ser. No. 07/703,977, filed on May 22, 1991 (now U.S. Pat. No. 5,260,058) and a continuation-in-part of application Ser. No. 07/797,645, filed on Nov. 25, 1991 (now U.S. Pat. No. 5,268,297).

BACKGROUND OF THE INVENTION

The development of biological control agents as alternatives to chemical insecticides for the control of important pest species is a subject of increasing interest. Concerns for the environment and exposure of man to harmful substances in air, food and water have stimulated legislation and restrictions regarding the use of chemical pesticides, particularly for pests found in the urban environment. Control of insect pests in urban areas is highly desirable but exposure to chemical pesticides in the household and from lawns and gardens is of great concern to the public. If given a choice, most people would prefer to use a non-toxic biological control agent rather than a toxic chemical to control insects in the urban environment. The problem is that very few biological alternatives to chemical insecticides are available for purchase and use by the public.

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] *TIBTECH*6:S4–S7). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystal called a δ-endotoxin which is toxic to the larvae of a number of lepidopteran insects.

In recent years, however, investigators have discovered *B.t.* pesticides with specificities for a much broader range of pests. For example, other species of *B.t.*, namely *israelensis* and *tenebrionis* (a.k.a. *B.t.* M-7, a.k.a. *B.t. san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensis*," *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of *B.t.* have been identified, and genes responsible for active δ-endotoxin proteins have been isolated (Höfte, H., H. R. Whiteley [1989] *Microbiological Reviews* 52(2):242–255). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a *B.t.* crystal protein gene in *Escherichia coli* has been described in the published literature (Schnepf, H. E., H. R. Whitely [1981] *Proc. Natl. Acad. Sci. USA* 78:2893–2897). U.S. Pat. No. 4,448,885 and U.S. Pat. No. 4,467,036 both disclose the expression of *B.t.* crystal protein in *E. coli*. U.S. Pat. Nos. 4,797,276 and 4,853,331 disclose *B. thuringiensis* strain *san diego* (a.k.a. *B.t. tenebrionis*, a.k.a. M-7) which can be used to control coleopteran pests in various environments. U.S. Pat. No. 4,918,006 discloses *B.t.* toxins having activity against Dipterans. U.S. Pat. No. 4,849,217 discloses *B.t.* isolates which have activity against the alfalfa weevil. U.S. Pat. No. 5,208,077 discloses coleopteran-active *Bacillus thuringiensis* isolates. U.S. Pat. No. 5,151,363 and U.S. Pat. No. 4,948,734 disclose certain isolates of *B.t.* which have activity against nematodes. As a result of extensive research and investment of resources, other patents have issued for new *B.t.* isolates and new uses of *B.t.* isolates. However, the discovery of new *B.t.* isolates and new uses of known *B.t.* isolates remains an empirical, unpredictable art.

Ants comprise a large group of insects (family Formicidae) from the taxonomic order, Hymenoptera. They are among the most common house pests. In many situations, ants are a nuisance pest. Foraging ants create problems with hygiene in hospitals and the food industry. Ants also create problems in agriculture. Damage can be caused by direct feeding on plants. Harvester and fire ants are commonly associated with this type of damage (Holldobler, B., E. O. Wilson [1990] *The Ants*, Belkap Press, Cambridge, Mass. 732 pp.) Some ants cause indirect damage by nurturing and protecting sap feeding insects such as mealybugs and aphids. Ants, particularly in the genus Solenopsis are capable of producing extremely painful stings to humans. It has been estimated that approximately 10,000 stings occur each year (Habermehl, G. G. [1981] *Venomous Animals and Their Toxins*, Springer-Verlag, N.Y., 195 pp.). The pharaoh ant (*Monomorium pharaonis*) is primarily an urban pest. However, this species can also be an agricultural pest and damage to corn has been noted (Ebeling, W. [1978] *Urban Entomology*, UC Press, Berkeley, Calif., 695 pp.).

Carpenter ants, Camponotus spp., are distributed throughout North America. Some of the more common and/or studied species include *C. modoc* in the Pacific Northwest, *C. clarithorax* in southern California, and the black, red, and Florida carpenter ants, *C. pennsylvanicus, C. noveboracensis* and *C. abdominalis*, respectively, in the east (Ebeling, W. [1978] *Urban Entomology, Univ. Calif.: Berkeley p.*

209–213). Public concern over carpenter ants has been increasing due to the greater probability of structural infestations as suburban developments extend into the forest habitats of the ants.

Pestiferous species of carpenter ants may be considered nuisance pests because of their foraging activity inside homes. More significant damage occurs when carpenter ants extend their nests into sound wood. Nesting sites may be located in live and dead trees, sometimes resulting in damage to shade trees. Nests may also be established in walls and support beams of structures, or in voids within doors, walls, and furniture. Preference for moist or decaying wood has been reported, but nesting sites are not restricted to such areas. Carpenter ant populations develop relatively slowly with colonies of 300–2,000 workers being produced over a 2-year or longer period for various species. The presence of reproductives follows this slow development since their production has been reported only from well established colonies (Hansen, L. D., R. D. Akre [1985] Biology of carpenter ants in Washington state (Hymenoptera:Formicidae:Camponotus). Melanderia43. 62 p.; Pricer, J. L. [1908] Biol. Bull. 14:177–218). Despite the slow colony growth, large colonies with satellite colonies have been found. Worker movement occurs between the main colony and the satellites, which serve as areas for further brood development and colony expansion (Hansen and Akre [1985], supra).

Current methods for controlling structural infestations of carpenter ants include sanitation of potential and current nest sites, minimizing access to structures (eg. preventing the contact of tree branches with a structure), and the application of insecticides to repel (perimeter spray barriers) and/or eliminate carpenter ants. The use of boric acid dust in dry, wall voids is reported to be effective for up to 20 years (Hansen and Akre, supra).

Recommendations for the chemical control of established structural infestations in the home are often accompanied with warnings of possible hazards to the applicator as well as children and pets. Alternative control methods such as effective biological control agents have not been found (Akre, R. D., L. D. Hansen, A. L. Antonelli [1989] Ext. Bull. Washington State Univ. Coop. Ext. Serv. 1989 rev. no. EB 0818, 6 pp.). A need clearly exists for a safe, effective biological control agent for carpenter ants.

Pharaoh ants, *Monomorium pharaonis*, have been described as " . . . the most persistent and difficult of all our house-infesting ants to control or eradicate" (Smith, M. R. [1965] USDA-ARS Tech. Bull. No. 1326, 105 pp.). It is a tropical species which has extended its range to more temperate regions by establishing colonies in heated buildings. Pharaoh ants frequently infests buildings where food is prepared, and have been found to carry pathogenic organisms (Beatson, S. H. [1972] Lancet 1:425–427).

The difficulty in controlling pharaoh ants may be attributed to their inaccessible nesting sites, rapid population growth, and dispersion of colonies. Their small size allows establishment of colonies in any suitable location, including unusual places such as between books and in stored clothing. With multiple queen colonies, and the warm (30° C.), humid (63–80% RH) conditions that favor pharaoh ants, large colonies can develop rapidly. Portions of these large colonies may disperse to form new colonies at any time, probably in response to overcrowding and unfavorable microenvironmental conditions. Unlike other ant species, pharaoh ants do not exhibit intercolony aggression. This permits the adoption of ants from other colonies and may further enhance the establishment of new colonies and reinfestations. Pharaoh ants also forage for food more than 35 m from the nest without distinct trail following, and thus make nests difficult to find and eradicate.

Control methods for pharaoh ants emphasize the use of insect growth regulators (IGR) or toxicants incorporated into baits. Properly implemented bait programs are effective, however it may take over a month to achieve control. Insecticide applications, while fast acting, usually do not eliminate colonies, and may be unacceptable in certain areas where toxic residues are a concern. In addition, insecticide applications are generally not compatible with bait programs.

A need exists for safe and effective biological control agents for pharaoh ants.

BRIEF SUMMARY OF THE INVENTION

The subject invention concerns novel *Bacillus thuringiensis* (*B.t.*) isolates and genes therefrom which encode novel hymenopteran-activeproteins. The novel *B.t.* isolates, known herein as *Bacillus thuringiensis* PS140E2 (*B.t.* PS140E2), *Bacillus thuringiensis* PS86Q3 (*B.t.* PS86Q3) and *Bacillus thuringiensis* PS211B2 (*B.t.* PS211B2), as well as toxins from these isolates, can be used to control pests such as fire ants, carpenter ants, argentine ants, and pharaoh ants.

The subject invention also includes mutants of the above isolates which have substantially the same pesticidal properties as the parent isolate. Procedures for making mutants are well known in the microbiological art. Ultraviolet light and nitrosoguanidine are used extensively toward this end.

The subject invention also concerns novel toxins active against ants. A further aspect of the invention concerns genes encoding these formicidal toxins. The subject invention provides the person skilled in this art with a vast array of formicidal toxins, methods for using these toxins, and genes that encode the toxins. The genes or gene fragments of the invention encode *Bacillus thuringiensis* δ-endotoxins which have hymenopteran activity. The genes or gene fragments can be transferred to suitable hosts via a recombinant DNA vector.

One aspect of the invention is the discovery of a generalized chemical formula common to a wide range of formicidal toxins. This formula can be used by those skilled in this art to obtain and identify a wide variety of toxins having the desired formicidal activity. The subject invention provides other teachings which enable the skilled practitioner to identify and isolate ant-active toxins and the genes which code therefor. For example, characteristic features of ant-active toxin crystals are disclosed herein. Furthermore, characteristic levels of amino acid homology can be used to characterize the toxins of the subject invention. Yet another characterizing feature pertains to immunoreactivity of the toxins with certain antibodies. Also, nucleotide probes specific for genes encoding toxins with formicidal activity are described. Thus, the identification of toxins of the subject invention can be accomplished by sequence-specific motifs, overall sequence similarity, immunoreactivity, and ability to hybridize with specific probes.

In addition to the teachings of the subject invention which broadly define *B.t.* toxins with advantageous formicidal activity, a further aspect of the subject invention is the provision of specific formicidal toxins and the nucleotide sequences which encode these toxins. Examples of such specific toxins are the gene expression products of isolate PS86Q3.

BRIEF DESCRIPTION OF THE DRAWINGS

FIG. 1 is a photograph of a standard SDS polyacrylamide gel of B.t. PS140E2, and B.t. PS86Q3.

FIG. 2 is a photograph of a standard SDS polyacrylamide gel showing alkali-soluble proteins of B.t. PS211B2 compared to a protein standard.

FIG. 4 is B.t. PS86Q3; and FIG. 5 is B.t. PS211B2). Cells were embedded in an epoxy resin and stained with uranyl acetate and lead citrate.

BRIEF DESCRIPTION OF THE SEQUENCES

Figure 3:
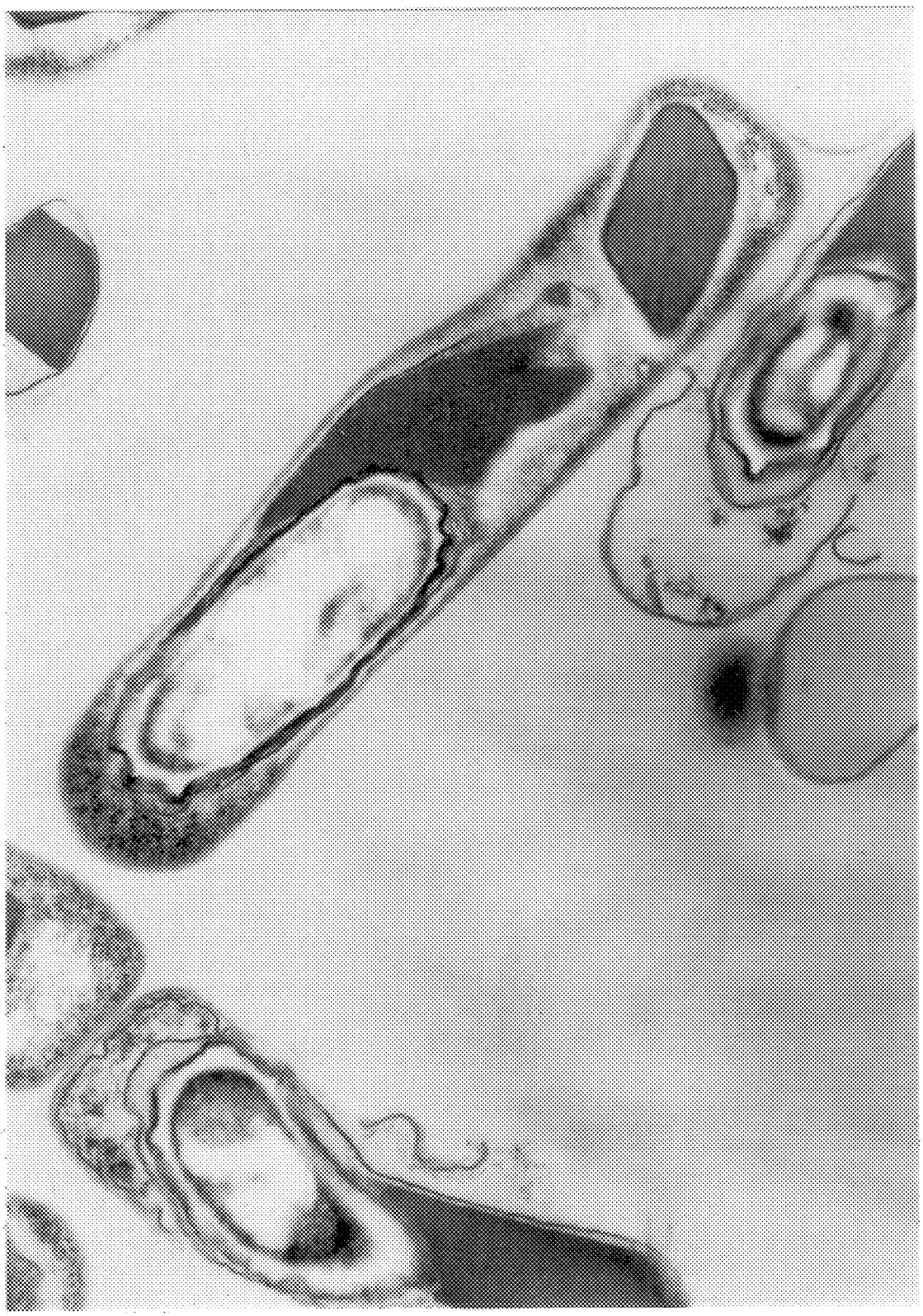
FIGS. 3–5 are transmission electron micrographs of ultrathin sections of the ant-active B.t. strains (FIG. 3 is B.t. PS140E2.

SEQ ID NO. 1 is the nucleotide sequence of gene 17a.

SEQ ID NO. 2 is the amino acid sequence of protein 17a.

SEQ ID NO. 3 is the nucleotide sequence of gene 17b.

SEQ ID NO. 4 is the amino acid sequence of protein 17b.

SEQ ID NO. 5 is the nucleotide sequence of gene 33F2.

SEQ ID NO. 6 is the amino acid sequence of protein 33F2.

SEQ ID NO. 7 is the nucleotide sequence of gene 86Q3a.

SEQ ID NO. 8 is the amino acid sequence of protein 86Q3a.

SEQ ID NO. 9 is the nucleotide sequence of gene 63B.

SEQ ID NO. 10 is the amino acid sequence of protein 63B.

SEQ ID NO. 11 is the amino acid sequence of a probe which can be used according to the subject invention.

SEQ ID NO. 12 is DNA coding for the amino acid sequence of SEQ ID NO. 11.

SEQ ID NO. 13 is DNA coding for the amino acid sequence of SEQ ID NO. 11.

SEQ ID NO. 14 is the amino acid sequence of a probe which can be used according to the subject invention.

SEQ ID NO. 15 is DNA coding for the amino acid sequence of SEQ ID NO. 14.

SEQ ID NO. 16 is DNA coding for the amino acid sequence of SEQ ID NO. 14.

SEQ ID NO. 17 is the N-terminal amino acid sequence of 17a.

SEQ ID NO. 18 is the N-terminal amino acid sequence of 17b.

SEQ ID NO. 19 is the N-terminal amino acid sequence of 86Q3a.

SEQ ID NO. 20 is the N-terminal amino acid sequence of 63B.

SEQ ID NO. 21 is the N-terminal amino acid sequence of 33F2.

SEQ ID NO. 22 is an internal amino acid sequence for 63B.

SEQ ID NO. 23 is a synthetic oligonucleotide derived from 17.

SEQ ID NO. 24 is the forward oligonucleotide primer from 63B.

SEQ ID NO. 25 is the reverse oligonucleotide primer from 63B.

SEQ ID NO. 26 is oligonucleotide probe 33F2A.

SEQ ID NO. 27 is oligonucleotide probe 33F2B.

SEQ ID NO. 28 is a reverse primer used according to the subject invention.

SEQ ID NO. 29 is an oligonucleotide derived from the N-terminal amino acid sequence of 86Q3a (SEQ ID NO. 19).

SEQ ID NO. 30 is the amino acid sequence coded for by an oligonucleotide used according to the subject invention (SEQ ID NO. 31).

SEQ ID NO. 31 is an oligonucleotide which codes for the amino acid sequence of SEQ ID NO. 30.

SEQ ID NO. 32 is the amino acid sequence coded for by the oligonucleotide of SEQ ID NO. 33.

SEQ ID NO. 33 is a DNA sequence coding for the peptide of SEQ ID NO. 32.

SEQ ID NO. 34 is the reverse complement primer to SEQ ID NO. 38, used according to the subject invention.

SEQ ID NO. 35 is a forward primer according to the subject invention.

SEQ ID NO. 36 is an amino acid sequence according to the subject invention.

SEQ ID NO. 37 is a reverse primer according to the subject invention.

SEQ ID NO. 38 is the nematode (NEMI) variant of region 5 of Höfte and Whiteley.

SEQ ID NO. 39 is the Generic Formula of the subject invention.

SEQ ID NO. 40 is an oligonucleotide derived from the N-terminal amino acid sequence of 86Q3c.

SEQ ID NO. 41 is the "protoxin T" oligonucleotide used as the reverse 3' primer.

SEQ ID NO. 42 is the nucleotide sequence of gene 86Q3c.

SEQ ID NO. 43 is the amino acid sequence of protein 86Q3c.

SEQ ID NO. 44 is the N-terminal amino acid sequence of 140E2.

SEQ ID NO. 45 is an oligonucleotide probe derived from the 35 kDa toxin of PS140E2.

SEQ ID NO. 46 is an internal amino acid sequence of 211B2.

SEQ ID NO. 47 is an N-terminal amino acid sequence of 211B2.

SEQ ID NO. 48 is a forward oligonucleotide primer used according to the subject invention.

SEQ ID NO. 49 is a reverse oligonucleotide primer used according to the subject invention.

SEQ ID NO. 50 is the nucleotide sequence of 211B2.

SEQ ID NO. 51 is the amino acid sequence of 211B2.

DETAILED DISCLOSURE OF THE INVENTION

One aspect of the subject invention is the discovery of Bacillus thuringiensis isolates having activity against ants.

A comparison of the characteristics of the Bacillus thuringiensis isolates of the subject invention is shown in Table 1.

TABLE 1

Comparison of *B.t.* PS140E2, *B.t.* PS86Q3, and *B.t.* PS211B2

|  | *B.t.* PS140E2 | *B.t.* PS86Q3 | *B.t.* PS211B2 |
|---|---|---|---|
| Inclusions: | Ellipse and 2 small inclusions | 1 long and 1 or 2 small inclusions | Large amorphic |
| Approximate molecular wt. of proteins by SDS-PAGE | 78,000 | 155,000 | 175,000 |
|  | 70,000 | 135,000 | 130,000 |
|  | 35,000 | 98,000 | 100,000 |
|  |  | 62,000 | 83,000 |
|  |  | 58,000 | 69,000 |
|  |  |  | 43,000 |
|  |  |  | 40,000 |
|  |  |  | 36,000 |
|  |  |  | 35,000 |
|  |  |  | 34,000 |
|  |  |  | 27,000 |
| Host range | Hymenoptera | Hymenoptera | Hymenoptera |
| Serovar | 6, entomocidus | new | 6, entomocidus |

The toxin genes or gene fragments exemplified according to the subject invention can be obtained from *B. thuringiensis* (*B.t.*) isolates designated PS17, PS33F2, PS63B, PS140E2, PS211B2, and PS86Q3. Subcultures of the *E. coli* host harboring the toxin genes of the invention were deposited in the permanent collection of the Northern Research Laboratory, U.S. Department of Agriculture, Peoria, Ill., USA. The accession numbers are as follows:

| Culture | Repository No. | Deposit Date |
|---|---|---|
| *B.t.* PS140E2 | NRRL B-18812 | April 23, 1991 |
| *B.t.* PS86Q3 | NRRL B-18765 | February 6, 1991 |
| *B.t.* PS211B2 | NRRL B-18921 | November 15, 1991 |
| *B.t.* PS17 | NRRL B-18243 | July 28, 1987 |
| *B.t.* PS33F2 | NRRL B-18244 | July 28, 1987 |
| *B.t.* PS63B | NRRL B-18246 | July 28, 1987 |
| *E. coli* NM522(pMYC2316)(33F2) | NRRL B-18785 | March 15, 1991 |
| *E. coli* NM522(pMYC2321) | NRRL B-18770 | February 14, 1991 |
| *E. coli* NM522(pMYC2317) | NRRL B-18816 | April 24, 1991 |
| *E. coli* NM522(pMYC1627)(17a) | NRRL B-18651 | May 11, 1990 |
| *E. coli* NM522(pMYC1628)(17b) | NRRL B-18652 | May 11, 1990 |
| *E. coli* NM522(pMYC1642)(63B) | NRRL B-18961 | April 10, 1992 |
| *E. coli* MR618(pMYC1647)(86Q3a) | NRRL B-18970 | April 29, 1992 |
| *E. coli* NM625(pMYC1648)(86Q3c) | NRRL B-18992 | August 25, 1992 |
| *E. coli* NM522(pMYC2367)(140E2) | NRRL B-21149 | October 20, 1993 |
| *E. coli* NM522(pMYC2371)(211B2) | NRRL B-21150 | October 20, 1993 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

In addition to the hymenopteran-active *B.t.* isolates described herein, the subject invention concerns a vast array of *B.t.* δ-endotoxins having hymenopteran activity. In addition to having formicidal activity, the toxins of the subject invention will have one or more of the following characteristics:

1. An amino acid sequence according to the generic formula disclosed herein.
2. A high degree of amino acid homology with specific toxins disclosed herein.
3. A DNA sequence encoding the toxin wherein said sequence hybridizes with probes or genes disclosed herein.
4. A nucleotide sequence which can be amplified using primers disclosed herein.
5. A crystal toxin presentation as described herein.
6. Immunoreactivity to an antibody raised to a toxin disclosed herein.

Toxins and genes. The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

One aspect of the subject invention concerns the discovery of a generic chemical formula (hereinafter referred to as the Generic Formula; SEQ ID NO. 39) which can be used to identify toxins having activity against ants. This formula describes toxin proteins having molecular weights of about 130,000 daltons or more. The Generic Formula below covers those amino acids in the N-terminal region extending two amino acids past the invariant proline residue encountered at amino acid number 695 in the sequence of 86Q3a. The organization of the toxins within this class is delineated by the following generic sequence motif that is the ultimate determinant of structure and function.

Where a stretch of wild-card amino acids are encountered (X(n) or x(n) where n>2), repetition of a given amino acid should be avoided. Similarly, P, C, E, D, K, or R utilization should be minimized.

Further guidance for characterizing the formicidal toxins of the subject invention is provided in Tables 3 and 4, which demonstrate the relatedness among formicidal toxins. These tables show a numeric score for the best matching alignment between two proteins that reflects: (1) positive scores for exact matches, (2) positive or negative scores reflecting the likelihood (or not) of one amino acid substituting for another in a related protein, and (3) negative scores for the introduction of gaps. A protein sequence aligned to itself will have the highest possible score—i.e., all exact matches and no gaps. However, an unrelated protein or a randomly generated sequence will typically have a low positive score. Related sequences have scores between the random background score and the perfect match score.

The sequence comparisons were made using the local homology algorithm of Smith and Waterman ([1981] *Advances in Applied Mathematics* 2:482–489), implemented as the program "Bestfit" in the GCG Sequence Analysis Software Package Version Apr. 7, 1991. The sequences were compared with default parameter values (comparison table:

```
  1  MOXLUEBYPx BXYUBLXxxx xxxxXXXXXX XXXXXBXXxX EXXXKXXXKX
     XxxxxxXJXX XXBXXXXXXX XXLXXXXXXX XXLZBLZBxB PXXXXXXXXX 101  XXBBXXBXXX XXXXXXXXXK xxLBXXBXXX BXXBBXXXBX XXXXXXXUXX
     BXZLUXXXXX XXXOBXXXX* XXXXxxxxxx xxxxxxxxxX XX*xxxxxxx 201  xxxxxXXUZX XOXXLXXBxx xxXEXXXXXx xxxxxxxxXL PXYOXBOXXH
     LBLXJXXLxx xxxxxXKXXB XXJXxBXXXK XXLXXXLXXX XLOBXXXBXX 301  XLXXXxXXXJ xXZXXXXXXY BJXBOXX*LE BXXXXPOBEX XXYXXxxxxx
     XLXXOKXLXZ XxxxxxXXXX BXXXXXZXXX ZXXXXXXxXX XXXBXXXXXX 401  XXXXBxxxxx xxxxXXXXXX LXXXXXXXXX XXX*xxXXXX XxXXXXXXXX
     XXZXUXXXBX XXUXxxXX*X XXXXXXXXXX XXXXXXXxKX ZXXXXXXXxx 501  xxxxxxXXXZ Z*X*XXXXxx xXXPXXxxxx xxxxXXLXXL YXXXXXXXJX
     XXxXBXxBBZ XXXXXEXXXX XBXZXXXXXX XBXXXXBXxx xXXKxxxxxX 601  xxxxxxxxEX LUZXUXBXLX XXUXBXBXBX XXXXXXYXBK *KYOZXXXXX
     XXBXBEXXXx UXBXXXXXXX ZXXXXXXZxx XXXXXYXBXZ XXxxxxxxOx 701  XLXxxxxxxx xxXUXXXXBB LEKLEBBPXX
```

Numbering is for convenience and approximate location only.

| | | | |
|---|---|---|---|
| A = ala | G = gly | M = met | S = ser |
| C = cys | H = his | N = asn | T = thr |
| D = asp | I = ile | P = pro | V = val |
| E = glu | K = lys | Q = gln | W = trp |
| F = phe | L = leu | R = arg | Y = tyr |

K = K or R
E = E or D
L = L or I
B = M, L, I, V, or F
J = K, R, E, or D
O = A or T
U = N or Q
Z = G or S
X = any naturally occurring amino acid, except C.
* = any naturally occurring amino acid.
x = any naturally occurring amino acid, except C (or complete omission of any amino acids).

Swgappep.Cmp, Gap weight:3.0, Length weight:0.1) except that gap limits of 250 residues were applied to each sequence compared. The program output value compared is referred to as the Quality score.

Tables 3 and 4 show the pairwise alignments between the indicated amino acids of the ant-active proteins and representatives of dipteran (CryIV; ISRH3 of Sen, K. et al. [1988] *Agric. Biol. Chem.* 52:873–878), lepidopteran and dipteran (CryIIA; CryB1 of Widner and Whiteley [1989] *J. Bacteriol.* 171:965–974), and lepidopteran (CryIA(c); Adang et al. [1981] *Gene* 36:289–300) proteins.

Table 2 shows which amino acids were compared from the proteins of interest.

The N-terminal portions of the molecules consisting of about 600–700 amino acids were compared. As can be seen from Table 2, the amino acids compared started with amino acid 1 at the N-terminus and continued about 600–700 amino acids toward the C-terminus. The exact length of the sequence to be compared is readily determined using the alignment program referred to above which takes into account regions of homology including those which exist in the portion of the toxins 600–700 amino acids from the N-terminus.

TABLE 2

| Protein | Amino acids compared |
| --- | --- |
| 86Q3c | 1–672 |
| 86Q3a | 1–697 |
| 63B | 1–692 |
| 33F2 | 1–618 |
| 17a | 1–677 |
| 17b | 1–678 |
| CryIV | 1–633 |
| CryIIA | 1–633 |
| CryIIIA | 1–644 |

Table 3 shows the scores prior to adjustment for random sequence scores.

TABLE 3

|  | 86Q3c | 86Q3a | 63B | 33F2 | 17b | 17a | CryIVA | CryIIA | CryIA (c) | CryIIIA |
| --- | --- | --- | --- | --- | --- | --- | --- | --- | --- | --- |
| 86Q3c | 1008 | 357.0 | 339.1 | 321.7 | 975.5 | 974.6 | 233.5 | 238.2 | 232.4 | 248.4 |
| 86Q3a |  | 1045.5 | 388.8 | 310.5 | 341.5 | 339.7 | 236.3 | 235.6 | 238.1 | 256.6 |
| 63B |  |  | 1038 | 273.8 | 339.4 | 338 | 235.2 | 227.8 | 232.3 | 243.6 |
| 33F2 |  |  |  | 927 | 323 | 321.5 | 250.9 | 232.5 | 250.9 | 270.4 |
| 17b |  |  |  |  | 1017 | 1007 | 238.3 | 240.4 | 236 | 248.4 |
| 17a |  |  |  |  |  | 1015.5 | 239.6 | 240 | 236.6 | 248.9 |
| CryIVA |  |  |  |  |  |  | 949.5 | 244.8 | 325.1 | 326.2 |
| CryIIA |  |  |  |  |  |  |  | 949.5 | 243.6 | 241.3 |
| CryIA (c) |  |  |  |  |  |  |  |  | 913.5 | 366.6 |
| CryIIIA |  |  |  |  |  |  |  |  |  | 966 |

Note that ant-active protein 86Q3a is more closely related to 63B, 17a, 17b, and 33F2 than it is to the CryIVA, CryIIA, and CryIA(c) toxins.

Table 4 shows the same analysis after subtraction of the average score of 50 alignments of random shuffles of the column sequences with the row sequences.

TABLE 4

|  | 86Q3c | 86Q3a | 63B | 33F2 | 17b | 17a | CryIVA | CryIIA | CryIA (c) | CryIIIA |
| --- | --- | --- | --- | --- | --- | --- | --- | --- | --- | --- |
| 86Q3c | 803.5 | 155.8 | 133.5 | 128.7 | 769.0 | 767.6 | 39.2 | 42.6 | 43.3 | 53.8 |
| 86Q3a |  | 841 | 183.5 | 118.2 | 136.4 | 134.6 | 40.8 | 39.8 | 49.8 | 60.1 |
| 63B |  |  | 830.8 | 81.2 | 132.9 | 129.2 | 39.3 | 33.2 | 43.3 | 48.7 |
| 33F2 |  |  |  | 739.3 | 129.7 | 128 | 65.4 | 50.1 | 70.9 | 84.2 |
| 17b |  |  |  |  | 810.9 | 797.7 | 42.5 | 44.3 | 46.7 | 55.5 |
| 17a |  |  |  |  |  | 808.3 | 42.8 | 43.7 | 44.5 | 53 |
| CryIVA |  |  |  |  |  |  | 760.6 | 54 | 141.1 | 141.1 |
| CryIIA |  |  |  |  |  |  |  | 755.4 | 54.7 | 51.2 |
| CryIA (c) |  |  |  |  |  |  |  |  | 728.8 | 182 |
| CryIIIA |  |  |  |  |  |  |  |  |  | 777.9 |

Note that in Table 4 the same relationship holds as in Table 3, i.e., 86Q3a's highest score, aside from itself, is with 63B.

This degree of relatedness provides the basis for using common or similar sequence elements from the previously-described known genes to obtain related, but non-identical genes from an ant-active isolate.

Thus, certain toxins according to the subject invention can be defined as those which have formicidal activity and have an alignment value (according to the procedures of Table 4) greater than 100 with 86Q3a. As used herein, the term "alignment value" refers to the scores obtained using the methods described above which were used to create the scores reported in Table 4.

The toxins of the subject invention can also be characterized in terms of the shape and location of toxin inclusions.

Inclusion type

PS86Q3—Long amorphic inclusion and a small inclusion, both of which remain with the spore after lysis. See FIG. 3.

Figure 4:

PS140E2—An elliptical coated inclusion situated outside the exosporium, and a long inclusion inside the exosporium. See FIG. 4.

Figure 5:
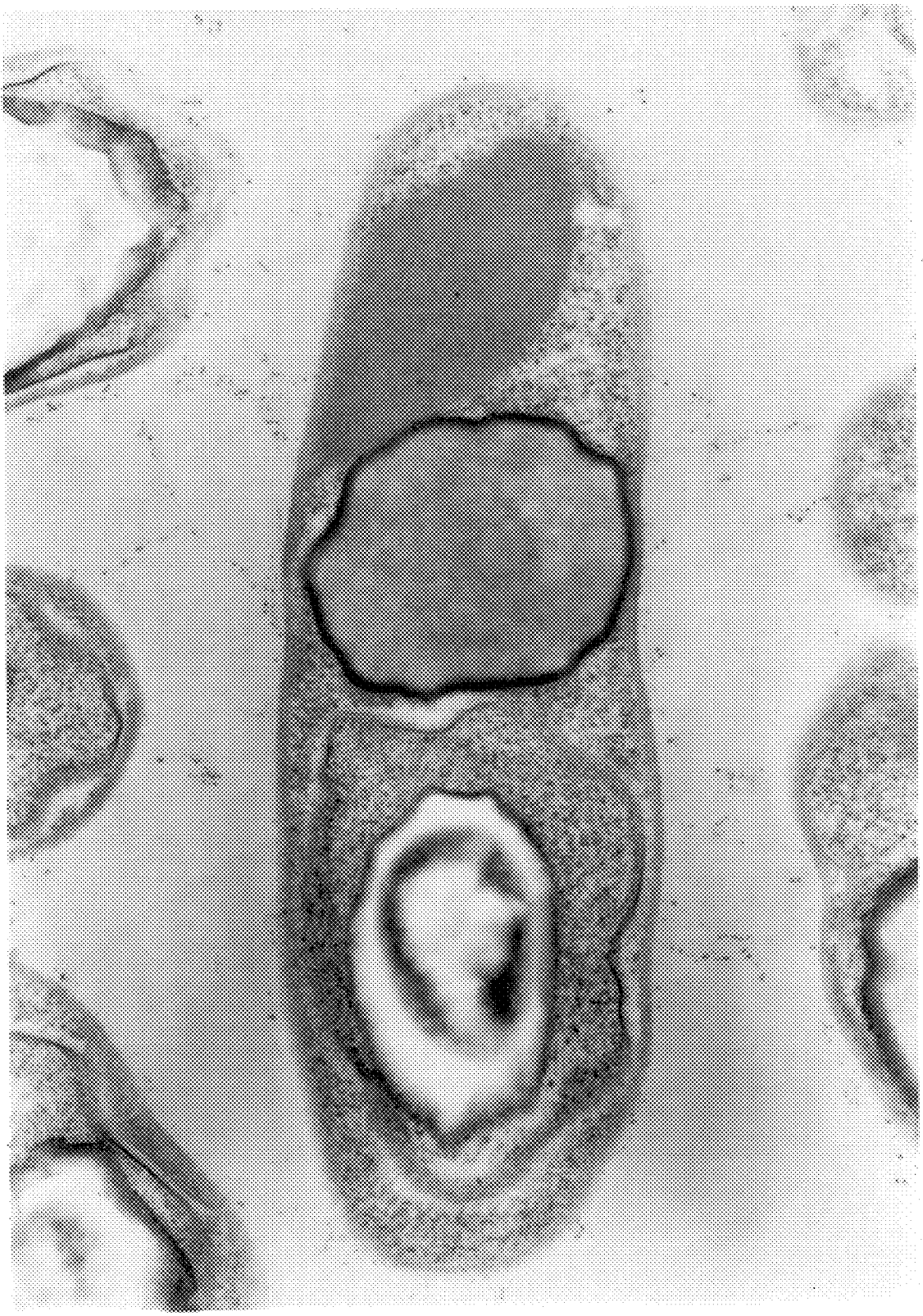

PS211B2—Large round amorphic inclusion with coat, and an elliptical inclusion. See FIG. 5.

Formicidal toxins according to the Generic Formula (SEQ ID NO. 39) of the subject invention are specifically exemplified herein by the toxin encoded by the gene designated 86Q3a. Since this toxin is merely exemplary of the toxins represented by the Generic Formula (SEQ ID NO. 39) presented herein, it should be readily apparent that the subject invention comprises all toxins conforming to the Generic Formula (SEQ ID NO. 39) and further comprises equivalents of those toxins (and nucleotide sequences coding for equivalent toxins) having the same or similar biological activity to ants. Equivalent toxins will have amino acid homology with the original toxin. This amino acid homology will typically be greater than 75%, preferably be greater than 90%, and most preferably be greater than 95%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 5 provides a listing of examples of amino acids belonging to each class.

TABLE 5

| Class of Amino Acid | Eamples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin. The information presented in the Generic Formula of the subject invention provides clear guidance to the person skilled in this art in making various amino acid substitutions.

It should be apparent to a person skilled in this art that genes encoding active toxins can be identified and obtained through several means. The specific genes exemplified herein may be obtained from the isolates deposited at a culture depository as described above.

These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from *B.t.* isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other *B.t.* toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism. Therefore, included within the scope of the subject invention are toxins which immunoreact with (i.e., bind with) antibodies to the toxins exemplified herein.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Detection of the probe provides a means for determining in a known manner whether hybridization has occurred. Such a probe analysis provides a rapid method for identifying toxin-encoding genes of the subject invention.

The nucleotide segments which are used as probes according to the invention can be synthesized by use of DNA synthesizers using standard procedures. In the use of labeled nucleotide segments as probes, the particular probe is labeled with any suitable label known to those skilled in the art, including radioactive and non-radioactive labels. Typical radioactive labels include $^{32}P$, $125I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Preferably, hybridization is conducted under stringent conditions by techniques well known in the art, as described, for example, in Keller, G. H., M. M. Manak (1989) *DNA Probes*, Stockton Press, New York, N.Y., pp. 169–170. For example, as stated therein, hybridization can occur at 42° C. in a hybridization buffer containing 50% formamide, 5× SSC, 1× Denhardt's solution, 31 mM $KH_2PO_4$, 0.25% SDS, 30 μg/ml sheared, denatured salmon sperm DNA, and 5% dextran sulfate and as stated therein, high stringency washes can be conducted with 2× SSC (Standard Sodium Citrate)/0.1% SDS (Sodium Dodecyl Sulfate) for 15 minutes at room temperature. Two washes are typically performed. The 2× SSC/0.1% SDS can be prepared by adding 50 ml of 20× SSC and 5 ml of 10% SDS to 445 ml of water. 20× SSC can be prepared by combining NaCl (175.3 g/0.150 M), sodium citrate (88.2 g/0.015 M), and water to 1 liter, followed by adjusting pH to 7.0 with 10 N NaOH. 10% SDS can be prepared by dissolving 10 g of SDS in 50 ml of autoclaved water, diluting to 100 ml, and aliquotting. Alternatively, high stringency washes can be conducted with 0.1× SSC/0.1% SDS for 30 minutes each at 55° C. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) synthesizing chemically or otherwise an artificial sequence which is a mutation, insertion or deletion of the known sequence;

(2) using a probe of the present invention to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed test sequences can be readily prepared by methods which are well known to those skilled in the art. These variants can be used in the same manner as the instant probes so long as the variants have substantial sequence homology with the probes. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

Specific nucleotide probes useful, according to the subject invention, in the rapid identification of ant-active genes are (i) DNA coding for a peptide sequence whose single letter amino acid designation is "REWINGAN" (SEQ ID NO. 11) or variations thereof which embody point mutations according to the following: position 1, R or K; position 3, W or Y; position 4, I or L; position 7, A or N; position 8, N or Q; a specific example of such a probe is "AGA(A or G)T(G or A)(G or T)(A or T)T(A or T)AATGG(A or T)GC(G or T)(A or C)A" (SEQ ID NO. 12); another example of such a probe is "GA(A or G)TGG(A or T)TAAATGGT(A or G)(A or C)(G or C)AA" (SEQ ID NO. 13);

(ii) DNA coding for a peptide sequence whose single letter amino acid designation is "PTFDPDLY" (SEQ ID NO. 14) or variations thereof which embody point mutations according to the following: position 3, F or L; position 4, D or Y; position 5, P or T; position 6, D or H; position 7, L or H or D or N; a specific example of such a probe is "CC(A or T)AC(C or T)TTT(T or G)ATCCAGAT(C or G)(T or A)(T or C)TAT" (SEQ ID NO. 15); another example of such a probe is "CC(T or A)AC(T or A)TT(T or C)GAT(C or A)CA(G or C)AT(C or A)(T or A)TTAT" (SEQ ID NO. 16);

(iii) additional useful probes for detecting ant-active B.t. genes include "GCAATTTTAA ATGAATTATA TCC" (SEQ ID NO. 23), "CAAYTACAAG CWCAACC" (SEQ ID NO. 24), "AATGAAGTWT ATCCWGTWAA T" (SEQ ID NO. 27), "GCAAGCGGCC GCTTATGGAA TAAATTCAAT TYKRTCWA" (SEQ ID NO. 28), "AGACTGGATC CATG-GCWACW ATWAATGAAT TATAYCC" (SEQ ID NO. 29), "TAACGTGTAT WCGSTTTTAA TTTWGAYTC" (SEQ ID NO. 31), "TGGAATAAAT TCAATTYKRT CWA" (SEQ ID NO. 33), "AGGAACAAAY TCAAKWCGRT CTA" (SEQ ID NO. 34), and "TCTCCATCTT CTGARGWAAT" (SEQ ID NO. 37).

The potential variations in the probes listed is due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, the amino acid sequences of the B.t. toxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser, E. T., Kezdy, F. J. [1984] Science 223:249–255). Thus, the subject invention includes mutants of the amino acid sequence depicted herein which do not alter the protein secondary structure, or if the structure is altered, the biological activity is substantially retained. Further, the invention also includes mutants of organisms hosting all or part of a toxin encoding a gene of the invention. Such microbial mutants can be made by techniques well known to persons skilled in the art. For example, UV irradiation can be used to prepare mutants of host organisms. Likewise, such mutants may include asporogenous host cells which also can be prepared by procedures well known in the art.

Recombinant hosts. The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a *B.t.* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. As mentioned above, *B.t.* or recombinant cells expressing a *B.t.* toxin can be treated to prolong the toxin activity and stabilize the cell for application to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., *Animal Tissue Techniques,* W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bioavailability or bioactivity of the toxin.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells of the invention can be cultured using standard art media and fermentation techniques. Upon completion of the fermentation cycle the bacteria can be harvested by first separating the *B.t.* spores and crystals from the fermentation broth by means well known in the art. The recovered *B.t.* spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores and crystals of the *B.t.* isolates, or recombinant microbes comprising the genes obtainable from the *B.t.* isolates disclosed herein, can be applied to the soil. Formulated product can also be applied as a seed-coating or root treatment or total plant treatment at later stages of the crop cycle. Plant and soil treatments of *B.t.* cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest, e.g., soil, foliage, or water, by spraying, dusting, sprinkling, or the like.

Mutants. Mutants of the isolates of the invention can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is placed in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. Isolates of the Invention

A subculture of a B.t. isolate can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salts Solution | 5.0 ml/l |
| $CaCl_2$ Solution | 5.0 ml/l |
| Salts Solution (100 ml) | |
| $MgSO_4 \cdot 7H_2O$ | 2.46 g |
| $MnSO_4 \cdot H_2O$ | 0.04 g |
| $ZnSO_4 \cdot 7H_2O$ | 0.28 g |
| $FeSO_4 \cdot 7H_2O$ | 0.40 g |
| $CaCl_2$ Solution (100 ml) | |
| $CaCl_2 \cdot 2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

EXAMPLE 2

Purification of Protein and Amino Acid Sequencing

The B.t. isolates PS86Q3, PS17, PS63B, PS33F2, PS140E2, and PS211B2 were cultured as described in Example 1. The B.t. cells were harvested by standard sedimentation centrifugation. Parasporal inclusion bodies of some isolates were partially purified by sodium bromide (26–40%) isopycnic gradient centrifugation (Pfannenstiel, M. A., E. J. Ross, V. C. Kramer, K. W. Nickerson [1984] FEMS Microbiol. Lett. 21:39). Preparations containing proteins toxic to ants were bound to PVDF membranes (Millipore, Bedford, Mass.) by western blotting techniques (Towbin, H., T. Staehlelin, K. Gordon [1979] Proc. Natl. Acad. Sci. USA 76:4350) and the N-terminal amino acid sequences were determined by the standard Edman reaction with an automated gas-phase sequenator (Hunkapiller, M. W., R. M. Hewick, W. L. Dreyer, and L. E. Hood [1983] Meth. Enzymol. 91:399). The sequences obtained were:

| | | |
|---|---|---|
| 17a: | A I L N E L Y P S V P Y N V | (SEQ ID NO. 17) |
| 17b: | A I L N E L Y P S V P Y N V | (SEQ ID NO. 18) |
| 86Q3a: | M A T I N E L Y P N V P Y N V L | (SEQ ID NO. 19) |
| 63B: | Q L Q A Q P L I P Y N V L A | (SEQ ID NO. 20) |
| 33F2: | A T L N E V Y P V N | (SEQ ID NO. 21) |
| 140E2: | A N T T Q S F H F S N I L D Y K | (SEQ ID NO. 44) |
| 211B2: | A A S D Y I D P I F | (SEQ ID NO. 47) |

Internal amino acid sequence data were derived for 63B and PS211B2. The toxin protein was partially digested with Staphylococcus aureus V8 protease (Sigma Chem. Co., St. Louis, Mo.) essentially as described (Cleveland, D. W., S. G. Fischer, M. W. Kirschner, U.K. Laemmli [1977] J. Biol. Chem. 252:1102). The digested material was blotted onto PVDF membrane and a ca. 28 kDa limit peptide was selected for N-terminal sequencing as described above. The sequence obtained was:

| | | |
|---|---|---|
| 63B(2) | V Q R I L D E K L S F Q L I K | (SEQ ID NO. 22) |

An internal amino acid sequence was also determined for 211B2 by in situ enzymatic cleavage of the electroblotted protein (Abersold, R. H., J. Leavitt, R. A. Saavedra, L. E. Hood, S. B. Kent [1987] Proc. Natl. Acad. Sci. USA 84:6970). From this sequence data oligonucleotide probes were synthesized on an Applied Biosystems, Inc. DNA synthesis machine. The sequence obtained was:

| | | |
|---|---|---|
| 211B2: | G I G F E L D T Y A N A P E D E V | (SEQ ID NO. 46) |

From these sequence data oligonucleotide probes were designed by utilizing a codon frequency table assembled from available sequence data of other B.t. toxin genes. The probes were synthesized on an Applied Biosystems, Inc. DNA synthesis machine.

Protein purification and subsequent amino acid analysis of the N-terminal peptides listed above has led to the deduction of several oligonucleotide probes for the isolation of toxin genes from formicidal B.t. isolates. RFLP analysis of restricted total cellular DNA using radiolabeled oligonucleotide probes has elucidated different genes or gene fragments.

EXAMPLE 3

Cloning of Toxin Genes from Bacillus thuringiensis Strain PS17 and Transformation into Escherichia coli Total cellular DNA was prepared by growing the cells B.t. PS17 to a low optical density ($OD_{600}$=1.0) and recovering the cells by centrifugation. The cells were protoplasted in TES buffer (30 mM Tris-Cl, 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium chloride-ethidium bromide gradient.

Total cellular DNA from PS17 was digested with EcoRI and separated by electrophoresis on a 0.8% (w/v) Agarose-TAE (50 mM Tris-HCl, 20 mM NaOAc, 2.5 mM EDTA, pH=8.0) buffered gel. A Southern blot of the gel was hybridized with a [$^{32}$P]-radiolabeled oligonucleotide probe derived from the N-terminal amino acid sequence of purified 130 kDa protein from PS17. The sequence of the oligonucleotide synthesized is (GCAATTTTAAATGAATTATATCC) (SEQ ID NO. 23). Results showed that the hybridizing EcoRI fragments of PS17 are 5.0 kb, 4.5 kb, 2.7 kb and 1.8 kb in size, presumptively identifying at least four new ant-active toxin genes, 17d, 17b, 17a and 17e, respectively.

A library was constructed from PS17 total cellular DNA partially digested with Sau3A and size fractionated by electrophoresis. The 9 to 23 kb region of the gel was excised and the DNA was electroeluted and then concentrated using an Elutip™ ion exchange column (Schleicher and Schuel, Keene N.H.). The isolated Sau3A fragments were ligated into LambdaGEM-11™ (PROMEGA). The packaged phage were plated on KW251 E. coli cells (PROMEGA) at a high titer and screened using the above radiolabeled synthetic oligonucleotide as a nucleic acid hybridization probe. Hybridizing plaques were purified and rescreened at a lower plaque density. Single isolated purified plaques that hybridized with the probe were used to infect KW251 E. coli cells in liquid culture for preparation of phage for DNA isolation. DNA was isolated by standard procedures.

Recovered recombinant phage DNA was digested with EcoRI and separated by electrophoresis on a 0.8% agarose-TAE gel. The gel was Southern blotted and hybridized with the oligonucleotide probe to characterize the toxin genes isolated from the lambda library. Two patterns were present, clones containing the 4.5 kb (17b) or the 2.7 kb (17a) EcoRI fragments. Preparative amounts of phage DNA were digested with SalI (to release the inserted DNA from lambda arms) and separated by electrophoresis on a 0.6% agarose-TAE gel. The large fragments, electroeluted and concentrated as described above, were ligated to SalI-digested and dephosphorylated pBClac, an E. coli/B.t. shuttle vector comprised of replication origins from pBC16 and pUC19. The ligation mix was introduced by transformation into NM522 competent E. coli cells and plated on LB agar containing ampicillin, isopropyl-(Beta)-D-thiogalactoside (IPTG) and 5-Bromo-4-Chloro-3-indolyl-(Beta)-D-galactoside (XGAL). White colonies, with putative insertions in the (Beta)-galactosidase gene of pBClac, were subjected to standard rapid plasmid purification procedures to isolate the desired plasmids. The selected plasmid containing the 2.7 kb EcoRI fragment was named pMYC1627 and the plasmid containing the 4.5 kb EcoRI fragment was called pMYC1628.

The toxin genes were sequenced by the standard Sanger dideoxy chain termination method using the synthetic oligonucleotide probe, disclosed above, and by "walking" with primers made to the sequence of the new toxin genes.

The PS17 toxin genes were subcloned into the shuttle vector pHT3101 (Lereclus, D. et al. [1989] *FEMS Microbiol. Lett.* 60:211–218) using standard methods for expression in B.t. Briefly, SalI fragments containing the 17a and 17b toxin genes were isolated from pMYC1629 and pMYC1627, respectively, by preparative agarose gel electrophoresis, electroelution, and concentrated, as described above. These concentrated fragments were ligated into SalI-cleaved and dephosphorylated pHT3101. The ligation mixtures were used separately to transform frozen, competent E. coli NM522. Plasmids from each respective recombinant E. coli strain were prepared by alkaline lysis and analyzed by agarose gel electrophoresis. The resulting subclones, pMYC2311 and pMYC2309, harbored the 17a and 17b toxin genes, respectively. These plasmids were transformed into the acrystalliferous B.t. strain, HD-1 cryB (Aronson, A., Purdue University, West Lafayette, Ind.), by standard electroporation techniques (Instruction Manual, Biorad, Richmond, Calif.).

Recombinant B.t. strains HD-1 cryB [pMYC2311] and [pMYC2309] were grown to sporulation and the proteins purified by NaBr gradient centrifugation as described above for the wild-type B.t. proteins.

EXAMPLE 4

Molecular Cloning of a Gene Encoding a Toxin from Bacillus thuringiensis Strain PS63B Example 2 shows the aminoterminal and internal polypeptide sequences of the 63B toxin protein as determined by standard Edman protein sequencing. From these sequences, two oligonucleotide primers were designed using a codon frequency table assembled from B.t. genes encoding δ-endotoxins. The sequence of the forward primer (63B-A) was complementary to the predicted DNA sequence at the 5' end of the gene:

63B-A - 5' CAA T/CTA CAA GCA/T CAA
CC 3'                                (SEQ ID NO. 24)

The sequence of the reverse primer (63B-INT) was complementary to the inverse of the internal predicted DNA sequence:

63B-INT - 5' TTC ATC TAA AAT TCT TTG
A/TAC 3'                             (SEQ ID NO. 25)

These primers were used in standard polymerase chain reactions (Cetus Corporation) to amplify an approximately 460 bp fragment of the 63B toxin gene for use as a DNA cloning probe. Standard Southern blots of total cellular DNA from 63B were hybridized with the radiolabeled PCR probe. Hybridizing bands included an approximately 4.4 kbp XbaI fragment, an approximately 2.0 kbp HindIII fragment, and an approximately 6.4 kbp SpeI fragment.

Total cellular DNA was prepared from *Bacillus thuringiensis* (B.t.) cells grown to an optical density of 1.0 at 600 nm. The cells were recovered by centrifugation and protoplasts were prepared in lysis mix (300 mM sucrose, 25 mM Tris-HCl, 25 mM EDTA, pH=8.0) and lysozyme at a concentration of 20 mg/ml. The protoplasts were ruptured by addition of ten volumes of 0.1 M NaCl, 0.1 M Tris-HCl pH 8.0, and 0.1% SDS. The cellular material was quickly frozen at −70° C. and thawed to 37° C. twice. The supernatant was extracted twice with phenol/chloroform (1:1). The nucleic acids were precipitated with ethanol. To remove as much RNA as possible from the DNA preparation, RNase at final concentration of 200 μg/ml was added. After incubation at 37° C. for 1 hour, the solution was extracted once with phenol/chloroform and precipitated with ethanol.

A gene library was constructed from 63B total cellular DNA partially digested with NdeII and size fractioned by gel electrophoresis. The 9–23 kb region of the gel was excised and the DNA was electroeluted and then concentrated using an Elutip-d ion exchange column (Schleicher and Schuel, Keene, N.H.). The isolated NdeII fragments were ligated into BamHI-digested LambdaGEM-11 (PROMEGA). The packaged phage were plated on *E. coli* KW251 cells (PROMEGA) at a high titer and screened using the radio-labeled approximately 430 bp fragment probe amplified with the 63B-A and 63B internal primers (SEQ ID NOS. 27 and 28, respectively) by polymerase chain reaction. Hybridizing plaques were purified and rescreened at a lower plaque density. Single isolated, purified plaques that hybridized with the probe were used to infect KW251 cells in liquid culture for preparation of phage for DNA isolation. DNA was isolated by standard procedures (Maniatis, T., E. F. Fritsch, J. Sambrook [1982] *Molecular Cloning: A Laboratory Manual,* Cold Spring Harbor Laboratory, New York). Preparative amounts of DNA were digested with SalI (to release the inserted DNA from lambda sequences) and separated by electrophoresis on a 0.6% agarose-TAE gel. The large fragments were purified by ion exchange chromatography as above and ligated to SalI-digested, dephosphorylated pHTBlueII (an *E. coli/B.t.* shuttle vector comprised of pBlueScript S/K [Stratagene, San Diego, Calif.] and the replication origin from a resident *B.t.* plasmid [Lereclus, D. et al. (1989) *FEMS Microbiol. Lett.* 60:211–218]). The ligation mix was introduced by transformation into competent *E. coli* NM522 cells (ATCC 47000) and plated on LB agar containing ampicillin (100 μg/ml), IPTG (2%), and XGAL (2%). White colonies, with putative restriction fragment insertions in the (Beta)-galactosidase gene of pHTBlueII, were subjected to standard rapid plasmid purification procedures (Maniatis et al., supra). Plasmids ere analyzed by SalI digestion and agarose gel electrophoresis. The desired plasmid construct, pMYC1641, contains an approximately 14 kb SalI insert.

For subcloning, preparative amounts of DNA were digested with XbaI and electrophoresed on an agarose gel. The approximately 4.4 kbp band containing the toxin gene was excised from the gel, electroeluted from the gel slice, and purified by ion exchange chromatography as above. This fragment was ligated into XbaI cut pHTBlueII and the resultant plasmid was designated pMYC1642.

EXAMPLE 5

Cloning of a Toxin Gene From *B.t.* PS33F2 and Transformation into *Escherichia coli*

Total cellular DNA was prepared from *B.t.* PS33F2 cells grown to an optical density, at 600 nm, of 1.0. Cells were pelleted by centrifugation and resuspended in protoplast buffer (20 mg/ml lysozyme in 0.3 M sucrose, 25 mM Tris-Cl [pH 8.0], 25 mM EDTA). After incubation at 37° C. for 1 hour, protoplasts were lysed by the addition of nine volumes of a solution of 0.1 M NaCl, 0.1% SDS, 0.1 M Tris-Cl followed by two cycles of freezing and thawing. The cleared lysate was extracted twice with phenol:chloroform (1:1). Nucleic acids were precipitated with two volumes of ethanol and pelleted by centrifugation. The pellet was resuspended in 10 mM Tris-Cl, 1 mM EDTA (TE) and RNase was added to a final concentration of 50 μg/ml. After incubation at 37° C. for 1 hour, the solution was extracted once each with phenol:chloroform (1:1) and TE-saturated chloroform. DNA was precipitated from the aqueous phase by the addition of one-tenth volume of 3 M NaOAc and two volumes of ethanol. DNA was pelleted by centrifugation, washed with 70% ethanol, dried, and resuspended in TE.

Plasmid DNA was extracted from protoplasts prepared as described above. Protoplasts were lysed by the addition of nine volumes of a solution of 10 mM Tris-Cl, 1 mM EDTA, 0.085 N NaOH, 0.1% SDS, pH=8.0. SDS was added to 1% final concentration to complete lysis. One-half volume of 3 M KOAc was then added and the cellular material was precipitated overnight at 4° C. After centrifugation, the DNA was precipitated with ethanol and plasmids were purified by isopycnic centrifugation on cesium chloride-ethidium bromide gradients.

Restriction Fragment Length Polymorphism (RFLP) analyses were performed by standard hybridization of Southern blots of PS33F2 plasmid and total cellular DNA with $^{32}P$-labelled oligonucleotide probes designed to the N-terminal amino acid sequence disclosed in Example 2.

Probe 33F2A: 5' GCA/T ACA/TTTA AAT GAA GTA/TTAT 3' (SEQ ID NO. 26)

Probe 33F2B: 5' AAT GAA GTA/T TAT CCA/T GTA/TAAT 3' (SEQ ID NO. 27)

Hybridizing bands included an approximately 5.85 kbp EcoRI fragment. Probe 33F2A and a reverse PCR primer were used to amplify a DNA fragment of approximately 1.8 kbp for use as a hybridization probe for cloning the 33F2 toxin gene. The sequence of the reverse primer was:

5' GCAAGCGGCCGCTTATGGAATAAATTCAATT C/T T/G A/G TC T/A A 3' (SEQ ID NO. 28).

A gene library was constructed from 33F2 plasmid DNA digested with EcoRI. Restriction digests were fractionated by agarose gel electrophoresis. DNA fragments 4.3–6.6 kbp were excised from the gel, electroeluted from the gel slice, and recovered by ethanol precipitation after purification on an Elutip-D ion exchange column (Schleicher and Schuel, Keene N.H.). The EcoRI inserts were ligated into EcoRI-digested pHTBlueII (an *E. coli/B. thuringiensis* shuttle vector comprised of pBluescript S/K [Stratagene] and the replication origin from a resident *B.t.* plasmid (Lereclus et al., supra). The ligation mixture was transformed into frozen, competent NM522 cells (ATCC 47000). Transformants were plated on LB agar containing ampicillin, isopropyl-(Beta)-D-thiogalactoside(IPTG), and 5-bromo-4-chloro-3-indolyl-(Beta)-D-galactoside(XGAL). Colonies were screened by hybridization with the radiolabeled PCR amplified probe described above. Plasmids were purified from putative toxin gene clones by alkaline lysis and analyzed by agarose gel electrophoresis of restriction digests. The desired plasmid construct, pMYC2316, contains an approximately 5.85 kbp Eco4RI insert; the toxin gene residing on this DNA fragment (33F2a) is novel compared to the DNA sequences of other toxin genes encoding formicidal proteins.

Plasmid pMYC2316 was introduced into the acrystalliferous ($Cry^-$) *B.t.* host, HD-1 CryB (A. Aronson, Purdue University, West Lafayette, Ind.) by electroporation. Expression of an approximately 120–140 kDa crystal protein was verified by SDS-PAGE analysis. Crystals were purified on NaBr gradients (Pfannenstiel et al., supra) for determination of toxicity of the cloned gene product to Pratylenchus spp.

EXAMPLE 6

Cloning of a Novel Toxin Gene from B.t. Isolate PS86Q3

Total cellular DNA was prepared from *Bacillus thuringiensis* (*B.t.*) cells as described in Example 5.

Total cellular DNA from isolate PS86Q3 was used as template for polymerase chain reaction (PCR) analysis according to protocols furnished by Perkin Elmer Cetus. An oligonucleotide derived from the N-terminal amino acid sequence of the toxin protein was used as a 5' primer. The sequence of this oligonucleotide is:

5'-AGACTGGATCCATGGC(A or T)AC(A or T)AT(A or T)AAT-
GAATTATA (T or C)CC-3'  (SEQ ID NO. 29).

An oligonucleotide coding for the amino acid sequence "ESKLKPNTRY" (SEQ ID NO. 30) can be used as the reverse 3' primer. The sequence of this oligonucleotide can be:

"5'-TAACGTGTAT(A or T)CG(C or G)TTTTAATTT(T or
A)GA(C or T)TC-3'"  (SEQ ID NO. 31).

The reverse "YIDKIEFIP" (SEQ ID NO. 32) oligonucleotide was also used as a reverse 3' primer in conjunction with the above mentioned 5' primer. The sequence of the reverse primer can be:

"5'-TGGAATAAATTCAATT(Cor T)(T or G)(A or G)TC(T or
A)A-3'"  (SEQ ID NO. 33).

Amplification with the 5' primer and SEQ ID NO. 31 generates an approximately2.3 kbp DNA fragment and an approximately 4.3 kbp DNA fragment. Amplification with the 5' primer and SEQ ID NO. 33 generates an approximate 1.8 kbp DNA fragment and an approximately 3.7 kbp DNA fragment. The approximately 2.3 kbp fragment was radiolabeled with $^{32}$P and used as a hybridization probe to generate restriction fragment polymorphism (RFLP) patterns and to screen recombinant phage libraries.

A Southern blot of total cellular DNA digested with EcoRV was probed with the radiolabeled2.3 kbp probe described above. The resultant RFLP includes 9.5 kbp, 6.4 kbp, and 4.5 kbp hybridizing fragments.

A gene library was constructed from PS86Q3 total cellular DNA partially digested with NdeII and size fractioned by gel electrophoresis. The 9–23 kb region of the gel was excised and the DNA was electroeluted and then concentrated using an Elutip-d ion exchange column (Schleicher and Schuel, Keene, N.H.). The isolated NdeII fragments were ligated into BamHI-digested LambdaGEM-11 (PROMEGA). The packaged phage were plated on *E. coli* KW251 cells (PROMEGA) at a high titer and screened using the radiolabeled probe described above. Hybridizing plaques were purified and rescreened at a lower plaque density. Single isolated, purified plaques that hybridized with the probe were used to infect KW251 cells in liquid culture for preparation of phage for DNA isolation. DNA was isolated by standard procedures (Maniatis et al., supra).

Preparative amounts of DNA were digested with SalI (to release the inserted DNA from lambda sequences) and separated by electrophoresis on a 0.6% agarose-TAE gel. The large fragments were purified by ion exchange chromatography as above and ligated to SalI-digested, dephosphorylated pHTBlueII (an *E. coli/B.t.* shuttle vector comprised of pBluescript S/K [Stratagene, San Diego, Calif.]) and the replication origin from a resident *B.t.* plasmid (Lereclus et al. [1989], supra). The ligation mix was introduced by transformation into competent *E. coli* NM522 cells (ATCC 47000) and plated on LB agar containing ampicillin, IPTG, and XGAL. White colonies, with putative restriction fragment insertions in the (Beta)-galactosidase gene of pHTBlueII, were subjected to standard rapid plasmid purification procedures (Maniatis et al., supra). Plasmid DNA was analyzed by SalI digestion and agarose gel electrophoresis. The desired plasmid construct, pMYC1647, contains an approximately 12 kb SalI insert.

Plasmid pMYC1647 was introduced by electroporation into an acrystalliferous (Cry$^-$) *B.t.*, HD-1 CryB (A.I. Aronson, Purdue University) host to yield MR515, a recombinant *B.t.* clone of 86Q3a. Expression of an approximately 155 kDa protein was verified by SDS-PAGE. Spores and crystals were removed from broth cultures and were used for determination of toxicity to pharaoh ants.

EXAMPLE 7

Cloning of a Second Novel Toxin Gene from *B.t.* Isolate PS86Q3

Total cellular DNA was prepared from *Bacillus thuringiensis* (*B.t.*) cells grown to an optical density of 1.0 at 600 nm. The cells were recovered by centrifugation and protoplasts were prepared in lysis mix (300 mM sucrose, 25 mM Tris-HCl, 25 mM EDTA, pH=8.0) and lysozyme at a concentration of 20 mg/ml. The protoplasts were ruptured by addition of ten volumes of 1% SDS. The cellular material was quickly frozen at −70° C. and thawed to 37° C. twice. The supernate was extracted twice with phenol/chloroform (1:1). The nucleic acids were precipitated with ethanol. In order to remove as much RNA as possible from the DNA preparation, RNase at final concentration of 200 μg/ml was added and followed by phenol/chloroform extraction and ethanol precipitation.

Total cellular DNA from isolate PS86Q3 was used as template for polymerase chain reaction (PCR) analysis according to protocols furnished by Perkin Elmer Cetus. An oligonucleotide derived from the N-terminal amino acid sequence of the 135 kDa and 155 kDa proteins was used as a 5' primer. The sequence of this oligo is: 5'-AGACTGGATCC ATG GC(A or T) AC(A or T) AT(A or T) AAT GAA TTA TA(T or C) CC-3' (SEQ ID NO. 40). The "protoxin T" oligonucleotide (SEQ ID NO. 41) was used as the reverse 3' primer. The sequence of this oligo is: 5'-GACTGCGGCC GCGTCGAC TTA ACG TGT AT(A or T) CG(C or G) TTT TAA TTT (T or A)GA (C or T)TC-3'.

Amplification with these two primers generated an approxximately 2.3 kbp DNA fragment. This fragment was then used as a hybridization probe. A Southern blot of 86Q3 total DNA digested with EcoRV and fractionated by electrophoresis on 0.8 (w/v) agarose-TAE buffered gel showed hybridizing fragments of approximately 6.4 kb and approximately 4.8kb.

A library was constructed from PS86Q3 total cellular DNA as described in Example 6. The procedure varied from that used in Example 6 in that restriction enzyme XhoI was used to digest the DNA instead of SalI. The desired plasmid construct, pMYC1648, includes an approximately 14 kbp XhoI insert which contains the 86Q3c gene. Sequence analysis of the toxin gene revealed that it encodes a protein of approximately 134.5 kDa, deduced from the DNA sequence. The nucleotide and deduced amino acid sequences are shown in SEQ ID NOS. 42 and 43, respectively.

Plasmid pMYC1648 was introduced into an acrystalliferous (Cry⁻) B.t., HD-1 Cry B (A. I. Aronson, Purdue University), host by electroporation. Expression of an approximately 155 kDa protein was verified by SDS-PAGE. Broth containing spores and crystals was used for determination of toxicity to pharaoh ants (*Monomorium phraonis*).

EXAMPLE 8

Molecular Cloning and Expression of a Novel Toxin Gene from *Bacillus thuringiensis* Strain PS140E2

Total cellular DNA was prepared from *Bacillus thuringiensis* (B.t.) cells as described in Example 5. A gene library was constructed from PS1402 DNA partially digested with NdeII. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The NdeII inserts were ligated into BamHI-digested LambdaGem-11 (Promega, Madison, Wis.). Recombinant phage were packaged and plated on *E. coli* KW251 cells. Plaques were screened by hybridization to an oligonucleotide probe deduced from the amino acid sequence of the PS140E2 35 kDa toxin. The sequence of this probe was: 5' TTT CAT TTT TC(A/T) AAT ATT TTA GAT TAT AAA 3' (SEQ ID NO. 45).

Hybridizing phage were plaque-purified and used to infect liquid cultures of *E. coli* KW251 cells for isolation of DNA by standard procedures (Maniatis et al., supra).

For subcloning the gene encoding the approximately 35 kDa PS140E2 toxin, preparative amounts of phage DNA were digested with SalI and electrophoresed on an agarose gel. The approximately 13.5 kbp band containing the toxin gene was excised from the gel, electroeluted from the gel slice, and purified by ion exchange chromatography as described above. The purified DNA insert was ligated into XhoI-digested pHTBlueII (an *E. coli/B. thuringiensis* shuttle vector comprised of pBluescript S/K [Stratagene, La Jolla, Calif.] and the replication origin from a resident *B.t.* plasmid [Lereclus et al. (1989) *FEMS Microbiology Letters* 60:211–218]). The ligation mix was used to transform frozen, competent *E. coli* NM522 cells (ATCC 47000). β-galactosidase negative transformants were screened by restriction digestion of alkaline lysate plasmid minipreps as above. The desired plasmid construct, pMYC2367, contains a toxin gene that is novel compared to other toxin genes containing insecticidal proteins.

pMYC2367 was introduced into the acrystalliferous (Cry⁻) B.t. host, CryB (A. Aronson, Purdue University, West Lafayette, Ind.), by electroporation. Expression of the 35 kDa toxin was demonstrated by SDS-PAGE analysis.

EXAMPLE 9

Molecular Cloning and Expression of a Novel Toxin Gene from *Bacillus thuringiensis* Strain PS211B2

Total cellular DNA was prepared from *Bacillus thuringiensis* (B.t.) cells as described in Example 5.

An approximately 300 bp-sized fragment of the novel toxin gene (estimated size: 80 kDa) was obtained by polymerase chain reaction (PCR) amplification from PS211B2 cellular DNA using the following primers: "Forward": 5' GCAGGATCCGATTATATT (TA) GATAT (TA) A (CGA) TCC 3' (SEQ ID NO. 48), and "Reverse": 5' GCG GCC GCA CTT CAT CTT C(TA)G G(TA)G CAT T(TA)G CAT A(TA)G TAT C 3' (SEQ ID NO. 49). This DNA fragment was cloned into pBluescript II SK- (Stratagene, La Jolla, Calif.) and the DNA sequence determined by dideoxynucleotide sequencing methodology (Sanger et al. [1977] *Proc. Natl. Acad. Sci. USA* 74:5463–5467) using Sequenase (US Biochemical, Cleveland, Ohio). This fragment was subsequently radiolabelled with ³²P and used as a probe in standard hybridization screens of recombinant phage libraries.

A gene library was constructed from PS211B2 DNA partially digested with NdeII. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The NdeII inserts were ligated into BamHI-digested LambdaGem-11 (Promega, Madison, Wis.). Recombinant phage were packaged and plated on *E. coli* KW251 (Promega, Madison, Wis.) cells. Plaques were screened by hybridization with the probe described above. Hybridizing phage were plaque-purified and used to infect liquid cultures of *E. coli* KW251 cells for isolation of DNA by standard procedures (Maniatis et al., supra).

For subcloning the gene, preparative amounts of phage DNA were digested with SalI. The approximately 16 kbp band was ligated into XhoI-digested pHTBlueII (an *E. coli/B. thuringiensis* shuttle vector composed of pBluescript II SK- [Stratagene, La Jolla, Calif.] and the replication origin from a resident *B.t.* plasmid [Lereclus et al., supra]). The ligation mix was used to transform frozen, competent *E. coli* NM522 cells (ATCC 47000). β-galactosidase-transformants were screened by restriction digestion of alkaline lysate plasmid minipreps as above. The desired plasmid construct, pMYC2371, contains a toxin gene that is novel compared to other toxin genes containing insecticidal proteins.

Sequence analysis of the toxin gene revealed that it encodes a protein of approximately 80,000 daltons, deduced from the DNA sequence. The nucleotide and deduced amino acid sequences are shown in SEQ ID NOS. 50 and 51, respectively. pMYC2371 was introduced into the acrystalliferous (Cry⁻) B.t. host, CryB (A. Aronson, Purdue University, West Lafayette, Ind.), by electroporation. Expression of the approximately 80 kDa toxin was demonstrated by SDS-PAGE analysis.

EXAMPLE 10

Activity of the *B.t.* Toxin Protein and Gene Product Against Ants

Broths were tested for the presence of β-exotoxin by a larval house fly bioassay (Campbell, D. P., Dieball, D. E., Bracket, J. M. [1987] "Rapid HPLC assay for the β-exotoxin of *Bacillus thuringiensis*," *J. Agric. Food Chem.* 35:156–158). Only isolates which tested free of β-exotoxin were used in the assays against ants.

A bait was made consisting of 10% *Bacillus thuringiensis* isolates of the invention and Crosse and Blackwell mint apple jelly. Approximately 100 ants were placed in each plastic test chamber replicate with the baits. Control experiments were performed with untreated mint apple jelly. Each test was replicated a minimum of 10 times. Mortality was assessed at 21 days after introduction of the bait to the ants. Results are shown below:

TABLE 6

Toxicity of *B. thuringiensis* isolates to the pharaoh ant (*Monomorium pharaonis*)

| B.t. Isolate | Percent Mortality |
| --- | --- |
| PS140E2 | 91 |
| PS 86Q3 | 84 |
| Control | 11 |
| PS211B2 | 90.0 |
| Control | 3.8 |

EXAMPLE 11

Activity of the *B.t.* Toxin Protein and Gene Product Against Ants

Honey buffered with phosphate at pH 6.5 containing *B.t.* was fed to 5 replicates of approximately 100 worker ants for 21 days. Ants were provided water ad libitum. Totoal mortality (in %) over the test period was compared to controls.

TABLE 7

Three week mortality (%) on pharaoh ant workers

| Sample | % toxin in final bait | % mortality |
| --- | --- | --- |
| PS86Q3 | 20 | 100 |
| Honey only control | — | 16 |
| PS211B2 | 5 | 100 |
| PS140E2 | 10 | 98 |
| Control rearing diet | — | 61 |

EXAMPLE 12

Cloning of Novel Ant-Active Genes Using Generic Oligonucleotide Primers

The formicidal gene of a new formicidal *B.t.* can be obtained from DNA of the strain by performing the standard polymerase chain reaction procedure as in Example 6 using the oligonucleotides of SEQ ID NO. 33 or AGGAACAAAY-TCAAKWCGRTCTA (SEQ ID NO. 34) as reverse primers and SEQ ID NO. 12, SEQ ID NO. 13, SEQ ID NO. 15, SEQ ID NO. 16, SEQ ID NO. 23, SEQ ID NO. 27, SEQ ID NO. 29, or SEQ ID NO. 24 as forward primers. The expected PCR fragments would be approximately 330 to 600 bp with either reverse primer and SEQ ID NO. 12 or SEQ ID NO. 13, 1000 to 1400 bp with either reverse primer and SEQ ID NO. 15 or SEQ ID NO. 16, and 1800 to 2100 bp with either reverse primer and any of the three N-terminal primers, SEQ ID NO. 27, SEQ ID NO. 23, SEQ ID NO. 29, and SEQ ID NO. 24. Alternatively, a complement from the primer family described by SEQ ID NO. 12 and SEQ ID NO. 13 can be used as reverse primer with SEQ ID NO. 15, SEQ ID NO. 16, SEQ ID NO. 23, SEQ ID NO. 27, SEQ ID NO. 29, or SEQ ID NO. 24 as forward primers. The expected PCR fragments would be approximately 650 to 1000 bp with SEQ ID NO. 15 or SEQ ID NO. 16, and 1400 to 1800 bp for the four N-terminal primers (SEQ ID NO. 27, SEQ ID NO. 23, SEQ ID NO. 29, and SEQ ID NO. 24).

As another alternative, the reverse primer SEQ ID NO. 31 can be used with any of the four N-terminal forward primers to yield fragments of approximately 2550–3100 bp; 1750–2150 bp with the forward primers SEQ ID NOS. 15 or 16; 850–1400 bp with SEQ ID NOS. 12 or 13; and 550–1050 bp with the forward primer (TTTAGATCGT(AorC) TTGA(G or A)TTT(A or G)T(A or T)CC (SEQ ID NO. 35).

As yet another alternative, the ITSED (SEQ ID NO 36) reverse primer (TCTCCATCTTCTGA(G or A)G(T or A)AAT) (SEQ ID NO. 37) can be used with the N-terminal forward primers (SEQ ID NO. 23, SEQ ID NO. 24, SEQ ID NO. 27, and SEQ ID NO. 29) to yield fragments of approximately 3550–4050 bp; 2600–3100 bp with forward primers SEQ ID NOS. 15 or 16; 1800–2400 bp with forward primers SEQ ID NOS. 12 or 13; and 1500–2050 bp with forward primer SEQ ID NO. 35.

Amplified DNA fragments of the indicated sizes can be radiolabeled and used as probes to clone the entire gene as in Example 6.

EXAMPLE 13

Insertion of Toxin Gene Into Plants

One aspect of the subject invention is the transformation of plants with genes coding for a formicidal toxin. The transformed plants are resistant to attack by ants.

Genes encoding formicidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the *B.t.* toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System,* Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. Also, advantageously, plants encoding a truncated toxin will be used. The truncated toxin typically will encode about 55% to about 80% of the full length toxin. Methods for creating synthetic *B.t.* genes for use in plants are known in the art.

EXAMPLE 14

Cloning of Novel *B. thuringiensis* Genes Into Insect Viruses

A number of viruses are known to infect insects. These viruses include, for example, baculoviruses and entomopox viruses. In one embodiment of the subject invention, ant-active genes, as described herein, can be placed with the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G . Harris, M. Hirst, T. Booth, R. D. Possee (1990) *J. Gen. Virol.* 71:1535–1544) and Martens et al. (Martens, J. W. M., G. Honee, D. Zuidema, J. W. M. van Lent, B. Visser, J. M. Vlak (1990) *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A substantially pure toxin protein wherein said toxin has activity against a hymenopteran pest and has at least one characteristic selected from the group consisting of:

(a) the amino acid sequence of said toxin conforms to the Generic Formula (SEQ ID NO.39);

(b) the amino acid sequence of said toxin is at least 75% identical to toxin 86Q3a (SEQ ID NO.8);

(c) the DNA which codes for said toxin hybridizes with DNA which codes for all or a part of toxin 86Q3a having pesticidal activity wherein hybridization occurs at 42° C. in hybridization buffer containing 5× SSC/0.25% SDS and wash occurs at 55° C. with 0.1× SSC/0.1% SDS;

(d) the DNA which codes for said toxin hybridizes with a probe selected from the group consisting of SEQ ID NO.12, SEQ ID NO.15 wherein said toxin has an amino acid sequence other than SEQ ID NO.2 (toxin 17a) and SEQ ID NO.4 (toxin 17b), SEQ ID NO.16, SEQ ID NO.27 wherein said toxin has an amino acid sequence other than SEQ ID NO.6 (toxin 33F2), SEQ ID NO.23 wherein said toxin has an amino acid sequence other than SEQ ID NO.2, SEQ ID NO.24 wherein said toxin has an amino acid sequence other than SEQ ID NO.10 (toxin 63B), and SEQ ID NO.29 wherein said toxin has an amino acid sequence other than SEQ ID NO.2 and SEQ ID NO.4 wherein hybridization occurs at 42° C. in hybridization buffer containing 5× SSC/0.25% SDS and wash occurs at 55° C. with 0.1× SSC/0.1% SDS;

(e) a portion of the nucleotide sequence coding for said toxin can be amplified from total cellular DNA from a *Bacillus thuringiensis* strain using polymerase chain reaction with a reverse primer selected from the group consisting of SEQ ID NO.34, SEQ ID NO.33, SEQ ID NO.31, SEQ ID NO.37, and the full complements of SEQ ID NO.12 or SEQ ID NO.13; and a forward primer selected from the group consisting of SEQ ID NO.12, SEQ ID NO.15 wherein said toxin has an amino acid sequence other than SEQ ID NO.2 and SEQ ID NO.4, SEQ ID NO.16, SEQ ID NO.27 wherein said toxin has an amino acid sequence other than SEQ ID NO.6, SEQ ID NO.23 wherein said toxin has an amino acid sequence other than SEQ ID NO.2, SEQ ID NO.24 wherein said toxin has an amino acid sequence other than SEQ ID NO.10, and SEQ ID NO.29 wherein said toxin has an amino acid sequence other than SEQ ID NO.2 and SEQ ID NO.4; and (f) said toxin is immunoreactive with an antibody which immunoreacts with a toxin selected from the group consisting of toxins expressed by PS86Q3, toxins expressed by PS140E2, and toxins expressed by PS211B2.

2. The hymenopteran-active toxin, according to claim 1, wherein said toxin conforms to the Generic Formula (SEQ ID NO.39).

3. The hymenopteran-active toxin, according to claim 1, wherein the DNA encoding said toxin hybridizes with DNA which encodes all or a pesticidal part of toxin 86Q3a wherein hybridization occurs at 42° C. in hybridization buffer containing 5× SSC/0.25% SDS and wash occurs at 55° C. with 0.1× SSC/0.1% SDS.

4. The hymenopteran-active toxin, according to claim 1, wherein the DNA encoding for said toxin hybridizes with a probe selected from the group consisting of SEQ ID NO.12, SEQ ID NO.15 wherein said toxin has an amino acid sequence other than SEQ ID NO.2 and SEQ ID NO.4, SEQ ID NO.16, SEQ ID NO.27 wherein said toxin has an amino acid sequence other than SEQ ID NO.6, SEQ ID NO.23 wherein said toxin has an amino acid sequence other than SEQ ID NO.2, SEQ ID NO.24 wherein said toxin has an amino acid sequence other than SEQ ID NO. 10, and SEQ ID NO.29 wherein said toxin has an amino acid sequence other than SEQ ID NO.2 and SEQ ID NO.4 wherein hybridization occurs at 42° C. in hybridization buffer containing 5× SSC/0.25% SDS and wash occurs at 55° C. with 0.1× SSC/0.1% SDS.

5. The hymenopteran-active toxin, according to claim 1, wherein said toxin is immunoreactive with an antibody which immunoreacts with toxin 86Q3a.

6. The hymenopteran-active toxin, according to claim 1, wherein a portion of the nucleotide sequence coding for said toxin can be amplified from total cellular DNA from a *Bacillus thuringiensis* strain using polymerase chain reaction with a reverse primer selected from the group consisting of SEQ ID NO.34, SEQ ID NO.33, SEQ ID NO.37, SEQ ID NO. 31, and the full complements of SEQ ID NO. 12 or SEQ ID NO. 13; and a forward primer selected from the group consisting of SEQ ID NO. 12, SEQ ID NO. 15 wherein said toxin has an amino acid sequence other than SEQ ID NO. 2 and SEQ ID NO. 4, SEQ ID NO.16, SEQ ID NO. 27 wherein said toxin has an amino acid sequence other than SEQ ID NO. 6, SEQ ID NO. 23 wherein said toxin has an amino acid sequence other than SEQ ID NO. 2, SEQ ID NO. 24 wherein said toxin has an amino acid sequence other than SEQ ID NO. 10, and SEQ ID NO. 29 wherein said toxin has an amino acid sequence other than SEQ ID NO. 2 and SEQ ID NO. 4.

7. The hymenopteran-active toxin, according to claim 6, wherein said reverse primer is SEQ ID NO. 33 or SEQ ID NO. 34 and (a) the forward primer is SEQ ID NO. 12, wherein said toxin has an amino acid sequence other than SEQ ID NO. 6 and the polymerase chain reaction fragment is approximately 330 to 600 bp;

(b) the forward primer is SEQ ID NO. 15 wherein said toxin has an amino acid sequence other than SEQ ID NO. 2 and SEQ ID NO. 4, or SEQ ID NO. 16, and the polymerase chain reaction fragment is approximately 1000 to 1400 bp; or (c) the forward primer is SEQ ID NO. 27 wherein said toxin has an amino acid sequence other than SEQ ID NO. 6, SEQ ID NO. 23 wherein said toxin has an amino acid sequence other than SEQ ID NO. 2 and SEQ ID NO. 4, SEQ ID NO. 24 wherein said toxin has an amino acid sequence other than SEQ ID NO. 10, or SEQ ID NO. 29 wherein said toxin has an amino acid sequence other than SEQ ID NO. 2 and SEQ ID NO. 4, and the polymerase chain reaction fragment is 1800 to 2100 bp.

8. The hymenopteran-active toxin, according to claim 6, wherein said reverse primer is a full complement of SEQ ID NO. 12 or SEQ ID NO. 13 and
 (a) the forward primer is SEQ ID NO. 15 wherein said toxin has an amino acid sequence other than SEQ ID NO. 2 and SEQ ID NO. 4, or SEQ ID NO. 16, and the polymerase chain reaction fragment is approximately 650 to 1000 bp; or
 (b) the forward primer is SEQ ID NO. 27 wherein said toxin has an amino acid sequence other than SEQ ID NO. 6, SEQ ID NO. 23 wherein said toxin has an amino acid sequence other than SEQ ID NO. 2 and SEQ ID NO. 4, SEQ ID NO. 24 wherein said toxin has an amino acid sequence other than SEQ ID NO. 10, or SEQ ID NO. 29 wherein said toxin has an amino acid sequence other than SEQ ID NO. 2 and SEQ ID NO. 4, and the polymerase chain reaction fragment is approximately 1000 to 1400 bp.

9. The hymenopteran-active toxin, according to claim 6, wherein said reverse primer is SEQ ID NO. 31 and
 (a) the forward primer is SEQ ID NO. 27 wherein said toxin has an amino acid sequence other than SEQ ID NO. 6, SEQ ID NO. 23 wherein said toxin has an amino acid sequence other than SEQ ID NO. 2 and SEQ ID NO. 4, or SEQ ID NO. 29 wherein said toxin has an amino acid sequence other than SEQ ID NO. 2 and SEQ ID NO. 4, and the polymerase chain reaction fragment is approximately 2550–3100 bp;
 (b) the forward primer is SEQ ID NO. 15 wherein said toxin has an amino acid sequence other than SEQ ID NO. 2 and SEQ ID NO. 4, or SEQ ID NO. 16, and the resulting polymerase chain reaction fragment is 1750–2150 bp;
 (c) the forward primer is SEQ ID NO. 12 wherein said toxin has an amino acid sequence other than SEQ ID NO. 6 and the polymerase chain reaction fragment is approximately 850–1400 bp.

10. The hymenopteran-active toxin according to claim 6, wherein said reverse primer is SEQ ID NO. 37 and
 (a) the forward primer is SEQ ID NO. 27 wherein said toxin has an amino acid sequence other than SEQ ID NO. 6, SEQ ID NO. 23 wherein said toxin has an amino acid sequence other than SEQ ID NO. 2 and SEQ ID NO. 4, or SEQ ID NO. 29 wherein said toxin has an amino acid sequence other than SEQ ID NO. 2 and SEQ ID NO. 4, and the polymerase chain reaction fragment is approximately 3550–4050 bp;
 (b) the forward primer is SEQ ID NO. 15 wherein said toxin has an amino acid sequence other than SEQ ID NO. 2 and SEQ ID NO. 4, or SEQ ID NO. 16, and the resulting polymerase chain reaction fragment is 2600–3100 bp;
 (c) the forward primer is SEQ ID NO. 12 wherein said toxin has an amino acid sequence other than SEQ ID NO. 6 and the polymerase chain reaction fragment is approximately 1800–2400 bp.

11. A substantially pure hymenopteran-active toxin comprising an amino acid sequence selected from the group consisting of the amino acid sequence shown in SEQ ID NO.8, SEQ ID NO.51, SEQ ID NO.43 and pesticidal portions thereof.

12. A substantially pure hymenopteran-active toxin as expressed by PS140E2 and which comprises the amino acid sequence of SEQ ID NO.44.

13. The toxin, according to claim 11, wherein said toxin has the amino acid sequence shown in SEQ ID NO. 51.

14. The toxin, according to claim 11, wherein said toxin has the amino acid sequence shown in SEQ ID NO. 43.

15. The hymenopteran-active toxin, according to claim 12, wherein said toxin has the amino acid sequence shown in SEQ ID NO. 8.

* * * * *

UNITED STATES PATENT AND TRADEMARK OFFICE
CERTIFICATE OF CORRECTION

PATENT NO. : 6,077,937

DATED : June 20, 2000

INVENTOR(S) : Payne *et al.*

It is certified that error appears in the above-identified patent and that said Letters Patent is hereby corrected as shown below:

Column 9, line 55: "K = K or R" should read --$\underline{K}$ = K or R--.

Column 9, line 56: "E = E or D" should read --$\underline{E}$ = E or D--.

Column 9, line 57: "L = L or I" should read --$\underline{L}$ = L or I--.

Column 14, line 23: "125I" should read --$^{125}$I--.

Column 120, line 39 (claim 15): "12" should read --11--.

Signed and Sealed this

Eighth Day of May, 2001

*Attest:*

NICHOLAS P. GODICI

*Attesting Officer*   *Acting Director of the United States Patent and Trademark Office*